United States Patent
Yasui et al.

(10) Patent No.: US 8,008,028 B2
(45) Date of Patent: Aug. 30, 2011

(54) PANEL CELL USED FOR GRANULOCYTE ANTIBODY DETECTION

(75) Inventors: Kazuta Yasui, Osaka (JP); Fumiya Hirayama, Osaka (JP); Rika Furuta, Kyoto (JP); Nobuki Matsuyama, Higashiosaka (JP); Yoshitaka Kojima, Higashiosaka (JP); Toru Miyazaki, Sapporo (JP); Hisami Ikeda, Sapporo (JP); Yoshihisa Watanabe, Tokyo (JP)

(73) Assignees: Japanese Red Cross Society, Tokyo-to (JP); Wakunaga Pharmaceutical Co., Ltd., Osaka-fu (JP)

( * ) Notice: Subject to any disclaimer, the term of this patent is extended or adjusted under 35 U.S.C. 154(b) by 46 days.

(21) Appl. No.: 12/225,477

(22) PCT Filed: Mar. 13, 2007

(86) PCT No.: PCT/JP2007/054986
§ 371 (c)(1),
(2), (4) Date: Sep. 23, 2008

(87) PCT Pub. No.: WO2007/108368
PCT Pub. Date: Sep. 27, 2007

(65) Prior Publication Data
US 2009/0208978 A1 Aug. 20, 2009

(30) Foreign Application Priority Data
Mar. 23, 2006 (JP) ................................ 2006-081236

(51) Int. Cl.
*G01N 33/53* (2006.01)
*C12N 15/63* (2006.01)
(52) U.S. Cl. ........................................ 435/7.2; 435/455
(58) Field of Classification Search .................. None
See application file for complete search history.

(56) References Cited

U.S. PATENT DOCUMENTS
2005/0003484 A1   1/2005   Hirano et al.

OTHER PUBLICATIONS

Lucas et al., Transfusion, 2002, v.42, pp. 462-468.*
Bux et al., Blood,1999v.93, p. 357-362.*
K. P. M. Van Kessel et al., "Quantitation of Conjugate Formation Between Human Polymorphonuclear Leukocytes and Antibody-Coated Target Cells by Flow Cytometry: The Role of Fc Receptor and LFA-1 Antigen", Journal of Leukocyte Biology, vol. 46, No. 5, pp. 467-475, 1989.
K. Miyazaki et al., "P57-O: Preparation of HNA-1a and 1b Panels by Using FCGR3B Gene Expressing Cell," Japanese Journal of Transfusion Medicine, vol. 50, No. 2, pp. 297, P57-O, 2004 (English translation).
K. Yasui et al., "Detection of Anti-HNA Antibody in Serum With HNA-1a, -1b, and -2a Gene Expression Panel Cell Line," Ketsueki Jigyo, vol. 29, No. 2, p. 293, 42, Aug. 2006 (English translation).
F. Hirayama et al., "New Detection System of Granulocyte Antibodies", Ketsueki Jigyo, vol. 29, No. 2, p. 251, 3-3, Aug. 2006 (English translation).
K. Yasui et al., "O-51: Production of HNA-1a and -1b Gene Expressing Panel Cell Lines for Detecting Granulocyte Antibody," Japanese Journal of Transfusion Medicine, vol. 52, No. 2, p. 252, O-51, May 2006 (English translation).

* cited by examiner

*Primary Examiner* — Michail Belyavskyi
(74) *Attorney, Agent, or Firm* — Wenderoth, Lind & Ponack, L.L.P.

(57) ABSTRACT

A panel cell for detecting anti-HNA antibody is disclosed. The panel cell is obtained by introducing a DNA coding for an HNA antigen corresponding to the anti-HNA antibody into a cell so as to enable the expression of the DNA under the condition for use in the detection procedure, wherein the cell for DNA introduction exhibits no detectable reaction with anti-HLA-ABC antibody, anti-HLA-DR antibody, anti-HLA-DQ antibody, anti-HLA-DP antibody, anti-HNA-1 antibody, anti-HNA-2a antibody, anti-HNA-3a antibody, anti-HNA-4 antibody, anti-HNA-5 antibody, and serum from normal subject, in the detection procedure. The panel cell allows accurate and rapid detection of granulocyte antibody.

11 Claims, 10 Drawing Sheets

Fig. 9

PANEL CELL USED FOR GRANULOCYTE ANTIBODY DETECTION

This application is a U.S. national stage of International Application No. PCT/JP2007/054986 filed Mar. 13, 2007.

REFERENCE TO RELATED APPLICATION

This patent application is an application claiming priority based on Japanese Patent Application No. 2006-81236 (filing date: Mar. 23, 2006). The whole disclosure of Japanese Patent Application No. 2006-81236 is incorporated herein by reference.

BACKGROUND OF THE INVENTION

1. Field of the Invention

The present invention relates to the field of clinical tests, more particularly to a method for accurately and rapidly detecting an antibody against a granulocyte antigen (granulocyte antibody) in serum which is considered as one of the causes of granulopenia (neutropenia) and transfusion side effect, and a panel cell used for said method.

2. Background Art

In recent years, diseases in which a granulocyte (neutrophil) antigen is involved have been reported in a variety of clinical situations. Diseases in which an isoantibody is involved include isoimmune neonatal neutropenia, isoimmune neutropenia after hematopoietic stem cell transplantation, granulocyte transfusion refractoriness, transfusion-related acute lung injury, anhemolytic transfusion side effect, and the like. Also, diseases in which autoantibody is involved include primary autoimmune neutropenia, secondary autoimmune neutropenia, and the like. In these diseases, an anti-human leukocyte antigen (HLA) antibody may be observed concomitantly with the granulocyte antibody, and thus there is a need for an examination method for accurately and rapidly discriminating and identifying these antibodies.

The examination of granulocyte antibody usually employs: a method for detecting granulocyte antibody by flow cytometry using blood granulocyte as a panel cell (cell for discrimination) (GIFT); a method by using the agglutination of granulocytes as an index (GAT); a method for reacting serum and a mouse monoclonal antibody with granulocyte to determine a resulting antigen-antibody complex (MAIGA); a method by using a plate having granulocyte (or granulocyte extraction antigen) immobilized thereon and reacting the plate with a sample to judge the agglutination of the bonded antibody and the anti-human IgG sensitive blood cell (or sensitive beads) as an index (MPHA); a method in which the detection step involved in MPHA is carried out by using a labeled antibody (EIA), and the like. In the method by using human granulocyte, blood is taken from a blood donor and granulocyte is isolated from the blood thus obtained for every examination, so that the reactivities with the granulocyte antibodies vary individually. Also, in the method which uses the human granulocyte as a panel cell, high levels of backgrounds are observed in measurement results of flow cytometry and the like, and the levels of the backgrounds vary depending on individual granulocytes, so that it is difficult to obtain accurate test results stably. Thus, there is a need for the development of a panel cell strain for detecting granulocyte antibody which allows obtaining accurate test results stably.

Hitherto, researchers in many countries including Japan have tried to develop a panel cell strain for detecting the granulocyte antibody. J. Bux et al. in Justus Liebig University have prepared a panel cell strain which expresses granulocyte antigens HNA-1a, HNA-1b and HNA-SH by transfecting genes coding for these antigens into CHO cells (Chinese hamster ovary cell line) (Blood, vol. 93, No. 1, 1999: pp. 357-362). Also, Miyazaki et al. in Hokkaido Red Cross Blood Center have prepared a CHO cell and a COS-7 cell (African green monkey kidney cell line) which express HNA-1a and HNA-1b (Japanese Journal of Transfusion Medicine 50, 2, 2004: pp 297) as well as a 293T cell (Human kidney cell line) expressing HNA-2a (Japanese Journal of Transfusion Medicine 51, 2, 2005: pp 188).

SUMMARY OF THE INVENTION

The present inventors have found that serum granulocyte antibody can be accurately and rapidly detected by using a panel cell in which DNA encoding an HNA antigen has been incorporated in an expressible form into a cell which will not respond to an anti-HLA antibody, an anti-HNA antibody and serum from a normal subject. The present invention is based on this finding.

Thus, the object of the present invention is to provide a panel cell which enables the accurate and rapid detection of a granulocyte antibody.

The panel cell of the invention is a panel cell for detecting an anti-HNA antibody, which is obtained by introducing a DNA coding for an HNA antigen corresponding to said anti-HNA antibody into a cell so as to enable the expression of said DNA under the condition for use in the detection procedure, wherein the cell for DNA introduction exhibits no detectable reaction with anti-HLA-ABC antibody, anti-HLA-DR antibody, anti-HLA-DQ antibody, anti-HLA-DP antibody, anti-HNA-1 antibody, anti-HNA-2a antibody, anti-HNA-3a antibody, anti-HNA-4 antibody, anti-HNA-5 antibody, and serum from normal subject, in the detection procedure.

According to the present invention, it is possible to stably obtain accurate test results in the detection of granulocyte antibody with a low background level.

BRIEF DESCRIPTION OF THE DRAWINGS

FIG. 9 is the electrophoresis photogram which shows the expression of the transgene in KY-4a cell, KY-4b cell, KY-5a cell, KY-5b cell and KY-mock pn cell.

DETAILED DESCRIPTION OF THE INVENTION

Figure 1:
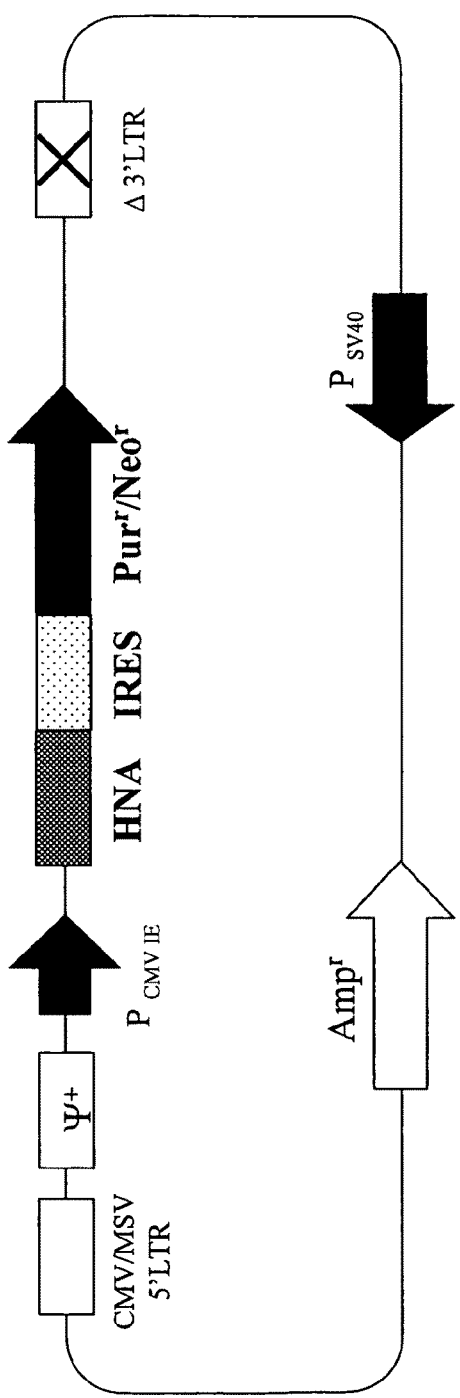
FIG. 1 shows the structure of a vector for introducing the HNA gene into a cell.

The cell subjected to gene transfer in the present invention is a cell which exhibits no detectable reaction with anti-HLA-ABC antibody, anti-HLA-DR antibody, anti-HLA-DQ antibody, anti-HLA-DP antibody, anti-HNA-1 antibody, anti-HNA-2a antibody, anti-HNA-3a antibody, anti-HNA-4 antibody, anti-HNA-5 antibody, and serum from normal subject, in the detection procedure. The phrase "exhibit(s) no detectable reaction in the detection procedure" used herein means that the cell exhibits no reaction with respective antibodies or serum, or exhibits reaction lower than detection limit in the procedure used for the detection of anti-HNA antibodies. The cells satisfying such definition can be determined by examining their reactivities with the antibodies and serum described above. Such cell is preferably selected from mammalian cells, more preferably from nonadherent cells. The cell satisfying such definition includes myelocytic leukemia cell, K562 cell (ATCC No. CCL-243, RCB No. of Cell Bank in Riken Bioresource Center: RCB0027).

A panel cell according to the present invention is prepared by introducing a DNA coding for an HNA antigen corresponding to the anti-HNA antibody to be detected into the cell described above so as to enable the expression of said DNA under the condition for use in the detection procedure.

The human granulocyte antigen includes HNA-1a antigen, HNA-1b antigen, HNA-1SH antigen, HNA-2a antigen, HNA-3a antigen, HNA-4a antigen, and HNA-5a antigen corresponding to anti-HNA-1a antibody, anti-HNA-1b antibody, anti-HNA-1SH antibody, anti-HNA-2a antibody, anti-HNA-3a antibody, anti-HNA-4a antibody, and anti-HNA-5a antibody, respectively, and are selected according to the antibody to be detected. It is also possible to employ the human granulocyte antigen such as HNA-4b antigen or HNA-5b antigen corresponding to anti-HNA-4b antibody or anti-HNA-5b antibody.

In a preferred embodiment of the present invention, the anti-HNA antibody to be detected is the anti-HNA-1a antibody, and the HNA antigen corresponding thereto is the HNA-1a antigen. As the DNA coding for the HNA-1a antigen, the genomic DNA or cDNA of the HNA-1a antigen gene may be preferably employed. The cDNA of the HNA-1a antigen gene includes a DNA comprising a nucleotide sequence represented by SEQ ID NO: 1, which encodes the amino acid sequence represented by SEQ ID NO: 2. The cDNA of the HNA-1a antigen gene can be amplified, for example, by RT-PCR using primers designed on the basis of the sequences of the 5'-terminal and 3'-terminal portions in SEQ ID NO: 1 and using as a template mRNA obtained from a cell which expresses the antigen.

In another preferred embodiment of the present invention, the anti-HNA antibody to be detected is the anti-HNA-1b antibody, and the HNA antigen corresponding thereto is the HNA-1b antigen. As the DNA coding for the HNA-1b antigen, the genomic DNA or cDNA of the HNA-1b antigen gene may be preferably employed. The cDNA of the HNA-1b antigen gene includes a DNA comprising a nucleotide sequence represented by SEQ ID NO: 3, which encodes the amino acid sequence represented by SEQ ID NO: 4. The cDNA of the HNA-1b antigen gene can be amplified, for example, by RT-PCR using primers designed on the basis of the sequences of the 5'-terminal and 3'-terminal portions in SEQ ID NO: 3 and using as a template mRNA obtained from a cell which expresses the antigen.

In another preferred embodiment of the present invention, the anti-HNA antibody to be detected is the anti-HNA-2a antibody, and the HNA antigen corresponding thereto is the HNA-2a antigen. As the DNA coding for the HNA-2a antigen, the genomic DNA or cDNA of the HNA-2a antigen gene may be preferably employed. The cDNA of the HNA-2a antigen gene includes a DNA comprising a nucleotide sequence represented by SEQ ID NO: 5, which encodes the amino acid sequence represented by SEQ ID NO: 6. The cDNA of the HNA-2a antigen gene can be amplified, for example, by RT-PCR using primers designed on the basis of the sequences of the 5'-terminal and 3'-terminal portions in SEQ ID NO: 5 and using as a template mRNA obtained from a cell which expresses the antigen.

In another preferred embodiment of the present invention, the anti-HNA antibody to be detected is the anti-HNA-4a antibody, and the HNA antigen corresponding thereto is the HNA-4a antigen. The HNA-4a antigen is a complex of a CD11bMart(+) antigen and a CD18 antigen. As the DNA coding for the HNA-4a antigen, the genomic DNA or cDNA of a CD11bMart(+) antigen gene and a CD18 antigen gene may be preferably employed. The cDNA of the CD11bMart(+) antigen gene includes a DNA comprising a nucleotide sequence represented by SEQ ID NO: 7, which encodes the amino acid sequence represented by SEQ ID NO: 8. The nucleotide sequence of the cDNA of the CD18 antigen gene and the amino acid sequence of the CD18 antigen are represented by SEQ ID NO: 15 and 16, respectively. The cDNA of the HNA-4a antigen gene can be amplified, for example, by RT-PCR using primers designed on the basis of the sequences of the 5'-terminal and 3'-terminal portions in SEQ ID NOS: 7 and 15 and using as a template mRNA obtained from a cell which expresses the antigen.

In another preferred embodiment of the present invention, the anti-HNA antibody to be detected is the anti-HNA-4b antibody, and the HNA antigen corresponding thereto is the HNA-4b antigen. The HNA-4b antigen is a complex of a CD11bMart(−) antigen and a CD18 antigen. As the DNA coding for the HNA-4b antigen, the genomic DNA or cDNA of a CD11bMart(−) antigen gene and a CD18 antigen gene may be preferably employed. The cDNA of the CD11bMart(−) antigen gene includes a DNA comprising a nucleotide sequence represented by SEQ ID NO: 9, which encodes the amino acid sequence represented by SEQ ID NO: 10. The nucleotide sequence of the cDNA of the CD18 antigen gene and the amino acid sequence of the CD18 antigen are represented by SEQ ID NO: 15 and 16, respectively. The cDNA of the HNA-4b antigen gene can be amplified, for example, by RT-PCR using primers designed on the basis of the sequences of the 5'-terminal and 3'-terminal portions in SEQ ID NOS: 9 and 15 and using as a template mRNA obtained from a cell which expresses the antigen.

In another preferred embodiment of the present invention, the anti-HNA antibody to be detected is the anti-HNA-5a antibody, and the HNA antigen corresponding thereto is the HNA-5a antigen. The HNA-5a antigen is a complex of a CD11aOnd(+) antigen and a CD18 antigen. As the DNA coding for the HNA-5a antigen, the genomic DNA or cDNA of a CD11aOnd(+) antigen gene and a CD18 antigen gene may be preferably employed. The cDNA of the CD11aOnd(+) antigen gene includes a DNA comprising a nucleotide sequence represented by SEQ ID NO: 11, which encodes the amino acid sequence represented by SEQ ID NO: 12. The nucleotide sequence of the cDNA of the CD18 antigen gene and the amino acid sequence of the CD18 antigen are represented by SEQ ID NO: 15 and 16, respectively. The cDNA of the HNA-5a antigen gene can be amplified, for example, by RT-PCR using primers designed on the basis of the sequences of the 5'-terminal and 3'-terminal portions in SEQ ID NOS: 11 and 15 and using as a template mRNA obtained from a cell which expresses the antigen.

In another preferred embodiment of the present invention, the anti-HNA antibody to be detected is the anti-HNA-5b antibody, and the HNA antigen corresponding thereto is the HNA-5b antigen. The HNA-5b antigen is a complex of a CD11aOnd(−) antigen and a CD18 antigen. As the DNA coding for the HNA-5b antigen, the genomic DNA or cDNA of a CD11aOnd(−) antigen gene and a CD18 antigen gene may be preferably employed. The cDNA of the CD11aOnd (−) antigen gene includes a DNA comprising a nucleotide sequence represented by SEQ ID NO: 13, which encodes the amino acid sequence represented by SEQ ID NO: 14. The nucleotide sequence of the cDNA of the CD18 antigen gene and the amino acid sequence of the CD18 antigen are represented by SEQ ID NO: 15 and 16, respectively. The cDNA of the HNA-5b antigen gene can be amplified, for example, by RT-PCR using primers designed on the basis of the sequences of the 5'-terminal and 3'-terminal portions in SEQ ID NOS: 13 and 15 and using as a template mRNA obtained from a cell which expresses the antigen.

The method for introducing DNA into a cell so as to enable the expression of said DNA may be carried out according to the standard technique well known in the art. For instance, the DNA of interest can be incorporated into a vector having a promoter which acts in a cell, and then the cell can be transformed with an expression vector thus obtained. As the promoter, any kinds of promoters such as constitutive promoter, inducible promoter, and the like may be used, and a CMV (cytomegalovirus) promoter which exhibits strong activity in mammalian cells is preferably used. As the vector, a variety of expression vectors which are capable of expressing the DNA in a cell may be used. In the present invention, particularly, the DNA coding for the HNA antigen is preferably incorporated into the genome of a cell, and thus an adeno-associated virus vector and a retrovirus vector are suitably used for this purpose. For instance, a fragment wherein a drug resistant gene (e.g. puromycin resistant gene) is linked to the downstream of the DNA through an IRES gene can be incorporated into a retrovirus vector. The resulting vector in the form of a recombinant virus can be used to infect a cell, so that the DNA can be introduced into the cell so as to enable the expression of said DNA. According to this method, a gene of interest is securely introduced into the chromosome of the cell by using the retrovirus vector, and further the gene of interest is securely expressed in the cell living in the presence of a drug by the IRES gene.

The panel cell according to the present invention may be used for detecting an anti-HNA antibody in a test sample. Accordingly, the present invention also provides a method of detecting an anti-HNA antibody in a test sample, comprising the steps of: (a) providing a test sample, (b) providing the panel cell according to any one of claims 1 to 11, and (c) bringing said test sample into contact with said panel cell, and detecting the binding of said panel cell with said anti-HNA antibody. As the test sample, samples containing antibody, particularly blood or serum samples are suitably used.

The binding of the panel cell with the anti-HNA antibody can be detected by the methods well known in the art, including, for example, a method using flow cytometry (GIFT), a method using the agglutination of granulocytes as an index (GAT), a method by reacting serum and a mouse monoclonal antibody with granulocyte and determining a resulting antigen-antibody complex (MAIGA), a method by using a plate having granulocyte (or granulocyte extraction antigen) immobilized thereon and reacting the plate with a sample to judge the agglutination of the bonded antibody and the anti-human IgG sensitive blood cell (or sensitive beads) as an index (MPHA), a method in which the detection step involved in MPHA is carried out by using a labeled antibody (EIA), and the like. The binding of the panel cell and the anti-HNA antibody is preferably detected by flow cytometry.

In the method of detecting the anti-HNA antibody described above, the panel cell according to the present invention can be used in an immobilized form on a carrier. The carrier preferably includes plates and beads of thermoplastic resins such as polystyrene, and nitrocellulose and nylon filters, glass fibers, glass beads, magnetic beads, organic polymer beads, microorganisms, blood cells, cell membrane fragments, and the like can be also used. The organic polymer beads include, for example, natural polymer particles such as insoluble agarose, cellulose and insoluble dextran, and thermoplastic synthetic resin beads such as polystyrene. The thermoplastic synthetic resin includes, in addition to polystyrene, polyethylene, polypropylene, acrylonitrile/styrene resin, acrylonitrile/butadiene/styrene resin, methacrylate resin, vinyl chloride, and the like.

The cell may be immobilized onto the carrier by mixing without preliminary treatment, by physicochemical modification, or by using a binding agent, through physicochemical bonds such as covalent bond, ionic bond, van der Waals bond, hydrogen bond, metallic bond, mechanical bond and magnetic bond or biological bonds such as antigen-antibody bond, receptor-ligand bond, enzyme-substrate bond and complementary bond of nucleic acids.

In the method of detecting the anti-HNA antibody, the panel cell according to the present invention acts as a reagent for detecting the anti-HNA antibody. Accordingly, the present invention also provides a reagent for detecting an anti-HNA antibody, comprising the panel cell according to the present invention. In the reagent according to the present invention, the panel cell may be the one which is immobilized on the carrier described above.

Furthermore, it is known that the anti-HNA antibody is involved in diseases. Accordingly, the present invention also provides a method of detecting or diagnosing disease that involves an anti-HNA antibody in a subject, particularly a human subject, comprising the steps of: (a) providing a serum sample derived from said subject, (b) providing the panel cell according to the present invention, and (c) bringing said serum sample into contact with said panel cell, and detecting the binding of said panel cell with said anti-HNA antibody. The detection of the binding of the panel cell with the anti-HNA antibody is as described above. The disease that involves an anti-HNA antibody includes isoimmune neonatal neutropenia, isoimmune neutropenia after hematopoietic stem cell transplantation, granulocyte transfusion refractoriness, transfusion-related acute lung injury, primary autoimmune neutropenia, secondary autoimmune neutropenia, and anhemolytic transfusion side effect. Furthermore, the reagent according to the present invention described above acts as a reagent for detecting or diagnosing these diseases.

Moreover, the panel cell according to the present invention can be used for producing a variety of HNA antigens. Accordingly, the present invention also provides a method of producing an HNA antigen, comprising the steps of: culturing the panel cell according to the present invention, and isolating the HNA antigen from the culture.

The panel cell according to the present invention can be used, as described above, for detecting an anti-HNA antibody in a test sample and for diagnosing the disease that involves the anti-HNA antibody in a subject, particularly a human subject. Accordingly, the present invention also provides the use of the panel cell according to the present invention for detecting an anti-HNA antibody in a test sample, and the use of the panel cell according to the present invention in the production of a reagent for detecting an anti-HNA antibody. In addition, the present invention provides the use of the panel cell according to the present invention, in the production of a reagent for diagnosing the disease that involves the anti-HNA antibody in a subject, particularly a human subject.

EXAMPLE

The present invention is more particularly described by way of examples, but the scope of the invention is not limited to these examples.

Reference Example 1

Selection of a Cell

In order to select a cell strain for use in the production of a panel cell, six nonadherent cells (K562 cell, Jurkat cell, THP-1 cell, Namalwa cell, CMK cell and L cell) as well as five adherent cells (Hela cell, 293T cell, COS-7 cell, 3T3 cell and CHO cell) were subjected to the following test. First, the reactivity of each cell with three healthy human sera (normal sera) was measured with a flow cytometer to check the increase of background level in each cell. Next, reactivity of each cell with anti-HLA antibodies (anti-HLA-ABC antibody and anti-HLA-DR antibody) or anti-HNA antibodies (anti-HNA-1 antibody, anti-HNA-2a antibody, anti-HNA-3a antibody, anti-HNA-4 antibody and anti-HNA-5 antibody) was measured with a flow cytometer using antibody labels such as fluorescein (FITC) and phycoerythrin (PE) as the indices to check the increase of background level in each cell. Also, with respect to the K562 cell, the reactivity thereof with a mixture of anti-HLA-DR antibody, anti-HLA-DQ antibody and anti-HLA-DP antibody was checked. In the above test, the reactivity of the cell with anti-HNA-3a antibody was checked by using anti-HNA-3a serum, and the reactivities of the cell with the other antibodies were checked by using each of the monoclonal antibodies. The result is shown in Table 1.

normal sera. On the other hand, five nonadherent cells (K562 cell, Jurkat cell, THP-1 cell, Namalwa cell, and CMK cell) and one adherent cell (COS-7 cell) exhibited almost no reactivity with normal sera. Furthermore, among the cells having no reactivity with normal serum, the K562 cell exhibited no reactivity with neither of anti-HLA antibodies nor anti-HNA antibodies. Thus, the K562 cell was selected as a cell into which the HNA gene is introduced.

Example 1

Preparation of a Cell Expressing Each of HNA-1a, HNA-1b and HNA-2a Antigens

Each of the cDNAs of HNA-1a antigen, HNA-1b antigen and HNA-2a antigen was prepared from peripheral monocyte obtained from a healthy subject having a genotype of HNA-1a/a, HNA-1b/b or HNA-2a/a, respectively. Specifically, whole RNA was extracted from each cell to synthesize cDNA by RT-PCR. The cDNA thus obtained was cloned into a commercially available plasmid pCR2.1-TOPO (Invitrogen, Carlsbad, Calif.) to confirm the DNA sequences of the HNA-1a gene, the HNA-1b gene or the HNA-2a gene. The cDNA sequence and the amino acid sequence of HNA-1a are listed in SEQ ID NO: 1 and SEQ ID NO: 2. The cDNA sequence and the amino acid sequence of HNA-1b are listed in SEQ ID NO: 3 and SEQ ID NO: 4. The cDNA sequence and the amino acid sequence of HNA-2a are listed in SEQ ID NO: 5 and SEQ ID NO: 6.

Next, each cDNA was subcloned between the BamHI site and the NotI site of the commercially available retrovirus vector pQCXIP (Becton Dickinson, San Jose, Calif.). The vectors containing cDNA of HNA-1a, HNA-1b and HNA-2a were designated as pQCXIP-1a, pQCXIP-1b and pQCXIP-2a, respectively. The structures of these vectors are shown in FIG. 1.

Next, pQCXIP-1a, pQCXIP-1b or pQCXIP-2a as well as pVSV-G (Becton Dickinson) were transfected into a gp-293T packaging cell strain (Becton Dickinson) by using Lipofe-

TABLE 1

Comparison of candidate cells to be transduced in reactivity with healthy human sera, as well as in HLA expression and HNA expression

|  |  | Non-adherent cell lines | | | | | | Adherent cell lines | | | | |
|---|---|---|---|---|---|---|---|---|---|---|---|---|
|  |  | K562 | Jurkat | THP-1 | Namalwa | CMK | L-cell | Hela | 293T | Cos7 | 3T3 | CHO |
| Normal Serum[#1] | | 0/3 | 0/3 | 0/3 | 0/3 | 0/3 | 3/3 | 1/3 | 2/3 | 0/3 | 2/3 | 2/3 weak |
| HLA[#2] | ABC | − | + | + | + | + | − | + | + | + | − | − |
|  | DR | − | − | − | + | − | + | − | − | + | − | − |
|  | DR, DQ, DP | − | NT | NT | NT | NT | NT | NT | NT | NT | NT | NT |
| HNA | 1[#3] | − | − | − | − | − | − | − | − | − | − | ± weak |
|  | 2a[#4] | − | − | − | − | − | − | − | − | − | − | − |
|  | 3a[#5] | − | NT | NT | NT | NT | NT | NT | NT | NT | NT | NT |
|  | 4[#6] | − | − | − | − | + | − | − | − | + | − | − |
|  | 5[#6] | − | + | + | + | + | − | − | − | − | − | − |

[#1] determined by indirect immunofluorescence test using FITC-anti-human IgG after incubating with three kinds of normal human sera.
[#2] determined by direct immunofluorescence test using FITC-anti-HLA-ABC antibody, PE-anti-HLA-DR antibody, as well as a mixture of PE-anti-HLA-DR antibody, PE-anti-HLA-DQ antibody and PE-anti-HLA-DP antibody.
[#3] determined by direct immunofluorescence test using FITC-TAG-1, FITC-TAG-2 and TAG-3.
[#4] determined by direct immunofluorescence test using FITC-TAG-4.
[#5] determined by indirect immunofluorescence test using FITC-anti-human IgG after incubating with HNA-3a-reactive serum.
[#6] determined by direct immunofluorescence test using PE-anti-HNA4 antibody (anti-Mac-1 antibody) and FITC-anti-HNA5 antibody (anti-LFA1 antibody).

As shown in Table 1, the L cell, the Hela cell, the 293T cell, the 3T3 cell, and the CHO cell exhibited high reactivities with tamine Plus reagent (Invitrogen) according to the standard protocol thereof. In this connection, another cell strain into which only pQCXIP containing no HNA gene was introduced was also prepared in the similar procedure.

The gp-293T cell thus transfected was cultured for 48 hours to give a supernatant containing $10^5$ particles/ml of recombinant virus particles. To a 0.1 ml portion of the supernatant was added $1 \times 10^6$ cells of K562 cell suspended in 0.9 ml of a culture medium for infection (10% FBS-containing RPMI1640 medium supplemented with Polybrene at a final concentration of 8 µg/ml), and the mixture was cultured for 2 hours, washed twice with a R10 medium (10% FBS-containing RPMI1640 medium), and then cultured in a RIO medium for 2 days. Subsequently, the puromycin-resistant cell among those which were infected with the recombinant virus was cloned by the limiting dilution method to give KY-1a cell, KY-1b cell and KY-2a cell which express HNA-1a, HNA-1b and HNA-2a, respectively, as well as KY-mock cell into which only vector was transferred.

Example 2

Preparation of a Cell Expressing Each of HNA-4a, HNA-4, HNA-5a and HNA-5b Antigens Each of the cDNAs of HNA-4a antigen, HNA-4b antigen, HNA-5a antigen and HNA-5b antigen was prepared from peripheral monocyte obtained from a healthy subject having a genotype of HNA-4a/a, HNA-4b/b, HNA-5a/a or HNA-5b/b, respectively. Specifically, whole RNA was extracted from each cell to synthesize cDNA by RT-PCR. The cDNA thus obtained was cloned into a commercially available plasmid pCR2.1-TOPO (Invitrogen, Carlsbad, Calif.) to confirm the DNA sequences of the CD11bMart(+) gene (which determines the polymorphism of HNA-4a), the CD11bMart(−) gene (which determines the polymorphism of HNA-4b), the CD11aOnd(+) gene (which determines the polymorphism of HNA-5a), the CD11aOnd(−) gene (which determines the polymorphism of HNA-5b), and the CD18 gene (which expresses commonly in HNA-4 and HNA-5). The cDNA and amino acid sequences of the CD11bMart(+) are listed in SEQ ID NOS: 7 and 8, respectively. The cDNA and amino acid sequences of the CD11bMart(−) are listed in SEQ ID NOS: 9 and 10, respectively. The cDNA and amino acid sequences of the CD11aOnd(+) are listed in SEQ ID NOS: 11 and 12, respectively. The cDNA and amino acid sequences of the CD11aOnd(−) are listed in SEQ ID NOS: 13 and 14, respectively. The cDNA and amino acid sequences of the CD18 are listed in SEQ ID NOS: 15 and 16, respectively.

Next, each cDNA of CD11bMart(+), CD11bMart(−), CD11aOnd(+) and CD11aOnd(−) was subcloned between the PacI site and the NotI site of the pQCXIP. The vectors were designated as pQCXIP-CD11bMart(+), pQCXIP-CD11bMart(−), pQCXIP-CD11aOnd(+) and pQCXIP-CD11aOnd(−), respectively. In addition, the cDNA of CD18 was subcloned between the PacI site and the NotI site of the commercially available retrovirus vector pQCXIN (different from pQCXIP in that the puromycin resistant gene has been replaced with the neomycin resistant gene, Becton Dickinson, San Jose, Calif.), and the vector was designated as pQCXIN-CD18. The structures of these vectors are shown in FIG. 1.

Next, pQCXIP-CD11bMart(+), pQCXIP-CD11bMart(−), pQCXIP-CD11aOnd(+) or pQCXIP-CD11aOnd(−) as well as pQCXIN-CD18 and pVSV-G (Becton Dickinson) were transfected into a gp-293T packaging cell strain (Becton Dickinson) by using Lipofetamine Plus reagent (Invitrogen) according to the standard protocol thereof. In this connection, another cell strain into which only pQCXIP or pQCXIN containing no HNA gene was also prepared in the similar procedure.

The gp-293T cell thus transfected was cultured for 48 hours to give a supernatant containing $10^5$ particles/ml of recombinant virus particles. To a 0.1 ml portion of the supernatant of the culture of the gp-293T cell into which pQCXIP-CD11bMart(+), pQCXIP-CD11bMart(−), pQCXIP-CD11aOnd(+) or pQCXIP-CD11aOnd(−) had been transfected was added 0.1 ml of supernatant of a gp-293T cell culture into which pQCXIN-CD18 had been transfected, followed by $1 \times 10^6$ cells of K562 cell suspended in 0.8 ml of a culture medium for infection (10% FBS-containing RPMI1640 medium supplemented with Polybrene at a final concentration of 8 µg/ml), and the mixture was cultured for 2 hours, washed twice with a R10 medium (10% FBS-containing RPMI1640 medium), and then cultured in a R10 medium for 2 days. Subsequently, the puromycin-resistant and neomycin-resistant cell among those which were infected with the recombinant virus was cloned by the limiting dilution method to give KY-4a cell, KY-4b cell, KY-5a cell and KY-5b cell which express HNA-4a, HNA-4b, HNA-5a and HNA-5b, respectively. The KY-mock pn into which only vectors (pQCXIP and pQCXIN) were transferred was also prepared.

Example 3

Analysis with Flow Cytometry (FCM)

(1) Examination of HNA Expression in KY-1a Cell and KY-1b Cell

KY-1a cell, KY-1b cell and KY-mock cell were incubated with FITC-TAG1 (monoclonal antibody against HNA-1a antigen) or FITC-TAG2 (monoclonal antibody against HNA-1b antigen) labeled with fluorescein (FITC) at 4° C. for 15 minutes. Then, the bonding of each cell and each antibody was examined by flow cytometry (FCM). The results are shown in FIG. 2.

Figure 2:
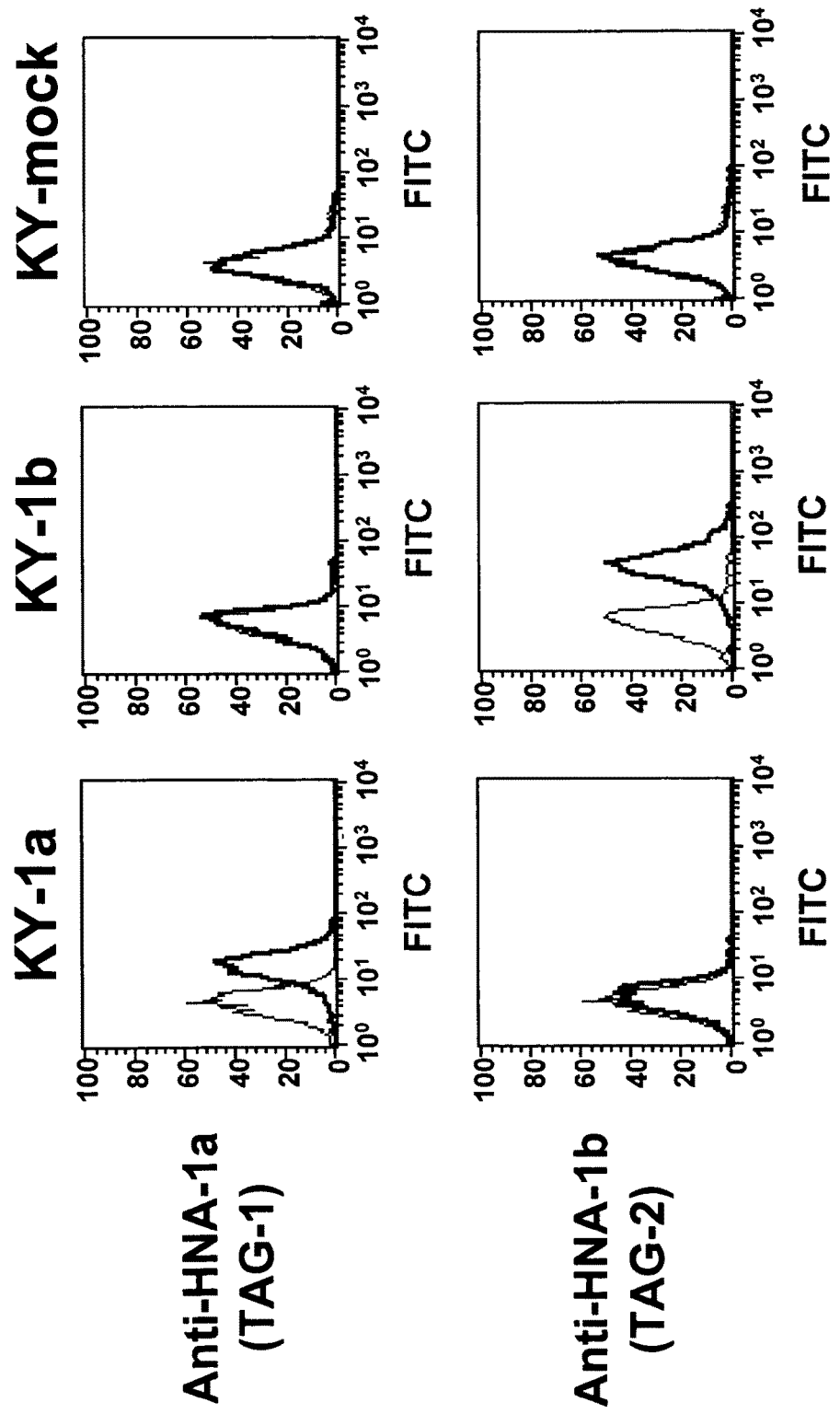
FIG. 2 shows the result of flow cytometry for the analysis of the HNA expression in KY-1a cell and KY-1b cell.

In each panel shown in FIG. 2, a graph obtained by using an antibody indicated in the left side and a graph obtained by using a mouse IgG as a control which has the same isotype are shown. When these two graphs are not completely overlapped, the left graph is the one obtained by using the mouse IgG. FIG. 2 illustrates that the KY-1a cell having the HNA-1a gene introduced thereto reacts only with the anti-HNA-1a antibody and thus specifically expresses the HNA-1a antigen. It is also shown that the KY-1b cell having the HNA-1b gene introduced thereto reacts only with the anti-HNA-1b antibody and thus specifically expresses the HNA-1b antigen. Non-specific reaction was not observed in the KY-mock cell as the control.

(2) Detection of Anti-HNA Antibody in Human Serum by Using KY-1a Cell and KY-1b Cell as a Panel Cell The reactivities of KY-1a cell, KY-1b cell and KY-mock cell with 10 anti-HLA antibody positive sera and 20 normal sera were examined by flow cytometry (FCM). As a result, neither of these cells reacts with these sera.

Next, reactivities of KY-1a cell, KY-1b cell and KY-mock cell with 2 sera containing an anti-HNA-1a antibody (anti-HNA-1a sera) or 3 sera containing an anti-HNA-1b antibody (one of the three sera also containing an anti-HLA class I antibody) (anti-HNA-1b sera) were examined by flow cytometry (FCM). The results are shown in FIGS. 3 and 4.

Figure 3:
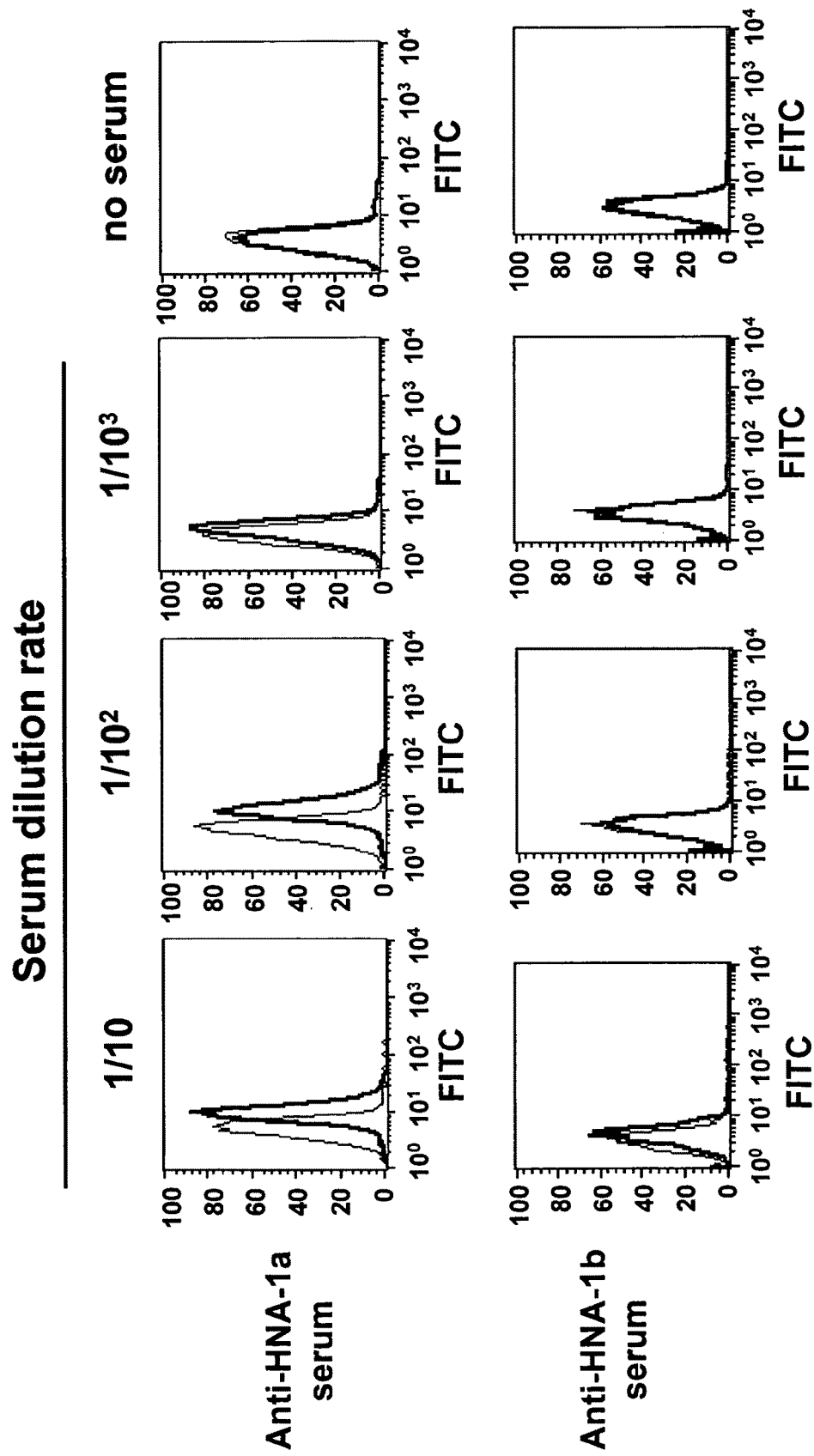
FIG. 3 shows the detection of the anti-HNA antibody in human serum by the flow cytometry using the KY-1a cell as a panel cell.

FIG. 3 illustrates the result with regard to the KY-1a cell. In each panel shown in FIG. 3, a graph obtained by using the KY-1a cell and a graph obtained by using the KY-mock cell as a control are shown. When these two graphs are not completely overlapped, the left graph is the one obtained by using the KY-mock cell. FIG. 3 illustrates that the KY-1a cell reacts only with the anti-HNA-1a serum and furthermore the intensity of the reaction depends on the concentration of the anti-HNA-1a antibody in the serum.

Figure 4:
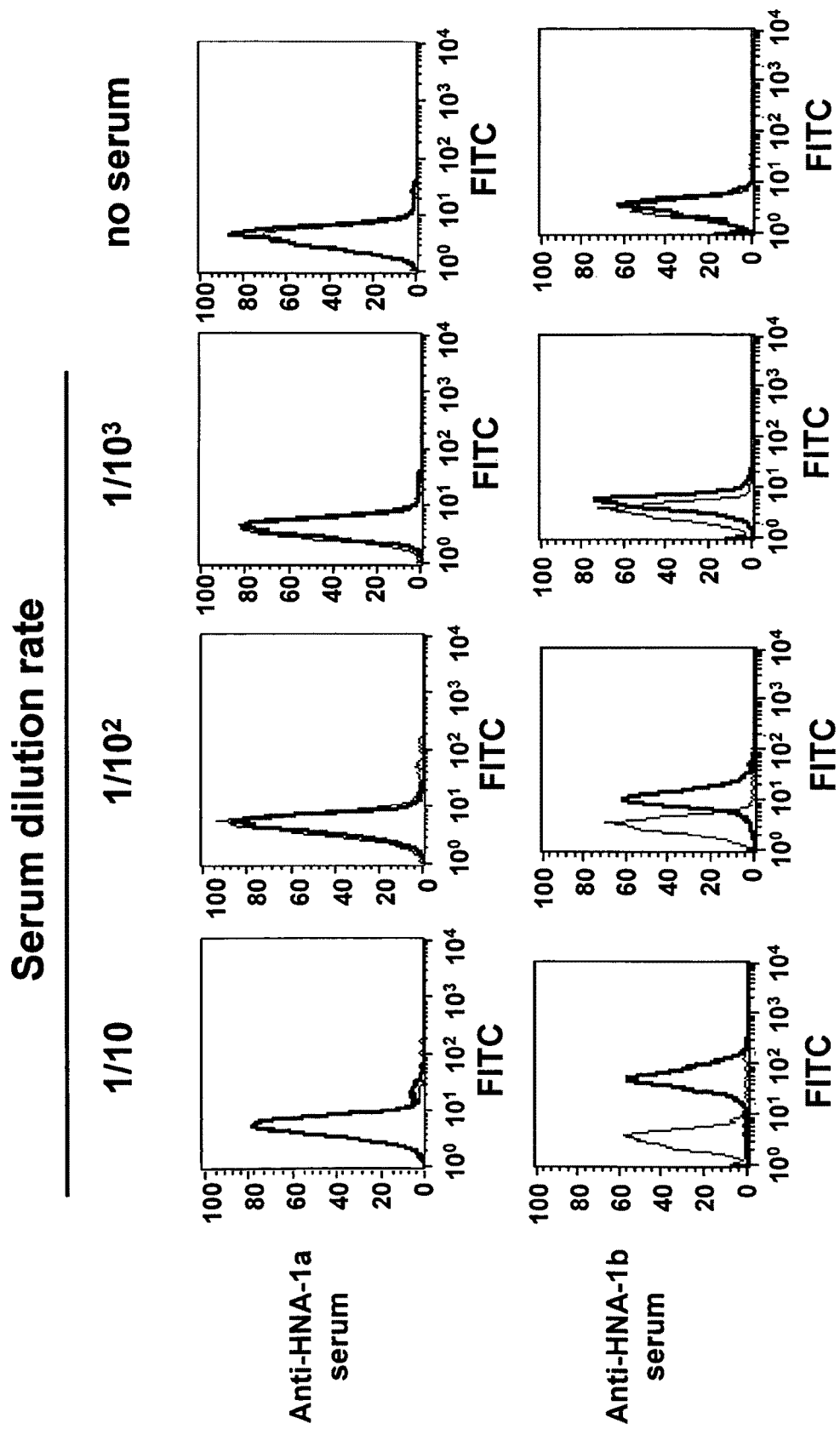
FIG. 4 shows the detection of the anti-HNA antibody in human serum by the flow cytometry using the KY-1b cell as a panel cell.

FIG. 4 illustrates the result with regard to the KY-1b cell. In each panel shown in FIG. 4, a graph obtained by using the KY-1b cell and a graph obtained by using the KY-mock cell as a control are shown. When these two graphs are not completely overlapped, the left graph is the one obtained by using the KY-mock cell. FIG. 4 illustrates that the KY-1b cell reacts only with the anti-HNA-1b serum and furthermore the intensity of the reaction depends on the concentration of the anti-HNA-1b antibody in the serum.

(3) Examination of HNK Expression in KY-2a Cell

KY-2a cell was incubated with FITC-TAG1, FITC-TAG2, FITC-TAG3 (monoclonal antibodies against HNA-1 antigen), FITC-TAG4 (monoclonal antibody against HNA-2a antigen) labeled with fluorescein (FITC) at 4° C. for 15 minutes. Then, the bonding of the KY-2a cell and each antibody was examined by flow cytometry (FCM). The results are shown in FIG. 5.

Figure 5:
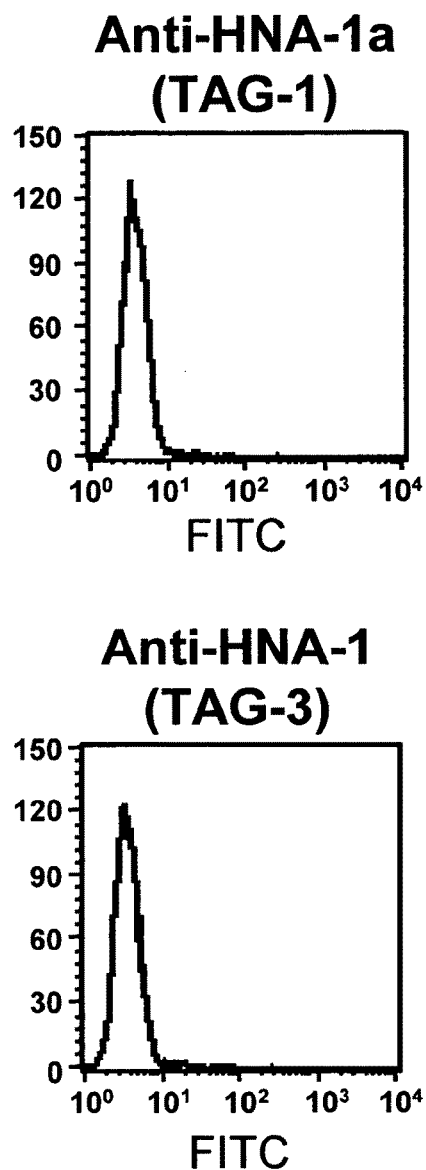
FIG. 5 shows the result of flow cytometry for the analysis of the HNA expression in KY-2a cell.
Figure 5:
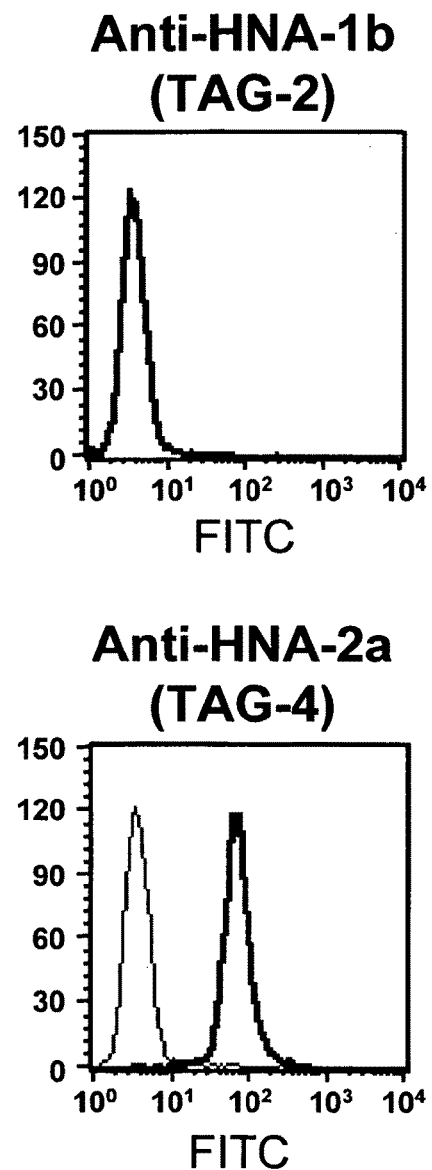
Figure 5:
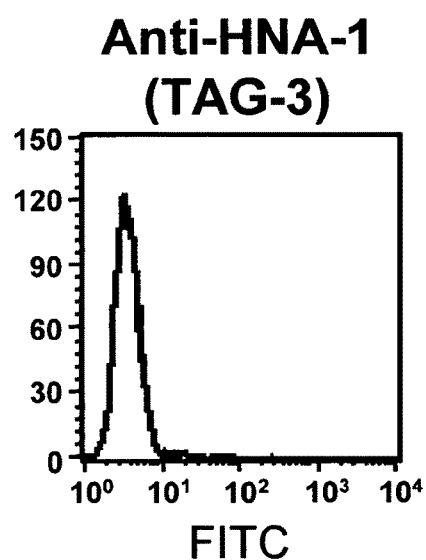
Figure 5:
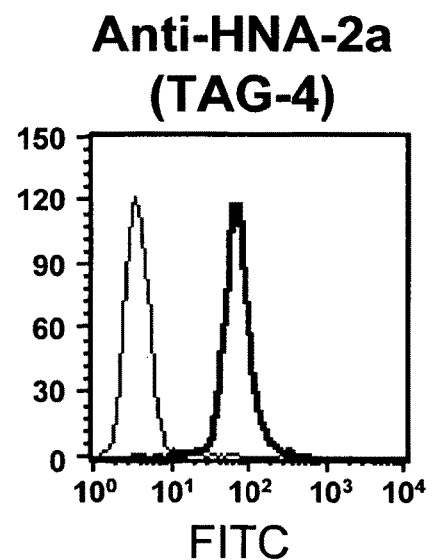

In each panel shown in FIG. 5, a graph obtained by using an antibody mentioned in the upper column and a graph obtained by using a mouse IgG as a control which has the same isotype are shown. When these two graphs are not completely overlapped, the left graph is the one obtained by using the mouse IgG. FIG. 5 illustrates that the KY-2a cell having the HNA-2a gene introduced thereto reacts only with the anti-HNA-2a antibody and thus specifically expresses the HNA-2a antigen.

(4) Detection of Anti-HNA Antibody in Human Serum by Using KY-2a Cell as a Panel Cell The reactivities of KY-2a cell with 10 anti-HLA antibody positive sera and 20 normal sera were examined by flow cytometry (FCM). As a result, the KY-2a cell did not react with these sera.

Next, reactivities of KY-2a cell and KY-mock cell with 2 anti-HNA-1a sera, 3 anti-HNA-1b sera, or 2 anti-HNA-2a antibody-containing sera (anti-HNA-2a sera) were examined by flow cytometry (FCM). The results are shown in FIG. 6.

Figure 6:
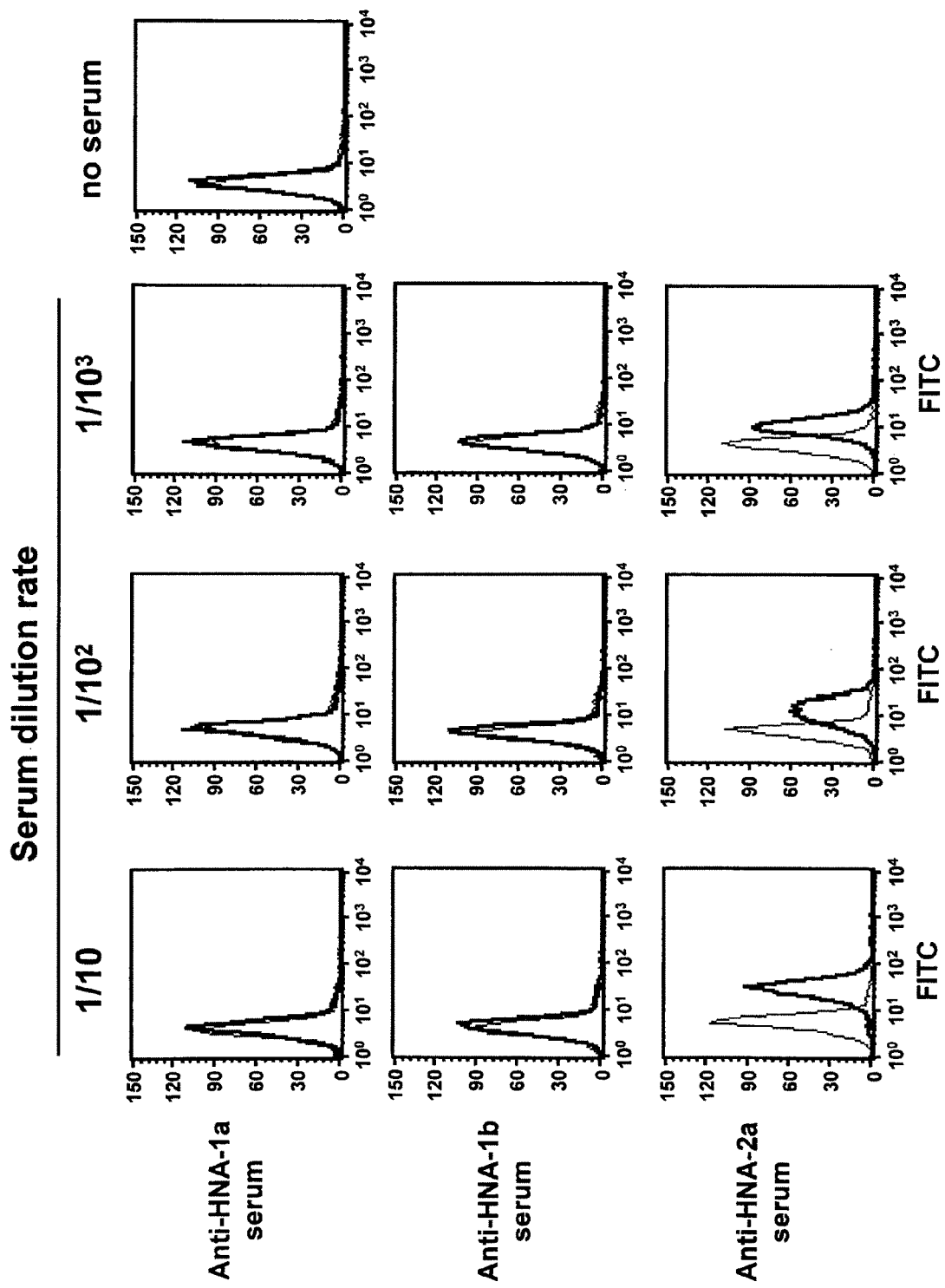
FIG. 6 shows the detection of the anti-HNA antibody in human serum by the flow cytometry using the KY-2a cell as a panel cell.

In each panel shown in FIG. 6, a graph obtained by using the KY-2a cell and a graph obtained by using the KY-mock cell as a control are shown. When these two graphs are not completely overlapped, the left graph is the one obtained by using the KY-mock cell. FIG. 6 illustrates that the KY-2a cell reacts only with the anti-HNA-2a serum and furthermore the intensity of the reaction depends on the concentration of the anti-HNA-2a antibody in the serum.

(5) Examination of HNA Expression in KY-4a Cell, KY-4b Cell, KY-5a Cell and KY-5b Cell KY-4a cell, KY-4b cell, KY-5a cell and KY-5b cell were incubated with FITC-CD11a antibody (monoclonal antibody against HNA-5 antigen) or FITC-CD11b antibody (monoclonal antibody against HNA-4 antigen) labeled with fluorescein isocyanate (FITC) and with CD18 antibody labeled with Phycoerythrin (PE) (HNA-4 antigen is a complex of CD11b and CD18, and HNA-5 antigen is a complex of CD11a and CD18. CD18 antibody is a monoclonal antibody against CD-18 common to HNA-4 antigen and HNA-5 antigen) at 4° C. for 15 minutes. Then, the bonding of each cell and each antibody was examined by flow cytometry (FCM). The results are shown in FIG. 7.

Figure 7:
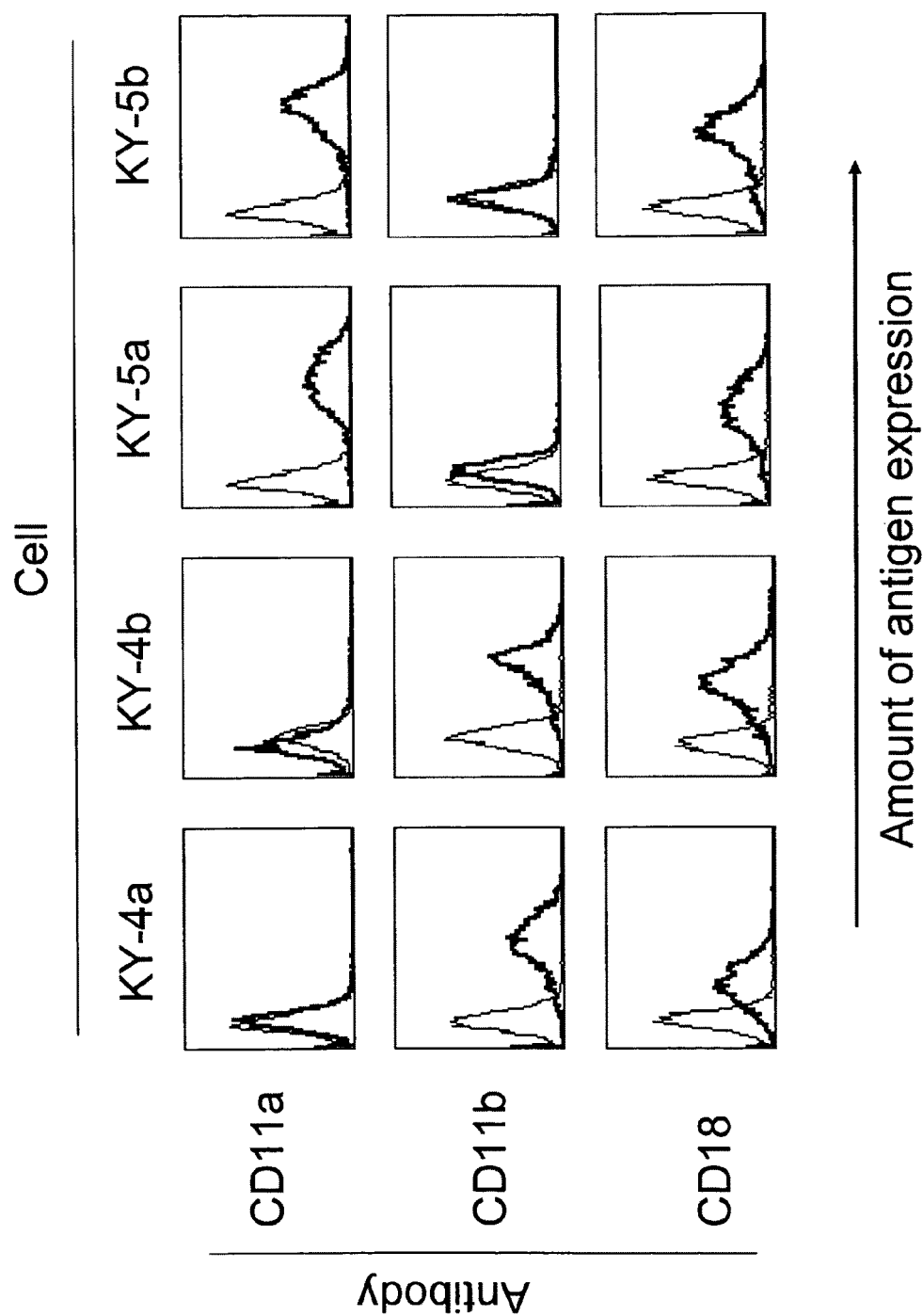
FIG. 7 shows the result of flow cytometry for the analysis of the HNA expression in KY-4a cell, KY-4b cell, KY-5a cell and KY-5b cell.

In each panel shown in FIG. 7, a histogram obtained by using an antibody indicated in the left side and a histogram obtained by using a mouse IgG as a control which has the same isotype are shown. When these two histograms are not completely overlapped, the left histogram is the one obtained by using the mouse IgG. FIG. 7 illustrates that the KY-4a cell having the HNA-4a gene introduced thereto or the KY-4b cell having the HNA-4b gene introduced thereto reacts only with the anti-HNA-4 antibody (CD11b) and thus specifically expresses the HNA-4a or HNA-4b antigen. It is also shown that the KY-5a cell having the HNA-5a gene introduced thereto or the KY-5b cell having the HNA-5b gene introduced thereto reacts only with the anti-HNA-5 antibody (CD11a) and thus specifically expresses the HNA-5a or HNA-5b antigen. The expression of a CD18 molecule common to the HNA-4 and HNA-5 antigens is also confirmed by the CD18 antibody.

Example 4

Stability of Antigen Expression in KY-1a Cell, KY-1b Cell and KY-2a Cell

The stabilities of the expression of gene (antigen expression) in KY-1a cell, KY-1b cell and KY-2a cell prepared in Example 1 were examined. Specifically, the aforementioned three cells were cultured in a R10 medium supplemented with puromycin at a final concentration of 0.5 µg/ml, and the expressions of the antigens in these cells were measured as a function of time by flow cytometry (FCM) using monoclonal antibodies against the antigens (FITC-TAG1, FITC-TAG2, and FITC-TAG4). High stability was observed with no change in the expression of the antigen in the KY-1a and KY-1b cells at 0, 1, 3 and 6 months after preparation. Also, the KY-2a cell has stably expressed the antigen up to 3 months after preparation.

Example 5

Confirmation of the Transgene Expression in KY-4a Cell, KY-4b Cell, KY-5a Cell and KY-5b Cell by RT-PCR The expression of the transgene in KY-4a cell, KY-4b cell, KY-5a cell and KY-5b cell prepared in Example 2 was examined by RT-PCR. Specifically, whole RNA was extracted from each cell to synthesize cDNA by RT-PCR, and nucleotide sequences containing the site which determines the polymorphism of HNA-4 (present on CD11b antigen) or HNA-5 (present on CD11a antigen) were amplified with specific primers to check the differences of the nucleotide sequences due to the polymorphisms by observing the fragmentation patterns obtained by restriction enzyme digestion.

Figure 8:
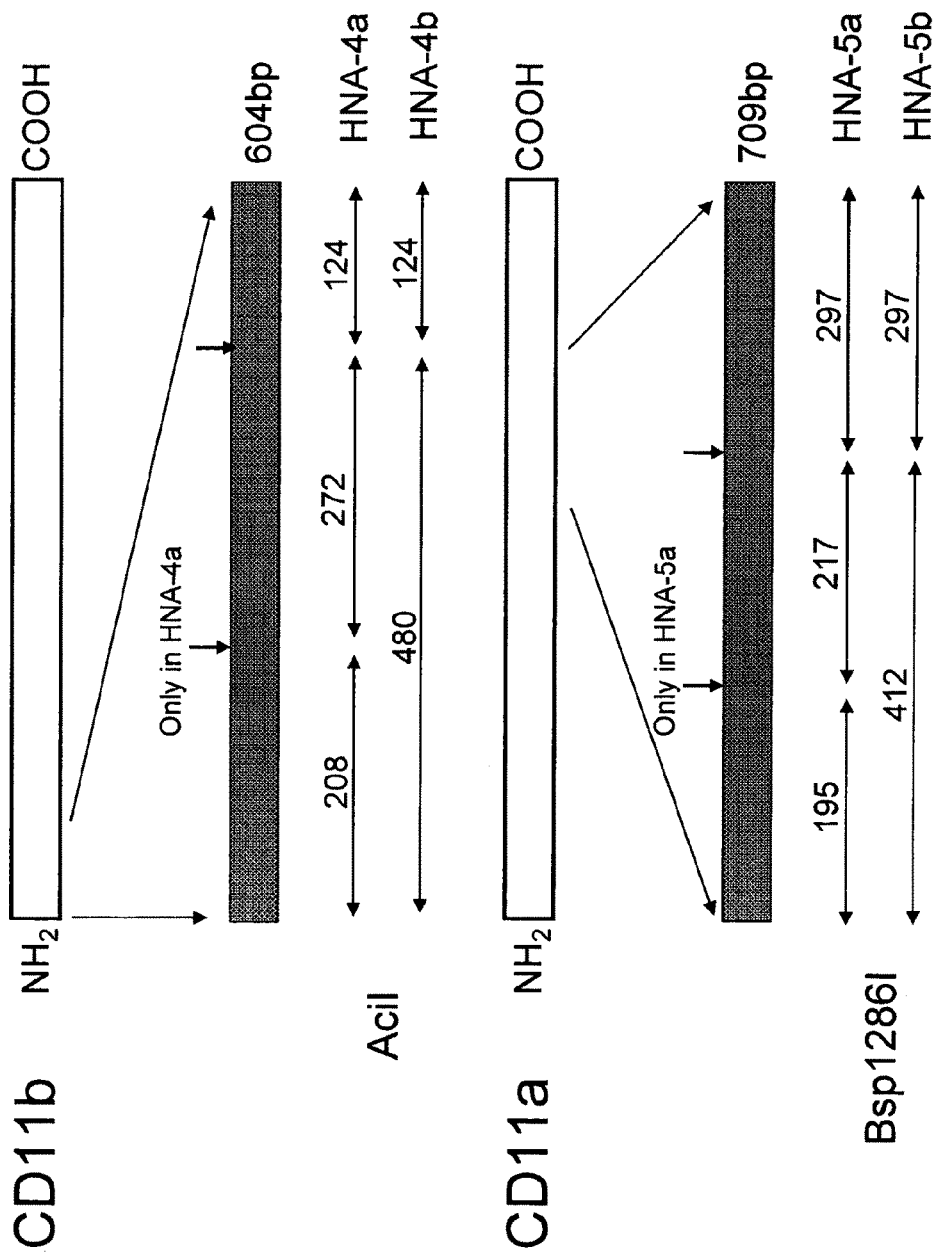
FIG. 8 shows the polymorphism of CD11a gene and CD11b gene.

As shown in FIG. 8, the gene coding for the HNA-4 antigen (CD11b) exhibits the polymorphism of the HNA-4a gene having two restriction sites of restriction enzyme AciI and the HNA-4b gene having only one restriction site of the same. The gene cording for the HNA-5 antigen (CD11a) exhibits the polymorphism of the HNA-5a gene having two restriction sites of restriction enzyme Bsp1286I and the HNA-5b gene having only one restriction site of the same. The product amplified by RT-PCR in each cell was digested by the restriction enzyme and subjected to electrophoresis. The results are shown in FIG. 9.

Figure 9:
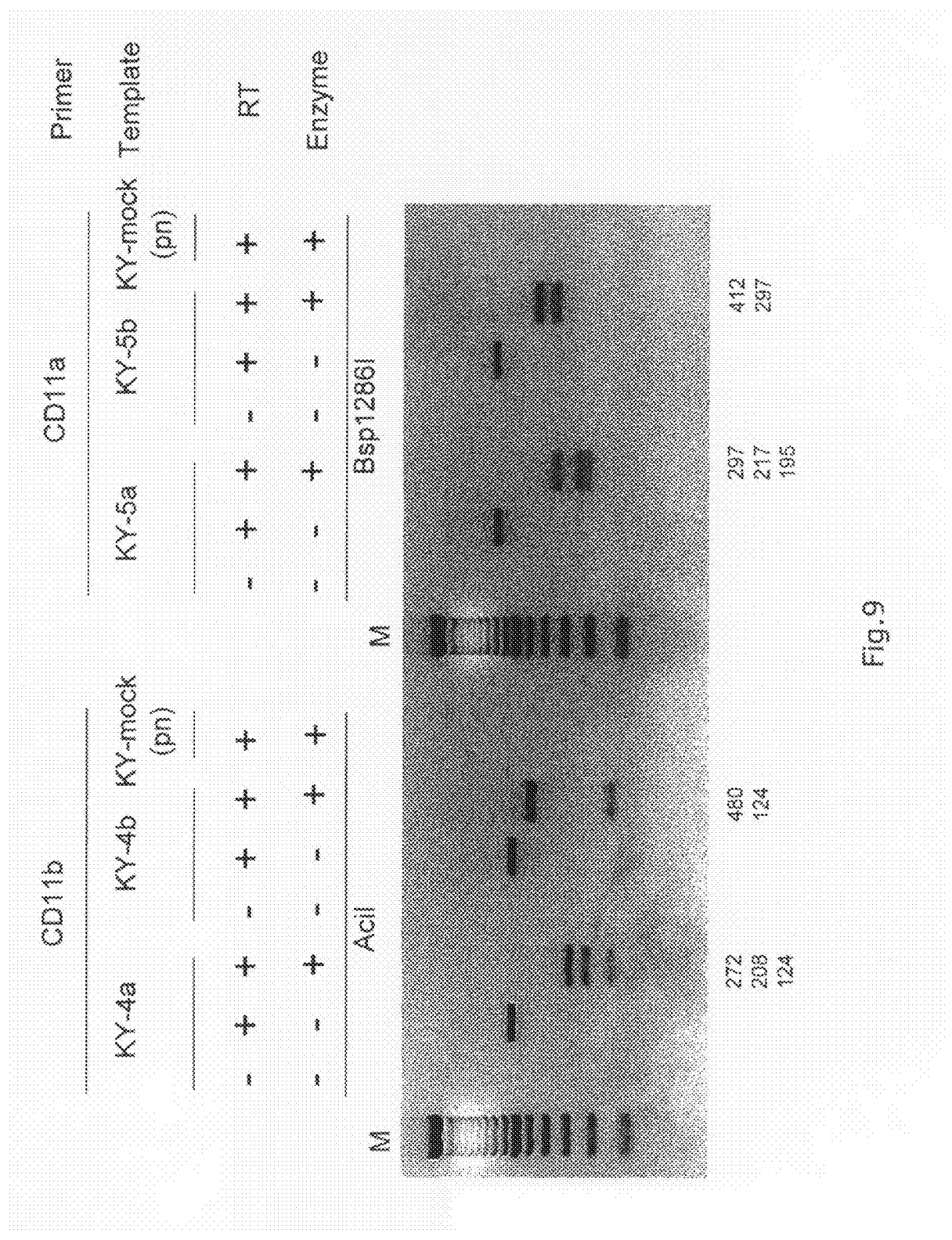
Figure 10:
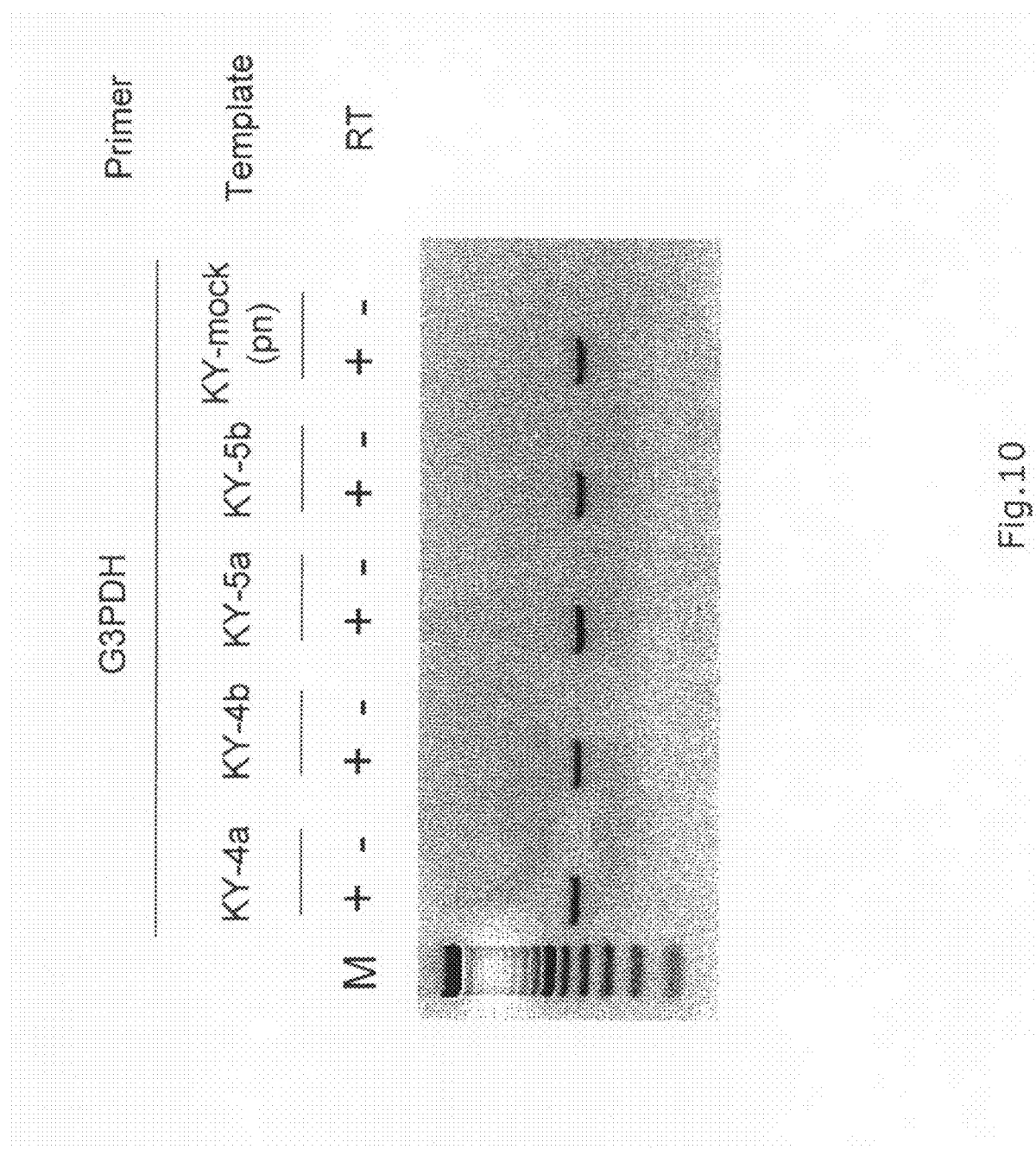
FIG. 10 is the electrophoresis photogram which shows the expression of a control gene (G3PDH) in KY-4a cell, KY-4b cell, KY-5a cell, KY-5b cell and KY-mock pn cell.

As shown in FIG. 9, PCR was carried out with primers which specifically amplify the polymorphismic site in a cDNA as a template synthesized from the KY-4a or KY-4b cell having the HNA-4a or HNA-4b gene introduced thereto. As a result, specific amplification products were observed (CD11b, RT+, enzyme−). These amplification products were not observed in PCR with the cDNA of KY-mock pn. Furthermore, when the amplification products were digested by restriction enzyme AciI, three bands corresponding to 272 bp, 208 bp and 124 bp (2 restriction sites) were observed in the KY-4a cell having HNA-4a gene introduced thereto, and two bands corresponding to 480 bp and 124 bp (1 restriction site) were observed in the KY-4b cell. This shows that the mRNA of the HNA-4a and HNA-4b genes specifically express in the KY-4a and KY-4b cells, respectively. The similar examination was carried out also with KY-5a and KY-5b cells, and the specific expression of the mRNA of the HNA-5a and HNA-5b genes, respectively, were observed. Furthermore, it is confirmed by checking the amount of expression of G3PDH that the amounts of whole RNA (amount of cDNA) were not different between the cells (FIG. 10).

The invention claimed is:

1. A method of detecting an anti-HNA antibody in a test sample, comprising the steps of:
   (a) providing a test sample,
   (b) providing a panel cell for detecting said anti-HNA antibody,
   which is obtained by introducing a DNA coding for an HNA antigen corresponding to said anti-HNA antibody into a cell so as to enable the expression of said DNA under the condition for use in the detection procedure, wherein the cell for DNA introduction is a K562 cell, and
   (c) bringing said test sample into contact with said panel cell, and detecting the binding of said panel cell with said anti-HNA antibody.

2. The method according to claim 1, wherein the panel cell is immobilized on a carrier.

3. The method according to claim 1, wherein the binding of the panel cell with the anti-HNA antibody is detected by flow cytometry.

4. The method according to claim 1, wherein the anti-HNA antibody is an anti-HNA-1a antibody, and the HNA antigen corresponding thereto is an HNA-1a antigen of the sequence of SEQ ID NO:2.

5. The method according to claim 1, wherein the anti-HNA antibody is an anti-HNA-1b antibody, and the HNA antigen corresponding thereto is an HNA-1b antigen of the sequence of SEQ ID NO:4.

6. The method according to claim 1, wherein the anti-HNA antibody is an anti-HNA-2a antibody, and the HNA antigen corresponding thereto is an HNA-2a antigen of the sequence of SEQ ID NO:6.

7. The method according to claim 1, wherein the anti-HNA antibody is an anti-HNA-4a antibody, and the HNA antigen corresponding thereto is an HNA-4a antigen of the sequence of SEQ ID NO:8 and SEQ ID NO:16.

8. The method according to claim 1, wherein the anti-HNA antibody is an anti-HNA-4b antibody, and the HNA antigen corresponding thereto is an HNA-4b antigen of the sequence of SEQ ID NO:10 and SEQ ID NO:16.

9. The method according to claim 1, wherein the anti-HNA antibody is an anti-HNA-5a antibody, and the HNA antigen corresponding thereto is an HNA-5a antigen of the sequence of SEQ ID NO:12 and SEQ ID NO:16.

10. The method according to claim 1, wherein the anti-HNA antibody is an anti-HNA-5b antibody, and the HNA antigen corresponding thereto is an HNA-5b antigen of the sequence of SEQ ID NO:14 and SEQ ID NO:16.

11. The method according to claim 1, wherein said DNA is incorporated into genome of said cell.

* * * * *

SEQUENCE LISTING

<160> NUMBER OF SEQ ID NOS: 16

<210> SEQ ID NO 1
<211> LENGTH: 887
<212> TYPE: DNA
<213> ORGANISM: Homo sapiens
<220> FEATURE:
<221> NAME/KEY: CDS
<222> LOCATION: (34)..(732)
<223> OTHER INFORMATION:

<400> SEQUENCE: 1

```
tctttggtga cttgtccact ccagtgtggc atc atg tgg cag ctg ctc ctc cca       54
                                    Met Trp Gln Leu Leu Leu Pro
                                    1               5 act gct ctg cta ctt cta gtt tca gct ggc atg cgg act gaa gat ctc       102
Thr Ala Leu Leu Leu Leu Val Ser Ala Gly Met Arg Thr Glu Asp Leu
            10                  15                  20 cca aag gct gtg gtg ttc ctg gag cct caa tgg tac agg gtg ctc gag       150
Pro Lys Ala Val Val Phe Leu Glu Pro Gln Trp Tyr Arg Val Leu Glu
        25                  30                  35 aag gac agt gtg act ctg aag tgc cag gga gcc tac tcc cct gag gac       198
Lys Asp Ser Val Thr Leu Lys Cys Gln Gly Ala Tyr Ser Pro Glu Asp
40                  45                  50                  55 aat tcc aca cag tgg ttt cac aat gag aac ctc atc tca agc cag gcc       246
Asn Ser Thr Gln Trp Phe His Asn Glu Asn Leu Ile Ser Ser Gln Ala
                60                  65                  70 tcg agc tac ttc att gac gct gcc aca gtc gac gac agt gga gag tac       294
Ser Ser Tyr Phe Ile Asp Ala Ala Thr Val Asp Asp Ser Gly Glu Tyr
            75                  80                  85 agg tgc cag aca aac ctc tcc acc ctc agt gac ccg gtg cag cta gaa       342
Arg Cys Gln Thr Asn Leu Ser Thr Leu Ser Asp Pro Val Gln Leu Glu
        90                  95                  100 gtc cat gtc ggc tgg ctg ttg ctc cag gcc cct cgg tgg gtg ttc aag       390
Val His Val Gly Trp Leu Leu Leu Gln Ala Pro Arg Trp Val Phe Lys
    105                 110                 115 gag gaa gac cct att cac ctg agg tgt cac agc tgg aag aac act gct       438
Glu Glu Asp Pro Ile His Leu Arg Cys His Ser Trp Lys Asn Thr Ala
120                 125                 130                 135 ctg cat aag gtc aca tat tta cag aat ggc aaa gac agg aag tat ttt       486
Leu His Lys Val Thr Tyr Leu Gln Asn Gly Lys Asp Arg Lys Tyr Phe
                140                 145                 150 cat cat aat tct gac ttc cac att cca aaa gcc aca ctc aaa gat agc       534
His His Asn Ser Asp Phe His Ile Pro Lys Ala Thr Leu Lys Asp Ser
            155                 160                 165 ggc tcc tac ttc tgc agg ggg ctt gtt ggg agt aaa aat gtg tct tca       582
Gly Ser Tyr Phe Cys Arg Gly Leu Val Gly Ser Lys Asn Val Ser Ser
        170                 175                 180 gag act gtg aac atc acc atc act caa ggt ttg gca gtg tca acc atc       630
Glu Thr Val Asn Ile Thr Ile Thr Gln Gly Leu Ala Val Ser Thr Ile
    185                 190                 195 tca tca ttc tct cca cct ggg tac caa gtc tct ttc tgc ttg gtg atg       678
Ser Ser Phe Ser Pro Pro Gly Tyr Gln Val Ser Phe Cys Leu Val Met
200                 205                 210                 215
```

```
gta ctc ctt ttt gca gtg gac aca gga cta tat ttc tct gtg aag aca    726
Val Leu Leu Phe Ala Val Asp Thr Gly Leu Tyr Phe Ser Val Lys Thr
            220                 225                 230 aac att tgaagctcaa caagagactg aaggaccat aaacttaaat ggagaaagga      782
Asn Ile ccctcaagac aaatgacccc catcccatgg gagtaataag agcagtggca gcagcatctc   842
tgaacatttc tctggatttg caaccccatc atcctcaggc ctctc                  887

<210> SEQ ID NO 2
<211> LENGTH: 233
<212> TYPE: PRT
<213> ORGANISM: Homo sapiens

<400> SEQUENCE: 2

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Asn Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Val Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230

<210> SEQ ID NO 3
<211> LENGTH: 887
<212> TYPE: DNA
<213> ORGANISM: Homo sapiens
<220> FEATURE:
<221> NAME/KEY: CDS
<222> LOCATION: (34)..(732)
<223> OTHER INFORMATION:

<400> SEQUENCE: 3
tctttggtga cttgtccact ccagtgtggc atc atg tgg cag ctg ctc ctc cca   54
                                  Met Trp Gln Leu Leu Leu Pro
                                  1               5
```

```
act gct ctg cta ctt cta gtt tca gct ggc atg cgg act gaa gat ctc    102
Thr Ala Leu Leu Leu Leu Val Ser Ala Gly Met Arg Thr Glu Asp Leu
        10                  15                  20 cca aag gct gtg gtg ttc ctg gag cct caa tgg tac agc gtg ctt gag    150
Pro Lys Ala Val Val Phe Leu Glu Pro Gln Trp Tyr Ser Val Leu Glu
    25                  30                  35 aag gac agt gtg act ctg aag tgc cag gga gcc tac tcc cct gag gac    198
Lys Asp Ser Val Thr Leu Lys Cys Gln Gly Ala Tyr Ser Pro Glu Asp
40                  45                  50                  55 aat tcc aca cag tgg ttt cac aat gag agc ctc atc tca agc cag gcc    246
Asn Ser Thr Gln Trp Phe His Asn Glu Ser Leu Ile Ser Ser Gln Ala
                60                  65                  70 tcg agc tac ttc att gac gct gcc aca gtc aac gac agt gga gag tac    294
Ser Ser Tyr Phe Ile Asp Ala Ala Thr Val Asn Asp Ser Gly Glu Tyr
            75                  80                  85 agg tgc cag aca aac ctc tcc acc ctc agt gac ccg gtg cag cta gaa    342
Arg Cys Gln Thr Asn Leu Ser Thr Leu Ser Asp Pro Val Gln Leu Glu
        90                  95                  100 gtc cat atc ggc tgg ctg ttg ctc cag gcc cct cgg tgg gtg ttc aag    390
Val His Ile Gly Trp Leu Leu Leu Gln Ala Pro Arg Trp Val Phe Lys
    105                 110                 115 gag gaa gac cct att cac ctg agg tgt cac agc tgg aag aac act gct    438
Glu Glu Asp Pro Ile His Leu Arg Cys His Ser Trp Lys Asn Thr Ala
120                 125                 130                 135 ctg cat aag gtc aca tat tta cag aat ggc aaa gac agg aag tat ttt    486
Leu His Lys Val Thr Tyr Leu Gln Asn Gly Lys Asp Arg Lys Tyr Phe
                140                 145                 150 cat cat aat tct gac ttc cac att cca aaa gcc aca ctc aaa gat agc    534
His His Asn Ser Asp Phe His Ile Pro Lys Ala Thr Leu Lys Asp Ser
            155                 160                 165 ggc tcc tac ttc tgc agg ggg ctt gtt ggg agt aaa aat gtg tct tca    582
Gly Ser Tyr Phe Cys Arg Gly Leu Val Gly Ser Lys Asn Val Ser Ser
        170                 175                 180 gag act gtg aac atc acc atc act caa ggt ttg gca gtg tca acc atc    630
Glu Thr Val Asn Ile Thr Ile Thr Gln Gly Leu Ala Val Ser Thr Ile
    185                 190                 195 tca tca ttc tct cca cct ggg tac caa gtc tct ttc tgc ttg gtg atg    678
Ser Ser Phe Ser Pro Pro Gly Tyr Gln Val Ser Phe Cys Leu Val Met
200                 205                 210                 215 gta ctc ctt ttt gca gtg gac aca gga cta tat ttc tct gtg aag aca    726
Val Leu Leu Phe Ala Val Asp Thr Gly Leu Tyr Phe Ser Val Lys Thr
                220                 225                 230 aac att tgaagctcaa caagagactg aaggaccat  aaacttaaat ggagaaagga    782
Asn Ile ccctcaagac aaatgacccc catcccatgg gagtaataag agcagtggca gcagcatctc    842
tgaacatttc tctggatttg caaccccatc atcctcaggc ctctc                    887

<210> SEQ ID NO 4
<211> LENGTH: 233
<212> TYPE: PRT
<213> ORGANISM: Homo sapiens

<400> SEQUENCE: 4

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45
```

```
Gly Ala Tyr Ser Pro Glu Asp Asn Ser Thr Gln Trp Phe His Asn Glu
    50                  55                  60
Ser Leu Ile Ser Ser Gln Ala Ser Ser Tyr Phe Ile Asp Ala Ala Thr
65                  70                  75                  80
Val Asn Asp Ser Gly Glu Tyr Arg Cys Gln Thr Asn Leu Ser Thr Leu
                85                  90                  95
Ser Asp Pro Val Gln Leu Glu Val His Ile Gly Trp Leu Leu Leu Gln
            100                 105                 110
Ala Pro Arg Trp Val Phe Lys Glu Glu Asp Pro Ile His Leu Arg Cys
        115                 120                 125
His Ser Trp Lys Asn Thr Ala Leu His Lys Val Thr Tyr Leu Gln Asn
    130                 135                 140
Gly Lys Asp Arg Lys Tyr Phe His His Asn Ser Asp Phe His Ile Pro
145                 150                 155                 160
Lys Ala Thr Leu Lys Asp Ser Gly Ser Tyr Phe Cys Arg Gly Leu Val
                165                 170                 175
Gly Ser Lys Asn Val Ser Ser Glu Thr Val Asn Ile Thr Ile Thr Gln
            180                 185                 190
Gly Leu Ala Val Ser Thr Ile Ser Ser Phe Ser Pro Pro Gly Tyr Gln
        195                 200                 205
Val Ser Phe Cys Leu Val Met Val Leu Leu Phe Ala Val Asp Thr Gly
    210                 215                 220
Leu Tyr Phe Ser Val Lys Thr Asn Ile
225                 230

<210> SEQ ID NO 5
<211> LENGTH: 1630
<212> TYPE: DNA
<213> ORGANISM: Homo sapiens
<220> FEATURE:
<221> NAME/KEY: CDS
<222> LOCATION: (36)..(1346)
<223> OTHER INFORMATION:

<400> SEQUENCE: 5
aaaagcagaa agagattacc agccacagac gggtc atg agc gcg gta tta ctg        53
                                      Met Ser Ala Val Leu Leu
                                      1               5 ctg gcc ctc ctg ggg ttc atc ctc cca ctg cca gga gtg cag gcg ctg      101
Leu Ala Leu Leu Gly Phe Ile Leu Pro Leu Pro Gly Val Gln Ala Leu
                10                  15                  20 ctc tgc cag ttt ggg aca gtt cag cat gtg tgg aag gtg tcc gac ctg      149
Leu Cys Gln Phe Gly Thr Val Gln His Val Trp Lys Val Ser Asp Leu
            25                  30                  35 ccc cgg caa tgg acc cct aag aac acc agc tgc gac agc ggc ttg ggg      197
Pro Arg Gln Trp Thr Pro Lys Asn Thr Ser Cys Asp Ser Gly Leu Gly
        40                  45                  50 tgc cag gac acg ttg atg ctc att gag agc gga ccc caa gtg agc ctg      245
Cys Gln Asp Thr Leu Met Leu Ile Glu Ser Gly Pro Gln Val Ser Leu
55                  60                  65                  70 gtg ctc tcc aag ggc tgc acg gag gcc aag gac cag gag ccc gcg tc       293
Val Leu Ser Lys Gly Cys Thr Glu Ala Lys Asp Gln Glu Pro Arg Val
                75                  80                  85 act gag cac cgg atg ggc ccc ggc ctc tcc ctg atc tcc tac acc ttc      341
Thr Glu His Arg Met Gly Pro Gly Leu Ser Leu Ile Ser Tyr Thr Phe
            90                  95                 100 gtg tgc cgc cag gag gac ttc tgc aac aac ctc gtt aac tcc ctc ccg      389
Val Cys Arg Gln Glu Asp Phe Cys Asn Asn Leu Val Asn Ser Leu Pro
        105                 110                 115
```

| | | |
|---|---|---|
| ctt tgg gcc cca cag ccc cca gca gac cca gga tcc ttg agg tgc cca | | 437 |
| Leu Trp Ala Pro Gln Pro Pro Ala Asp Pro Gly Ser Leu Arg Cys Pro | | |
| 120 125 130 | | |
| gtc tgc ttg tct atg gaa ggc tgt ctg gag ggg aca aca gaa gag atc | | 485 |
| Val Cys Leu Ser Met Glu Gly Cys Leu Glu Gly Thr Thr Glu Glu Ile | | |
| 135 140 145 150 | | |
| tgc ccc aag ggg acc aca cac tgt tat gat ggc ctc ctc agg ctc agg | | 533 |
| Cys Pro Lys Gly Thr Thr His Cys Tyr Asp Gly Leu Leu Arg Leu Arg | | |
| 155 160 165 | | |
| gga ggc ggc atc ttc tcc aat ctg aga gtc cag gga tgc atg ccc cag | | 581 |
| Gly Gly Gly Ile Phe Ser Asn Leu Arg Val Gln Gly Cys Met Pro Gln | | |
| 170 175 180 | | |
| cca ggt tgc aac ctg ctc aat ggg aca cag gaa att ggg ccc gtg ggt | | 629 |
| Pro Gly Cys Asn Leu Leu Asn Gly Thr Gln Glu Ile Gly Pro Val Gly | | |
| 185 190 195 | | |
| atg act gag aac tgc aat agg aaa gat ttt ctg acc tgt cat cgg ggg | | 677 |
| Met Thr Glu Asn Cys Asn Arg Lys Asp Phe Leu Thr Cys His Arg Gly | | |
| 200 205 210 | | |
| acc acc att atg aca cac gga aac ttg gct caa gaa ccc act gat tgg | | 725 |
| Thr Thr Ile Met Thr His Gly Asn Leu Ala Gln Glu Pro Thr Asp Trp | | |
| 215 220 225 230 | | |
| acc aca tcg aat acc gag atg tgc gag gtg ggg cag gtg tgt cag gag | | 773 |
| Thr Thr Ser Asn Thr Glu Met Cys Glu Val Gly Gln Val Cys Gln Glu | | |
| 235 240 245 | | |
| acg ctg ctc ctc ata gat gta gga ctc aca tca acc ctg gtg ggg aca | | 821 |
| Thr Leu Leu Leu Ile Asp Val Gly Leu Thr Ser Thr Leu Val Gly Thr | | |
| 250 255 260 | | |
| aaa ggc tgc agc act gtt ggg gct caa aat tcc cag aag acc acc atc | | 869 |
| Lys Gly Cys Ser Thr Val Gly Ala Gln Asn Ser Gln Lys Thr Thr Ile | | |
| 265 270 275 | | |
| cac tca gcc cct cct ggg gtg ctt gtg gcc tcc tat acc cac ttc tgc | | 917 |
| His Ser Ala Pro Pro Gly Val Leu Val Ala Ser Tyr Thr His Phe Cys | | |
| 280 285 290 | | |
| tcc tcg gac ctg tgc aat agt gcc agc agc agc agc gtt ctg ctg aac | | 965 |
| Ser Ser Asp Leu Cys Asn Ser Ala Ser Ser Ser Ser Val Leu Leu Asn | | |
| 295 300 305 310 | | |
| tcc ctc cct cct caa gct gcc cct gtc cca gga gac cgg cag tgt cct | | 1013 |
| Ser Leu Pro Pro Gln Ala Ala Pro Val Pro Gly Asp Arg Gln Cys Pro | | |
| 315 320 325 | | |
| acc tgt gtg cag ccc ctt gga acc tgt tca agt ggc tcc ccc cga atg | | 1061 |
| Thr Cys Val Gln Pro Leu Gly Thr Cys Ser Ser Gly Ser Pro Arg Met | | |
| 330 335 340 | | |
| acc tgc ccc agg ggc gcc act cat tgt tat gat ggg tac att cat ctc | | 1109 |
| Thr Cys Pro Arg Gly Ala Thr His Cys Tyr Asp Gly Tyr Ile His Leu | | |
| 345 350 355 | | |
| tca gga ggt ggg ctg tcc acc aaa atg agc att cag ggc tgc gtg gcc | | 1157 |
| Ser Gly Gly Gly Leu Ser Thr Lys Met Ser Ile Gln Gly Cys Val Ala | | |
| 360 365 370 | | |
| caa cct tcc agc ttc ttg ttg aac cac acc aga caa atc ggg atc ttc | | 1205 |
| Gln Pro Ser Ser Phe Leu Leu Asn His Thr Arg Gln Ile Gly Ile Phe | | |
| 375 380 385 390 | | |
| tct gcg cgt gag aag cgt gat gtg cag cct cct gcc tct cag cat gag | | 1253 |
| Ser Ala Arg Glu Lys Arg Asp Val Gln Pro Pro Ala Ser Gln His Glu | | |
| 395 400 405 | | |
| gga ggt ggg gct gag ggc ctg gag tct ctc act tgg ggg gtg ggg ctg | | 1301 |
| Gly Gly Gly Ala Glu Gly Leu Glu Ser Leu Thr Trp Gly Val Gly Leu | | |
| 410 415 420 | | |
| gca ctg gcc cca gcg ctg tgg tgg gga gtg gtt tgc cct tcc tgc | | 1346 |
| Ala Leu Ala Pro Ala Leu Trp Trp Gly Val Val Cys Pro Ser Cys | | |
| 425 430 435 | | |

```
taactctatt accccacga ttcttcaccg ctgctgacca cccacactca acctccctct    1406
gacctcataa cctaatggcc ttggacacca gattctttcc cattctgtcc atgaatcatc    1466
ttccccacac acaatcattc atatctactc acctaacagc aacactgggg agagcctgga    1526
gcatccggac ttgccctatg ggagagggga cgctggagga rtggctgcat gtatctgata    1586
atacagaccc tgtcctttca aaaaaaaaaa aaaaaaaaa aaaa                      1630
```

<210> SEQ ID NO 6
<211> LENGTH: 437
<212> TYPE: PRT
<213> ORGANISM: Homo sapiens
<400> SEQUENCE: 6

```
Met Ser Ala Val Leu Leu Ala Leu Leu Gly Phe Ile Leu Pro Leu
1               5                  10                 15

Pro Gly Val Gln Ala Leu Leu Cys Gln Phe Gly Thr Val Gln His Val
            20                  25                  30

Trp Lys Val Ser Asp Leu Pro Arg Gln Trp Thr Pro Lys Asn Thr Ser
        35                  40                  45

Cys Asp Ser Gly Leu Gly Cys Gln Asp Thr Leu Met Leu Ile Glu Ser
    50                  55                  60

Gly Pro Gln Val Ser Leu Val Leu Ser Lys Gly Cys Thr Glu Ala Lys
65                  70                  75                  80

Asp Gln Glu Pro Arg Val Thr Glu His Arg Met Gly Pro Gly Leu Ser
                85                  90                  95

Leu Ile Ser Tyr Thr Phe Val Cys Arg Gln Glu Asp Phe Cys Asn Asn
            100                 105                 110

Leu Val Asn Ser Leu Pro Leu Trp Ala Pro Gln Pro Ala Asp Pro
        115                 120                 125

Gly Ser Leu Arg Cys Pro Val Cys Leu Ser Met Glu Gly Cys Leu Glu
    130                 135                 140

Gly Thr Thr Glu Glu Ile Cys Pro Lys Gly Thr Thr His Cys Tyr Asp
145                 150                 155                 160

Gly Leu Leu Arg Leu Arg Gly Gly Gly Ile Phe Ser Asn Leu Arg Val
                165                 170                 175

Gln Gly Cys Met Pro Gln Pro Cys Asn Leu Leu Asn Gly Thr Gln
            180                 185                 190

Glu Ile Gly Pro Val Gly Met Thr Glu Asn Cys Asn Arg Lys Asp Phe
        195                 200                 205

Leu Thr Cys His Arg Gly Thr Thr Ile Met Thr His Gly Asn Leu Ala
    210                 215                 220

Gln Glu Pro Thr Asp Trp Thr Thr Ser Asn Thr Glu Met Cys Glu Val
225                 230                 235                 240

Gly Gln Val Cys Gln Glu Thr Leu Leu Leu Ile Asp Val Gly Leu Thr
                245                 250                 255

Ser Thr Leu Val Gly Thr Lys Gly Cys Ser Thr Val Gly Ala Gln Asn
            260                 265                 270

Ser Gln Lys Thr Thr Ile His Ser Ala Pro Pro Gly Val Leu Val Ala
        275                 280                 285

Ser Tyr Thr His Phe Cys Ser Asp Leu Cys Asn Ser Ala Ser Ser
    290                 295                 300

Ser Ser Val Leu Leu Asn Ser Leu Pro Pro Gln Ala Ala Pro Val Pro
305                 310                 315                 320

Gly Asp Arg Gln Cys Pro Thr Cys Val Gln Pro Leu Gly Thr Cys Ser
```

```
                         325                 330                 335
Ser Gly Ser Pro Arg Met Thr Cys Pro Arg Gly Ala Thr His Cys Tyr
                340                 345                 350

Asp Gly Tyr Ile His Leu Ser Gly Gly Leu Ser Thr Lys Met Ser
            355                 360                 365

Ile Gln Gly Cys Val Ala Gln Pro Ser Ser Phe Leu Leu Asn His Thr
    370                 375                 380

Arg Gln Ile Gly Ile Phe Ser Ala Arg Glu Lys Arg Asp Val Gln Pro
385                 390                 395                 400

Pro Ala Ser Gln His Glu Gly Gly Ala Glu Gly Leu Glu Ser Leu
                405                 410                 415

Thr Trp Gly Val Gly Leu Ala Leu Ala Pro Ala Leu Trp Trp Gly Val
                420                 425                 430

Val Cys Pro Ser Cys
            435

<210> SEQ ID NO 7
<211> LENGTH: 3833
<212> TYPE: DNA
<213> ORGANISM: Homo sapiens
<220> FEATURE:
<221> NAME/KEY: CDS
<222> LOCATION: (94)..(3603)
<223> OTHER INFORMATION:

<400> SEQUENCE: 7
taatacgact cactataggg agacccaagc tggctagtta agctatcaac aagtttgtac      60
aaaaaagcag ctccgcggc cgccccttc acc atg aag gat tcc tgc atc act      114
                                   Met Lys Asp Ser Cys Ile Thr
                                   1               5 gtg atg gcc atg gcg ctg ctg tct ggg ttc ttt ttc ttc gcg ccg gcc      162
Val Met Ala Met Ala Leu Leu Ser Gly Phe Phe Phe Phe Ala Pro Ala
        10                  15                  20 tcg agc tac aac ctg gac gtg cgg ggc gcg cgg agc ttc tcc cca ccg      210
Ser Ser Tyr Asn Leu Asp Val Arg Gly Ala Arg Ser Phe Ser Pro Pro
    25                  30                  35 cgc gcc ggg agg cac ttt gga tac cgc gtc ctg cag gtc gga aac ggg      258
Arg Ala Gly Arg His Phe Gly Tyr Arg Val Leu Gln Val Gly Asn Gly
40                  45                  50                  55 gtc atc gtg gga gct cca ggg gag ggg aac agc aca gga agc ctc tat      306
Val Ile Val Gly Ala Pro Gly Glu Gly Asn Ser Thr Gly Ser Leu Tyr
                60                  65                  70 cag tgc cag tcg ggc aca gga cac tgc ctg cca gtc acc ctg aga ggt      354
Gln Cys Gln Ser Gly Thr Gly His Cys Leu Pro Val Thr Leu Arg Gly
            75                  80                  85 tcc aac tat acc tcc aag tac ttg gga atg acc ttg gca aca gac ccc      402
Ser Asn Tyr Thr Ser Lys Tyr Leu Gly Met Thr Leu Ala Thr Asp Pro
        90                  95                 100 aca gat gga agc att ttg gcc tgt gac cct ggg ctg tct cga acg tgt      450
Thr Asp Gly Ser Ile Leu Ala Cys Asp Pro Gly Leu Ser Arg Thr Cys
    105                 110                 115 gac cag aac acc tat ctg agt ggc ctg tgt tac ctc ttc cgc cag aat      498
Asp Gln Asn Thr Tyr Leu Ser Gly Leu Cys Tyr Leu Phe Arg Gln Asn
120                 125                 130                 135 ctg cag ggt ccc atg ctg cag ggg cgc cct ggt ttt cag gaa tgt atc      546
Leu Gln Gly Pro Met Leu Gln Gly Arg Pro Gly Phe Gln Glu Cys Ile
                140                 145                 150 aag ggc aac gta gac ctg gta ttt ctg ttt gat ggt tcg atg agc ttg      594
Lys Gly Asn Val Asp Leu Val Phe Leu Phe Asp Gly Ser Met Ser Leu
            155                 160                 165
```

```
cag cca gat gaa ttt cag aaa att ctg gac ttc atg aag gat gtg atg      642
Gln Pro Asp Glu Phe Gln Lys Ile Leu Asp Phe Met Lys Asp Val Met
        170                 175                 180 aag aaa ctc agc aac act tcg tac cag ttt gct gct gtt cag ttt tcc      690
Lys Lys Leu Ser Asn Thr Ser Tyr Gln Phe Ala Ala Val Gln Phe Ser
    185                 190                 195 aca agc tac aaa aca gaa ttt gat ttc tca gat tat gtt aaa cgg aag      738
Thr Ser Tyr Lys Thr Glu Phe Asp Phe Ser Asp Tyr Val Lys Arg Lys
200                 205                 210                 215 gac cct gat gct ctg ctg aag cat gta aag cac atg ttg ctg ttg acc      786
Asp Pro Asp Ala Leu Leu Lys His Val Lys His Met Leu Leu Leu Thr
                220                 225                 230 aat acc ttt ggt gcc atc aat tat gtc gcg aca gag gtg ttc cgg gag      834
Asn Thr Phe Gly Ala Ile Asn Tyr Val Ala Thr Glu Val Phe Arg Glu
            235                 240                 245 gag ctg ggg gcc cgg cca gat gcc acc aaa gtg ctt atc atc atc acg      882
Glu Leu Gly Ala Arg Pro Asp Ala Thr Lys Val Leu Ile Ile Ile Thr
        250                 255                 260 gat ggg gag gcc act gac agt ggc aac atc gat gcg gcc aaa gac atc      930
Asp Gly Glu Ala Thr Asp Ser Gly Asn Ile Asp Ala Ala Lys Asp Ile
    265                 270                 275 atc cgc tac atc atc ggg att gga aag cat ttt cag acc aag gag agt      978
Ile Arg Tyr Ile Ile Gly Ile Gly Lys His Phe Gln Thr Lys Glu Ser
280                 285                 290                 295 cag gag acc ctc cac aaa ttt gca tca aaa ccc gcg agc gag ttt gtg     1026
Gln Glu Thr Leu His Lys Phe Ala Ser Lys Pro Ala Ser Glu Phe Val
                300                 305                 310 aaa att ctg gac aca ttt gag aag ctg aaa gat cta ttc act gag ctg     1074
Lys Ile Leu Asp Thr Phe Glu Lys Leu Lys Asp Leu Phe Thr Glu Leu
            315                 320                 325 cag aag aag atc tat gtc att gag ggc aca agc aaa cag gac ctg act     1122
Gln Lys Lys Ile Tyr Val Ile Glu Gly Thr Ser Lys Gln Asp Leu Thr
        330                 335                 340 tcc ttc aac atg gag ctg tcc tcc agc ggc atc agt gct gac ctc agc     1170
Ser Phe Asn Met Glu Leu Ser Ser Ser Gly Ile Ser Ala Asp Leu Ser
    345                 350                 355 agg ggc cat gca gtc gtg ggg gca gta gga gcc aag gac tgg gct ggg     1218
Arg Gly His Ala Val Val Gly Ala Val Gly Ala Lys Asp Trp Ala Gly
360                 365                 370                 375 ggc ttt ctt gac ctg aag gca gac ctg cag gat gac aca ttt att ggg     1266
Gly Phe Leu Asp Leu Lys Ala Asp Leu Gln Asp Asp Thr Phe Ile Gly
                380                 385                 390 aat gaa cca ttg aca cca gaa gtg aga gca ggc tat ttg ggt tac acc     1314
Asn Glu Pro Leu Thr Pro Glu Val Arg Ala Gly Tyr Leu Gly Tyr Thr
            395                 400                 405 gtg acc tgg ctg ccc tcc cgg caa aag act tcg ttg ctg gcc tcg gga     1362
Val Thr Trp Leu Pro Ser Arg Gln Lys Thr Ser Leu Leu Ala Ser Gly
        410                 415                 420 gcc cct cga tac cag cac atg ggc cga gtg ctg ctg ttc caa gag cca     1410
Ala Pro Arg Tyr Gln His Met Gly Arg Val Leu Leu Phe Gln Glu Pro
    425                 430                 435 cag ggc gga gga cac tgg agc cag gtc cag aca atc cat ggg acc cag     1458
Gln Gly Gly Gly His Trp Ser Gln Val Gln Thr Ile His Gly Thr Gln
440                 445                 450                 455 att ggc tct tat ttc ggt ggg gag ctg tgt ggc gtc gac gtg gac caa     1506
Ile Gly Ser Tyr Phe Gly Gly Glu Leu Cys Gly Val Asp Val Asp Gln
                460                 465                 470 gat ggg gag aca gag ctg ctg ctg att ggt gcc cca ctg ttc tat ggg     1554
Asp Gly Glu Thr Glu Leu Leu Leu Ile Gly Ala Pro Leu Phe Tyr Gly
            475                 480                 485
```

```
gag cag aga gga ggc cgg gtg ttt atc tac cag aga aga cag ttg ggg    1602
Glu Gln Arg Gly Gly Arg Val Phe Ile Tyr Gln Arg Arg Gln Leu Gly
            490                 495                 500 ttt gaa gaa gtc tca gag ctg cag ggg gac ccc ggc tac cca ctc ggg    1650
Phe Glu Glu Val Ser Glu Leu Gln Gly Asp Pro Gly Tyr Pro Leu Gly
        505                 510                 515 cgg ttt gga gaa gcc atc act gct ctg aca gac atc aac ggc gat ggg    1698
Arg Phe Gly Glu Ala Ile Thr Ala Leu Thr Asp Ile Asn Gly Asp Gly
520                 525                 530                 535 ctg gta gac gtg gct gtg ggg gcc cct ctg gag gag cag ggg gct gtg    1746
Leu Val Asp Val Ala Val Gly Ala Pro Leu Glu Glu Gln Gly Ala Val
                540                 545                 550 tac atc ttc aat ggg agg cac ggg ggc ctt agt ccc cag cca agt cag    1794
Tyr Ile Phe Asn Gly Arg His Gly Gly Leu Ser Pro Gln Pro Ser Gln
            555                 560                 565 cgg ata gaa ggg acc caa gtg ctc tca gga att cag tgg ttt gga cgc    1842
Arg Ile Glu Gly Thr Gln Val Leu Ser Gly Ile Gln Trp Phe Gly Arg
        570                 575                 580 tcc atc cat ggg gtg aag gac ctt gaa ggg gat ggc ttg gca gat gtg    1890
Ser Ile His Gly Val Lys Asp Leu Glu Gly Asp Gly Leu Ala Asp Val
585                 590                 595 gct gtg ggg gct gag agc cag atg atc gtg ctg agc tcc cgg ccc gtg    1938
Ala Val Gly Ala Glu Ser Gln Met Ile Val Leu Ser Ser Arg Pro Val
600                 605                 610                 615 gtg gat atg gtc acc ctg atg tcc ttc tct cca gct gag atc cca gtg    1986
Val Asp Met Val Thr Leu Met Ser Phe Ser Pro Ala Glu Ile Pro Val
                620                 625                 630 cat gaa gtg gag tgc tcc tat tca acc agt aac aag atg aaa gaa gga    2034
His Glu Val Glu Cys Ser Tyr Ser Thr Ser Asn Lys Met Lys Glu Gly
            635                 640                 645 gtt aat atc aca atc tgt ttc cag atc aag tct ctc atc ccc cag ttc    2082
Val Asn Ile Thr Ile Cys Phe Gln Ile Lys Ser Leu Ile Pro Gln Phe
        650                 655                 660 caa ggc cgc ctg gtt gcc aat ctc act tac act ctg cag ctg gat ggc    2130
Gln Gly Arg Leu Val Ala Asn Leu Thr Tyr Thr Leu Gln Leu Asp Gly
665                 670                 675 cac cgg acc aga aga cgg ggg ttg ttc cca gga ggg aga cat gaa ctc    2178
His Arg Thr Arg Arg Arg Gly Leu Phe Pro Gly Gly Arg His Glu Leu
680                 685                 690                 695 aga agg aat ata gct gtc acc acc agc atg tca tgc act gac ttc tca    2226
Arg Arg Asn Ile Ala Val Thr Thr Ser Met Ser Cys Thr Asp Phe Ser
                700                 705                 710 ttt cat ttc ccg gta tgt gtt caa gac ctc atc tcc ccc atc aat gtt    2274
Phe His Phe Pro Val Cys Val Gln Asp Leu Ile Ser Pro Ile Asn Val
            715                 720                 725 tcc ctg aat ttc tct ctt tgg gag gag gaa ggg aca ccg agg gac caa    2322
Ser Leu Asn Phe Ser Leu Trp Glu Glu Glu Gly Thr Pro Arg Asp Gln
        730                 735                 740 agg gcg cag ggc aag gac ata ccg ccc atc ctg aga ccc tcc ctg cac    2370
Arg Ala Gln Gly Lys Asp Ile Pro Pro Ile Leu Arg Pro Ser Leu His
745                 750                 755 tcg gaa acc tgg gag atc cct ttt gag aag aac tgt ggg gag gac aag    2418
Ser Glu Thr Trp Glu Ile Pro Phe Glu Lys Asn Cys Gly Glu Asp Lys
760                 765                 770                 775 aag tgt gag gca aac ttg aga gtg tcc ttc tct cct gca aga tcc aga    2466
Lys Cys Glu Ala Asn Leu Arg Val Ser Phe Ser Pro Ala Arg Ser Arg
                780                 785                 790 gcc ctg cgt cta act gct ttt gcc agc ctc tct gtg gag ctg agc ctg    2514
Ala Leu Arg Leu Thr Ala Phe Ala Ser Leu Ser Val Glu Leu Ser Leu
            795                 800                 805
```

|     |      |
|---|---:|
| agt aac ttg gaa gaa gat gct tac tgg gtc cag ctg gac ctg cac ttc<br>Ser Asn Leu Glu Glu Asp Ala Tyr Trp Val Gln Leu Asp Leu His Phe<br>    810                 815                 820 | 2562 |
| ccc ccg gga ctc tcc ttc cgc aag gtg gag atg ctg aag ccc cat agc<br>Pro Pro Gly Leu Ser Phe Arg Lys Val Glu Met Leu Lys Pro His Ser<br>825                 830                 835 | 2610 |
| cag ata cct gtg agc tgc gag gag ctt cct gaa gag tcc agg ctt ctg<br>Gln Ile Pro Val Ser Cys Glu Glu Leu Pro Glu Glu Ser Arg Leu Leu<br>840                 845                 850                 855 | 2658 |
| tcc agg gca tta tct tgc aat gtg agc tct ccc atc ttc aaa gca ggc<br>Ser Arg Ala Leu Ser Cys Asn Val Ser Ser Pro Ile Phe Lys Ala Gly<br>                860                 865                 870 | 2706 |
| cac tcg gtt gct ctg cag atg atg ttt aat aca ctg gta aac agc tcc<br>His Ser Val Ala Leu Gln Met Met Phe Asn Thr Leu Val Asn Ser Ser<br>            875                 880                 885 | 2754 |
| tgg ggg gac tcg gtt gaa ttc cac gcc aat gtg acc tgt aac aat gag<br>Trp Gly Asp Ser Val Glu Leu His Ala Asn Val Thr Cys Asn Asn Glu<br>        890                 895                 900 | 2802 |
| gac tca gac ctc ctg gag gac aac tca gcc act acc atc atc ccc atc<br>Asp Ser Asp Leu Leu Glu Asp Asn Ser Ala Thr Thr Ile Ile Pro Ile<br>    905                 910                 915 | 2850 |
| ctg tac ccc atc aac atc ctc atc cag gac caa gaa gac tcc aca ctc<br>Leu Tyr Pro Ile Asn Ile Leu Ile Gln Asp Gln Glu Asp Ser Thr Leu<br>920                 925                 930                 935 | 2898 |
| tat gtc agt ttc acc ccc aaa ggc ccc aag atc cac caa gtc aag cac<br>Tyr Val Ser Phe Thr Pro Lys Gly Pro Lys Ile His Gln Val Lys His<br>                940                 945                 950 | 2946 |
| atg tac cag gtg agg atc cag cct tcc atc cac gac cac aac ata ccc<br>Met Tyr Gln Val Arg Ile Gln Pro Ser Ile His Asp His Asn Ile Pro<br>            955                 960                 965 | 2994 |
| acc ctg gag gct gtg gtt ggg gtg cca cag cct ccc agc gag ggg ccc<br>Thr Leu Glu Ala Val Val Gly Val Pro Gln Pro Pro Ser Glu Gly Pro<br>        970                 975                 980 | 3042 |
| atc aca cac cag tgg agc gtg cag atg gag cct ccc gtg ccc tgc cac<br>Ile Thr His Gln Trp Ser Val Gln Met Glu Pro Pro Val Pro Cys His<br>    985                 990                 995 | 3090 |
| tat gag gat ctg gag agg ctc ccg gat gca gct gag cct tgt ctc<br>Tyr Glu Asp Leu Glu Arg Leu Pro Asp Ala Ala Glu Pro Cys Leu<br>1000                1005                1010 | 3135 |
| ccc gga gcc ctg ttc cgc tgc cct gtt gtc ttc agg cag gag atc<br>Pro Gly Ala Leu Phe Arg Cys Pro Val Val Phe Arg Gln Glu Ile<br>1015                1020                1025 | 3180 |
| ctc gtc caa gtg atc ggg act ctg gag ctg gtg gga gag atc gag<br>Leu Val Gln Val Ile Gly Thr Leu Glu Leu Val Gly Glu Ile Glu<br>1030                1035                1040 | 3225 |
| gcc tct tcc atg ttc agc ctc tgc agc tcc ctc tcc atc tcc ttc<br>Ala Ser Ser Met Phe Ser Leu Cys Ser Ser Leu Ser Ile Ser Phe<br>1045                1050                1055 | 3270 |
| aac agc agc aag cat ttc cac ctc tat ggc agc aac gcc tcc ctg<br>Asn Ser Ser Lys His Phe His Leu Tyr Gly Ser Asn Ala Ser Leu<br>1060                1065                1070 | 3315 |
| gcc cag gtt gtc atg aag gtt gac gtg gtg tat gag aag cag atg<br>Ala Gln Val Val Met Lys Val Asp Val Val Tyr Glu Lys Gln Met<br>1075                1080                1085 | 3360 |
| ctc tac ctc tac gtg ctg agc ggc atc ggg ggg ctg ctg ctg ctg<br>Leu Tyr Leu Tyr Val Leu Ser Gly Ile Gly Gly Leu Leu Leu Leu<br>1090                1095                1100 | 3405 |
| ctg ctc att ttc ata gtg ctg tac aag gtt ggt ttc ttc aaa cgg<br>Leu Leu Ile Phe Ile Val Leu Tyr Lys Val Gly Phe Phe Lys Arg<br>1105                1110                1115 | 3450 |

-continued

| | | |
|---|---|---|
| aac ctg aag gag aag atg gag gct ggc agg ggt gtc ccg aat gga<br>Asn Leu Lys Glu Lys Met Glu Ala Gly Arg Gly Val Pro Asn Gly<br>1120                                1125                          1130 | | 3495 |
| atc cct gca gaa gac tct gag cag ctg gca tct ggg caa gag gct<br>Ile Pro Ala Glu Asp Ser Glu Gln Leu Ala Ser Gly Gln Glu Ala<br>1135                                1140                          1145 | | 3540 |
| ggg gat ccc ggc tgc ctg aag ccc ctc cat gag aag gac tct gag<br>Gly Asp Pro Gly Cys Leu Lys Pro Leu His Glu Lys Asp Ser Glu<br>1150                                1155                          1160 | | 3585 |
| agt ggt ggc aag gac tgagtccagg cctgtgaggt gcagagtgcc<br>Ser Gly Gly Gly Lys Asp<br>1165                    1170 | | 3633 |
| cagaactgga ctcaggatgc ccagggccac tcttaattaa aagggtgggc gcgccgaccc | | 3693 |
| agctttcttg tacaaagtgg ttgatctaga gggcccgcgg ttcgaaggta agcctatccc | | 3753 |
| taaccctctc ctcggtctcg attctacgcg taccggttag taatgagttt aaacggggga | | 3813 |
| ggctaactga aacacggaag | | 3833 |

<210> SEQ ID NO 8
<211> LENGTH: 1170
<212> TYPE: PRT
<213> ORGANISM: Homo sapiens

<400> SEQUENCE: 8

Met Lys Asp Ser Cys Ile Thr Val Met Ala Met Ala Leu Leu Ser Gly
1               5                  10               15

Phe Phe Phe Phe Ala Pro Ala Ser Ser Tyr Asn Leu Asp Val Arg Gly
              20                  25                  30

Ala Arg Ser Phe Ser Pro Pro Arg Ala Gly Arg His Phe Gly Tyr Arg
          35                  40                  45

Val Leu Gln Val Gly Asn Gly Val Ile Val Gly Ala Pro Gly Glu Gly
      50                  55                  60

Asn Ser Thr Gly Ser Leu Tyr Gln Cys Gln Ser Gly Thr Gly His Cys
65               70                 75               80

Leu Pro Val Thr Leu Arg Gly Ser Asn Tyr Thr Ser Lys Tyr Leu Gly
              85                  90               95

Met Thr Leu Ala Thr Asp Pro Thr Asp Gly Ser Ile Leu Ala Cys Asp
          100                 105              110

Pro Gly Leu Ser Arg Thr Cys Asp Gln Asn Thr Tyr Leu Ser Gly Leu
        115                120              125

Cys Tyr Leu Phe Arg Gln Asn Leu Gln Gly Pro Met Leu Gln Gly Arg
    130                135              140

Pro Gly Phe Gln Glu Cys Ile Lys Gly Asn Val Asp Leu Val Phe Leu
145             150               155              160

Phe Asp Gly Ser Met Ser Leu Gln Pro Asp Glu Phe Gln Lys Ile Leu
              165             170            175

Asp Phe Met Lys Asp Val Met Lys Lys Leu Ser Asn Thr Ser Tyr Gln
          180               185              190

Phe Ala Ala Val Gln Phe Ser Thr Ser Tyr Lys Thr Glu Phe Asp Phe
        195              200              205

Ser Asp Tyr Val Lys Arg Lys Asp Pro Asp Ala Leu Leu Lys His Val
    210                215              220

Lys His Met Leu Leu Leu Thr Asn Thr Phe Gly Ala Ile Asn Tyr Val
225             230               235              240

Ala Thr Glu Val Phe Arg Glu Glu Leu Gly Ala Arg Pro Asp Ala Thr
          245               250              255

```
Lys Val Leu Ile Ile Thr Asp Gly Glu Ala Thr Asp Ser Gly Asn
            260                 265                 270
Ile Asp Ala Ala Lys Asp Ile Ile Arg Tyr Ile Ile Gly Ile Gly Lys
        275                 280                 285
His Phe Gln Thr Lys Glu Ser Gln Glu Thr Leu His Lys Phe Ala Ser
        290                 295                 300
Lys Pro Ala Ser Glu Phe Val Lys Ile Leu Asp Thr Phe Glu Lys Leu
305                 310                 315                 320
Lys Asp Leu Phe Thr Glu Leu Gln Lys Lys Ile Tyr Val Ile Glu Gly
                325                 330                 335
Thr Ser Lys Gln Asp Leu Thr Ser Phe Asn Met Glu Leu Ser Ser Ser
                340                 345                 350
Gly Ile Ser Ala Asp Leu Ser Arg Gly His Ala Val Val Gly Ala Val
                355                 360                 365
Gly Ala Lys Asp Trp Ala Gly Phe Leu Asp Leu Lys Ala Asp Leu
        370                 375                 380
Gln Asp Asp Thr Phe Ile Gly Asn Glu Pro Leu Thr Pro Glu Val Arg
385                 390                 395                 400
Ala Gly Tyr Leu Gly Tyr Thr Val Thr Trp Leu Pro Ser Arg Gln Lys
                405                 410                 415
Thr Ser Leu Leu Ala Ser Gly Ala Pro Arg Tyr Gln His Met Gly Arg
                420                 425                 430
Val Leu Leu Phe Gln Glu Pro Gln Gly Gly Gly His Trp Ser Gln Val
                435                 440                 445
Gln Thr Ile His Gly Thr Gln Ile Gly Ser Tyr Phe Gly Gly Glu Leu
                450                 455                 460
Cys Gly Val Asp Val Asp Gln Asp Gly Glu Thr Glu Leu Leu Leu Ile
465                 470                 475                 480
Gly Ala Pro Leu Phe Tyr Gly Glu Gln Arg Gly Gly Arg Val Phe Ile
                485                 490                 495
Tyr Gln Arg Arg Gln Leu Gly Phe Glu Glu Val Ser Glu Leu Gln Gly
                500                 505                 510
Asp Pro Gly Tyr Pro Leu Gly Arg Phe Gly Glu Ala Ile Thr Ala Leu
                515                 520                 525
Thr Asp Ile Asn Gly Asp Gly Leu Val Asp Val Ala Val Gly Ala Pro
            530                 535                 540
Leu Glu Glu Gln Gly Ala Val Tyr Ile Phe Asn Gly Arg His Gly Gly
545                 550                 555                 560
Leu Ser Pro Gln Pro Ser Gln Arg Ile Glu Gly Thr Gln Val Leu Ser
                565                 570                 575
Gly Ile Gln Trp Phe Gly Arg Ser Ile His Gly Val Lys Asp Leu Glu
                580                 585                 590
Gly Asp Gly Leu Ala Asp Val Ala Val Gly Ala Glu Ser Gln Met Ile
            595                 600                 605
Val Leu Ser Ser Arg Pro Val Val Asp Met Val Thr Leu Met Ser Phe
610                 615                 620
Ser Pro Ala Glu Ile Pro Val His Glu Val Glu Cys Ser Tyr Ser Thr
625                 630                 635                 640
Ser Asn Lys Met Lys Glu Gly Val Asn Ile Thr Ile Cys Phe Gln Ile
                645                 650                 655
Lys Ser Leu Ile Pro Gln Phe Gln Gly Arg Leu Val Ala Asn Leu Thr
                660                 665                 670
Tyr Thr Leu Gln Leu Asp Gly His Arg Thr Arg Arg Arg Gly Leu Phe
```

```
                675                 680                 685
Pro Gly Gly Arg His Glu Leu Arg Arg Asn Ile Ala Val Thr Thr Ser
690                 695                 700

Met Ser Cys Thr Asp Phe Ser Phe His Phe Pro Val Cys Val Gln Asp
705                 710                 715                 720

Leu Ile Ser Pro Ile Asn Val Ser Leu Asn Phe Ser Leu Trp Glu Glu
                725                 730                 735

Glu Gly Thr Pro Arg Asp Gln Arg Ala Gln Gly Lys Asp Ile Pro Pro
                740                 745                 750

Ile Leu Arg Pro Ser Leu His Ser Glu Thr Trp Glu Ile Pro Phe Glu
                755                 760                 765

Lys Asn Cys Gly Glu Asp Lys Lys Cys Glu Ala Asn Leu Arg Val Ser
770                 775                 780

Phe Ser Pro Ala Arg Ser Arg Ala Leu Arg Leu Thr Ala Phe Ala Ser
785                 790                 795                 800

Leu Ser Val Glu Leu Ser Leu Ser Asn Leu Glu Glu Asp Ala Tyr Trp
                805                 810                 815

Val Gln Leu Asp Leu His Phe Pro Pro Gly Leu Ser Phe Arg Lys Val
                820                 825                 830

Glu Met Leu Lys Pro His Ser Gln Ile Pro Val Ser Cys Glu Glu Leu
                835                 840                 845

Pro Glu Glu Ser Arg Leu Leu Ser Arg Ala Leu Ser Cys Asn Val Ser
850                 855                 860

Ser Pro Ile Phe Lys Ala Gly His Ser Val Ala Leu Gln Met Met Phe
865                 870                 875                 880

Asn Thr Leu Val Asn Ser Ser Trp Gly Asp Ser Val Glu Leu His Ala
                885                 890                 895

Asn Val Thr Cys Asn Asn Glu Asp Ser Asp Leu Leu Glu Asp Asn Ser
                900                 905                 910

Ala Thr Thr Ile Ile Pro Ile Leu Tyr Pro Ile Asn Ile Leu Ile Gln
                915                 920                 925

Asp Gln Glu Asp Ser Thr Leu Tyr Val Ser Phe Thr Pro Lys Gly Pro
930                 935                 940

Lys Ile His Gln Val Lys His Met Tyr Gln Val Arg Ile Gln Pro Ser
945                 950                 955                 960

Ile His Asp His Asn Ile Pro Thr Leu Glu Ala Val Val Gly Val Pro
                965                 970                 975

Gln Pro Pro Ser Glu Gly Pro Ile Thr His Gln Trp Ser Val Gln Met
                980                 985                 990

Glu Pro Pro Val Pro Cys His Tyr  Glu Asp Leu Glu Arg Leu Pro Asp
                995                 1000                1005

Ala Ala  Glu Pro Cys Leu Pro  Gly Ala Leu Phe Arg  Cys Pro Val
    1010                1015                1020

Val Phe Arg Gln Glu Ile Leu  Val Gln Val Ile Gly  Thr Leu Glu
    1025                1030                1035

Leu Val Gly Glu Ile Glu Ala  Ser Ser Met Phe Ser  Leu Cys Ser
    1040                1045                1050

Ser Leu Ser Ile Ser Phe Asn  Ser Ser Lys His Phe  His Leu Tyr
    1055                1060                1065

Gly Ser  Asn Ala Ser Leu Ala  Gln Val Val Met Lys  Val Asp Val
    1070                1075                1080

Val Tyr Glu Lys Gln Met Leu  Tyr Leu Tyr Val Leu  Ser Gly Ile
    1085                1090                1095
```

```
Gly Gly Leu Leu Leu Leu Leu  Leu Ile Phe Ile Val  Leu Tyr Lys
        1100            1105               1110

Val Gly Phe Phe Lys Arg Asn  Leu Lys Glu Lys Met  Glu Ala Gly
        1115            1120               1125

Arg Gly Val Pro Asn Gly Ile  Pro Ala Glu Asp Ser  Glu Gln Leu
        1130            1135               1140

Ala Ser Gly Gln Glu Ala Gly  Asp Pro Gly Cys Leu  Lys Pro Leu
        1145            1150               1155

His Glu Lys Asp Ser Glu Ser  Gly Gly Gly Lys Asp
        1160            1165               1170

<210> SEQ ID NO 9
<211> LENGTH: 4218
<212> TYPE: DNA
<213> ORGANISM: Homo sapiens
<220> FEATURE:
<221> NAME/KEY: CDS
<222> LOCATION: (186)..(3695)
<223> OTHER INFORMATION:
<220> FEATURE:
<221> NAME/KEY: misc_feature
<222> LOCATION: (4143)..(4143)
<223> OTHER INFORMATION: n is not determined.

<400> SEQUENCE: 9
caaatgggcg gtaggcgtgt acggtgggag gtctatataa gcagagctct ctggctaact        60
agagaaccca ctgcttactg gcttatcgaa attaatacga ctcactatag ggagacccaa       120
gctggctagt taagctatca acaagtttgt acaaaaaagc aggctccgcg ccgccccct        180 tcacc atg aag gat tcc tgc atc act gtg atg gcc atg gcg ctg ctg tct      230
      Met Lys Asp Ser Cys Ile Thr Val Met Ala Met Ala Leu Leu Ser
      1               5                   10                  15 ggg ttc ttt ttc ttc gcg ccg gcc tcg agc tac aac ctg gac gtg cgg      278
Gly Phe Phe Phe Phe Ala Pro Ala Ser Ser Tyr Asn Leu Asp Val Arg
                20                  25                  30 ggc gcg cgg agc ttc tcc cca ccg cgc gcc ggg agg cac ttt gga tac      326
Gly Ala Arg Ser Phe Ser Pro Pro Arg Ala Gly Arg His Phe Gly Tyr
            35                  40                  45 cgc gtc ctg cag gtc gga aac ggg gtc atc gtg gga gct cca ggg gag      374
Arg Val Leu Gln Val Gly Asn Gly Val Ile Val Gly Ala Pro Gly Glu
        50                  55                  60 ggg aac agc aca gga agc ctc tat cag tgc cag tcg ggc aca gga cac      422
Gly Asn Ser Thr Gly Ser Leu Tyr Gln Cys Gln Ser Gly Thr Gly His
    65                  70                  75 tgc ctg cca gtc acc ctg aga ggt tcc aac tat acc tcc aag tac ttg      470
Cys Leu Pro Val Thr Leu Arg Gly Ser Asn Tyr Thr Ser Lys Tyr Leu
80                  85                  90                  95 gga atg acc ttg gca aca gac ccc aca gat gga agc att ttg gcc tgt      518
Gly Met Thr Leu Ala Thr Asp Pro Thr Asp Gly Ser Ile Leu Ala Cys
                100                 105                 110 gac cct ggg ctg tct cga acg tgt gac cag aac acc tat ctg agt ggc      566
Asp Pro Gly Leu Ser Arg Thr Cys Asp Gln Asn Thr Tyr Leu Ser Gly
            115                 120                 125 ctg tgt tac ctc ttc cgc cag aat ctg cag ggt ccc atg ctg cag ggg      614
Leu Cys Tyr Leu Phe Arg Gln Asn Leu Gln Gly Pro Met Leu Gln Gly
        130                 135                 140 cgc cct ggt ttt cag gaa tgt atc aag ggc aac gta gac ctg gta ttt      662
Arg Pro Gly Phe Gln Glu Cys Ile Lys Gly Asn Val Asp Leu Val Phe
    145                 150                 155 ctg ttt gat ggt tcg atg agc ttg cag cca gat gaa ttt cag aaa att      710
Leu Phe Asp Gly Ser Met Ser Leu Gln Pro Asp Glu Phe Gln Lys Ile
160                 165                 170                 175
```

```
ctg gac ttc atg aag gat gtg atg aag aaa ctc agc aac act tcg tac        758
Leu Asp Phe Met Lys Asp Val Met Lys Lys Leu Ser Asn Thr Ser Tyr
            180                 185                 190 cag ttt gct gct gtt cag ttt tcc aca agc tac aaa aca gaa ttt gat        806
Gln Phe Ala Ala Val Gln Phe Ser Thr Ser Tyr Lys Thr Glu Phe Asp
        195                 200                 205 ttc tca gat tat gtt aaa cgg aag gac cct gat gct ctg ctg aag cat        854
Phe Ser Asp Tyr Val Lys Arg Lys Asp Pro Asp Ala Leu Leu Lys His
    210                 215                 220 gta aag cac atg ttg ctg ttg acc aat acc ttt ggt gcc atc aat tat        902
Val Lys His Met Leu Leu Leu Thr Asn Thr Phe Gly Ala Ile Asn Tyr
225                 230                 235 gtc gcg aca gag gtg ttc cgg gag gag ctg ggg gcc cgg cca gat gcc        950
Val Ala Thr Glu Val Phe Arg Glu Glu Leu Gly Ala Arg Pro Asp Ala
240                 245                 250                 255 acc aaa gtg ctt atc atc atc acg gat ggg gag gcc act gac agt ggc        998
Thr Lys Val Leu Ile Ile Ile Thr Asp Gly Glu Ala Thr Asp Ser Gly
                260                 265                 270 aac atc gat gcg gcc aaa gac atc atc cgc tac atc atc ggg att gga       1046
Asn Ile Asp Ala Ala Lys Asp Ile Ile Arg Tyr Ile Ile Gly Ile Gly
            275                 280                 285 aag cat ttt cag acc aag gag agt cag gag acc ctc cac aaa ttt gca       1094
Lys His Phe Gln Thr Lys Glu Ser Gln Glu Thr Leu His Lys Phe Ala
        290                 295                 300 tca aaa ccc gcg agc gag ttt gtg aaa att ctg gac aca ttt gag aag       1142
Ser Lys Pro Ala Ser Glu Phe Val Lys Ile Leu Asp Thr Phe Glu Lys
    305                 310                 315 ctg aaa gat cta ttc act gag ctg cag aag aag atc tat gtc att gag       1190
Leu Lys Asp Leu Phe Thr Glu Leu Gln Lys Lys Ile Tyr Val Ile Glu
320                 325                 330                 335 ggc aca agc aaa cag gac ctg act tcc ttc aac atg gag ctg tcc tcc       1238
Gly Thr Ser Lys Gln Asp Leu Thr Ser Phe Asn Met Glu Leu Ser Ser
                340                 345                 350 agc ggc atc agt gct gac ctc agc agg ggc cat gca gtc gtg ggg gca       1286
Ser Gly Ile Ser Ala Asp Leu Ser Arg Gly His Ala Val Val Gly Ala
            355                 360                 365 gta gga gcc aag gac tgg gct ggg ggc ttt ctt gac ctg aag gca gac       1334
Val Gly Ala Lys Asp Trp Ala Gly Gly Phe Leu Asp Leu Lys Ala Asp
        370                 375                 380 ctg cag gat gac aca ttt att ggg aat gaa cca ttg aca cca gaa gtg       1382
Leu Gln Asp Asp Thr Phe Ile Gly Asn Glu Pro Leu Thr Pro Glu Val
    385                 390                 395 aga gca ggc tat ttg ggt tac acc gtg acc tgg ctg ccc tcc cgg caa       1430
Arg Ala Gly Tyr Leu Gly Tyr Thr Val Thr Trp Leu Pro Ser Arg Gln
400                 405                 410                 415 aag act tcg ttg ctg gcc tcg gga gcc cct cga tac cag cac atg ggc       1478
Lys Thr Ser Leu Leu Ala Ser Gly Ala Pro Arg Tyr Gln His Met Gly
                420                 425                 430 cga gtg ctg ctg ttc caa gag cca cag ggc gga gga cac tgg agc cag       1526
Arg Val Leu Leu Phe Gln Glu Pro Gln Gly Gly Gly His Trp Ser Gln
            435                 440                 445 gtc cag aca atc cat ggg acc cag att ggc tct tat ttc ggt ggg gag       1574
Val Gln Thr Ile His Gly Thr Gln Ile Gly Ser Tyr Phe Gly Gly Glu
        450                 455                 460 ctg tgt ggc gtc gac gtg gac caa gat ggg gag aca gag ctg ctg ctg       1622
Leu Cys Gly Val Asp Val Asp Gln Asp Gly Glu Thr Glu Leu Leu Leu
    465                 470                 475 att ggt gcc cca ctg ttc tat ggg gag cag aga gga ggc cgg gtg ttt       1670
Ile Gly Ala Pro Leu Phe Tyr Gly Glu Gln Arg Gly Gly Arg Val Phe
480                 485                 490                 495
```

| | | |
|---|---|---|
| atc tac cag aga aga cag ttg ggg ttt gaa gaa gtc tca gag ctg cag<br>Ile Tyr Gln Arg Arg Gln Leu Gly Phe Glu Glu Val Ser Glu Leu Gln<br>500             505             510 | | 1718 |
| ggg gac ccc ggc tac cca ctc ggg cgg ttt gga gaa gcc atc act gct<br>Gly Asp Pro Gly Tyr Pro Leu Gly Arg Phe Gly Glu Ala Ile Thr Ala<br>    515             520             525 | | 1766 |
| ctg aca gac atc aac ggc gat ggg ctg gta gac gtg gct gtg ggg gcc<br>Leu Thr Asp Ile Asn Gly Asp Gly Leu Val Asp Val Ala Val Gly Ala<br>530             535             540 | | 1814 |
| cct ctg gag gag cag ggg gct gtg tac atc ttc aat ggg agg cac ggg<br>Pro Leu Glu Glu Gln Gly Ala Val Tyr Ile Phe Asn Gly Arg His Gly<br>545             550             555 | | 1862 |
| ggg ctt agt ccc cag cca agt cag cgg ata gaa ggg acc caa gtg ctc<br>Gly Leu Ser Pro Gln Pro Ser Gln Arg Ile Glu Gly Thr Gln Val Leu<br>560             565             570             575 | | 1910 |
| tca gga att cag tgg ttt gga cgc tcc atc cat ggg gtg aag gac ctt<br>Ser Gly Ile Gln Trp Phe Gly Arg Ser Ile His Gly Val Lys Asp Leu<br>            580             585             590 | | 1958 |
| gaa ggg gat ggc ttg gca gat gtg gct gtg ggg gct gag agc cag atg<br>Glu Gly Asp Gly Leu Ala Asp Val Ala Val Gly Ala Glu Ser Gln Met<br>    595             600             605 | | 2006 |
| atc gtg ctg agc tcc cgg ccc gtg gtg gat atg gtc acc ctg atg tcc<br>Ile Val Leu Ser Ser Arg Pro Val Val Asp Met Val Thr Leu Met Ser<br>610             615             620 | | 2054 |
| ttc tct cca gct gag atc cca gtg cat gaa gtg gag tgc tcc tat tca<br>Phe Ser Pro Ala Glu Ile Pro Val His Glu Val Glu Cys Ser Tyr Ser<br>625             630             635 | | 2102 |
| acc agt aac aag atg aaa gaa gga gtt aat atc aca atc tgt ttc cag<br>Thr Ser Asn Lys Met Lys Glu Gly Val Asn Ile Thr Ile Cys Phe Gln<br>640             645             650             655 | | 2150 |
| atc aag tct ctc atc ccc cag ttc caa ggc cgc ctg gtt gcc aat ctc<br>Ile Lys Ser Leu Ile Pro Gln Phe Gln Gly Arg Leu Val Ala Asn Leu<br>            660             665             670 | | 2198 |
| act tac act ctg cag ctg gat ggc cac cgg acc aga aga cgg ggg ttg<br>Thr Tyr Thr Leu Gln Leu Asp Gly His Arg Thr Arg Arg Arg Gly Leu<br>    675             680             685 | | 2246 |
| ttc cca gga ggg aga cat gaa ctc aga agg aat ata gct gtc acc acc<br>Phe Pro Gly Gly Arg His Glu Leu Arg Arg Asn Ile Ala Val Thr Thr<br>690             695             700 | | 2294 |
| agc atg tca tgc act gac ttc tca ttt cat ttc ccg gta tgt gtt caa<br>Ser Met Ser Cys Thr Asp Phe Ser Phe His Phe Pro Val Cys Val Gln<br>705             710             715 | | 2342 |
| gac ctc atc tcc ccc atc aat gtt tcc ctg aat ttc tct ctt tgg gag<br>Asp Leu Ile Ser Pro Ile Asn Val Ser Leu Asn Phe Ser Leu Trp Glu<br>720             725             730             735 | | 2390 |
| gag gaa ggg aca ccg agg gac caa agg gcg cag ggc aag gac ata ccg<br>Glu Glu Gly Thr Pro Arg Asp Gln Arg Ala Gln Gly Lys Asp Ile Pro<br>            740             745             750 | | 2438 |
| ccc atc ctg aga ccc tcc ctg cac tcg gaa acc tgg gag atc cct ttt<br>Pro Ile Leu Arg Pro Ser Leu His Ser Glu Thr Trp Glu Ile Pro Phe<br>    755             760             765 | | 2486 |
| gag aag aac tgt ggg gag gac aag aag tgt gag gca aac ttg aga gtg<br>Glu Lys Asn Cys Gly Glu Asp Lys Lys Cys Glu Ala Asn Leu Arg Val<br>770             775             780 | | 2534 |
| tcc ttc tct cct gca aga tcc aca gcc ctg cgt cta act gct ttt gcc<br>Ser Phe Ser Pro Ala Arg Ser Thr Ala Leu Arg Leu Thr Ala Phe Ala<br>785             790             795 | | 2582 |
| agc ctc tct gtg gag ctg agc ctg agt aac ttg gaa gaa gat gct tac<br>Ser Leu Ser Val Glu Leu Ser Leu Ser Asn Leu Glu Glu Asp Ala Tyr<br>800             805             810             815 | | 2630 |

-continued

| | | |
|---|---|---|
| tgg gtc cag ctg gac ctg cac ttc ccc ccg gga ctc tcc ttc cgc aag<br>Trp Val Gln Leu Asp Leu His Phe Pro Pro Gly Leu Ser Phe Arg Lys<br>820                            825                         830 | 2678 | |
| gtg gag atg ctg aag ccc cat agc cag ata cct gtg agc tgc gag gag<br>Val Glu Met Leu Lys Pro His Ser Gln Ile Pro Val Ser Cys Glu Glu<br>835                        840                         845 | 2726 | |
| ctt cct gaa gag tcc agg ctt ctg tcc agg gca tta tct tgc aat gtg<br>Leu Pro Glu Glu Ser Arg Leu Leu Ser Arg Ala Leu Ser Cys Asn Val<br>850                        855                         860 | 2774 | |
| agc tct ccc atc ttc aaa gca ggc cac tcg gtt gct ctg cag atg atg<br>Ser Ser Pro Ile Phe Lys Ala Gly His Ser Val Ala Leu Gln Met Met<br>865                        870                         875 | 2822 | |
| ttt aat aca ctg gta aac agc tcc tgg ggg gac tcg gtt gaa ttg cac<br>Phe Asn Thr Leu Val Asn Ser Ser Trp Gly Asp Ser Val Glu Leu His<br>880                        885                         890                         895 | 2870 | |
| gcc aat gtg acc tgt aac aat gag gac tca gac ctc ctg gag gac aac<br>Ala Asn Val Thr Cys Asn Asn Glu Asp Ser Asp Leu Leu Glu Asp Asn<br>900                        905                         910 | 2918 | |
| tca gcc act acc atc atc ccc atc ctg tac ccc atc aac atc ctc atc<br>Ser Ala Thr Thr Ile Ile Pro Ile Leu Tyr Pro Ile Asn Ile Leu Ile<br>915                        920                         925 | 2966 | |
| cag gac caa gaa gac tcc aca ctc tat gtc agt ttc acc ccc aaa ggc<br>Gln Asp Gln Glu Asp Ser Thr Leu Tyr Val Ser Phe Thr Pro Lys Gly<br>930                        935                         940 | 3014 | |
| ccc aag atc cac caa gtc aag cac atg tac cag gtg agg atc cag cct<br>Pro Lys Ile His Gln Val Lys His Met Tyr Gln Val Arg Ile Gln Pro<br>945                        950                         955 | 3062 | |
| tcc atc cac gac cac aac ata ccc acc ctg gag gct gtg gtt ggg gtg<br>Ser Ile His Asp His Asn Ile Pro Thr Leu Glu Ala Val Val Gly Val<br>960                        965                         970                         975 | 3110 | |
| cca cag cct ccc agc gag ggg ccc atc aca cac cag tgg agc gtg cag<br>Pro Gln Pro Pro Ser Glu Gly Pro Ile Thr His Gln Trp Ser Val Gln<br>980                        985                         990 | 3158 | |
| atg gag cct ccc gtg ccc tgc cac tat gag gat ctg gag agg ctc ccg<br>Met Glu Pro Pro Val Pro Cys His Tyr Glu Asp Leu Glu Arg Leu Pro<br>995                        1000                      1005 | 3206 | |
| gat gca gct gag cct tgt ctc ccc gga gcc ctg ttc cgc tgc cct<br>Asp Ala Ala Glu Pro Cys Leu Pro Gly Ala Leu Phe Arg Cys Pro<br>1010                        1015                      1020 | 3251 | |
| gtt gtc ttc agg cag gag atc ctc gtc caa gtg atc ggg act ctg<br>Val Val Phe Arg Gln Glu Ile Leu Val Gln Val Ile Gly Thr Leu<br>1025                        1030                      1035 | 3296 | |
| gag ctg gtg gga gag atc gag gcc tct tcc atg ttc agc ctc tgc<br>Glu Leu Val Gly Glu Ile Glu Ala Ser Ser Met Phe Ser Leu Cys<br>1040                        1045                      1050 | 3341 | |
| agc tcc ctc tcc atc tcc ttc aac agc agc aag cat ttc cac ctc<br>Ser Ser Leu Ser Ile Ser Phe Asn Ser Ser Lys His Phe His Leu<br>1055                        1060                      1065 | 3386 | |
| tat ggc agc aac gcc tcc ctg gcc cag gtt gtc atg aag gtt gac<br>Tyr Gly Ser Asn Ala Ser Leu Ala Gln Val Val Met Lys Val Asp<br>1070                        1075                      1080 | 3431 | |
| gtg gtg tat gag aag cag atg ctc tac ctc tac gtg ctg agc ggc<br>Val Val Tyr Glu Lys Gln Met Leu Tyr Leu Tyr Val Leu Ser Gly<br>1085                        1090                      1095 | 3476 | |
| atc ggg ggg ctg ctg ctg ctg ctc att ttc ata gtg ctg tac<br>Ile Gly Gly Leu Leu Leu Leu Leu Leu Ile Phe Ile Val Leu Tyr<br>1100                        1105                      1110 | 3521 | |
| aag gtt ggt ttc ttc aaa cgg aac ctg aag gag aag atg gag gct<br>Lys Val Gly Phe Phe Lys Arg Asn Leu Lys Glu Lys Met Glu Ala<br>1115                        1120                      1125 | 3566 | |

```
ggc agg ggt gtc ccg aat gga atc cct gca gaa gac tct gag cag      3611
Gly Arg Gly Val Pro Asn Gly Ile Pro Ala Glu Asp Ser Glu Gln
        1130                1135                1140 ctg gca tct ggg caa gag gct ggg gat ccc ggc tgc ctg aag ccc      3656
Leu Ala Ser Gly Gln Glu Ala Gly Asp Pro Gly Cys Leu Lys Pro
        1145                1150                1155 ctc cat gag aag gac tct gag agt ggt ggt ggc aag gac tgagtccagg   3705
Leu His Glu Lys Asp Ser Glu Ser Gly Gly Gly Lys Asp
        1160                1165                1170 cctgtgaggt gcagagtgcc cagaactgga ctcaggatgc ccagggccac tcttaattaa   3765
aagggtgggc gcgccgaccc agctttcttg tacaaagtgg ttgatctaga gggcccgcgg   3825
ttcgaaggta agcctatccc taaccctctc ctcggtctcg attctacgcg taccggttag   3885
taatgagttt aaacggggga ggctaactga aacacgaagg gagacaatac cggaaggaac   3945
ccgcgctatg acggcaataa aaagacagaa taaaacgcac gggtgttggg tcgtttgttc   4005
ataaacgcgg ggttcggtcc cagggctggc actctgtcga taccccaccg agaccccatt   4065
ggggccaata cgcccgcgtt tcttcctttt ccccacccca ccccccaagt tcgggtgaag   4125
gcccagggct cgcagccnac gtcggggcgg caggccctgc catagcagat ctgcgcagct   4185
ggggctctag ggggtatccc cacgcgccct gta                               4218

<210> SEQ ID NO 10
<211> LENGTH: 1170
<212> TYPE: PRT
<213> ORGANISM: Homo sapiens

<400> SEQUENCE: 10

Met Lys Asp Ser Cys Ile Thr Val Met Ala Met Ala Leu Leu Ser Gly
1               5                   10                  15

Phe Phe Phe Phe Ala Pro Ala Ser Ser Tyr Asn Leu Asp Val Arg Gly
                20                  25                  30

Ala Arg Ser Phe Ser Pro Pro Arg Ala Gly Arg His Phe Gly Tyr Arg
            35                  40                  45

Val Leu Gln Val Gly Asn Gly Val Ile Val Gly Ala Pro Gly Glu Gly
        50                  55                  60

Asn Ser Thr Gly Ser Leu Tyr Gln Cys Gln Ser Gly Thr Gly His Cys
65                  70                  75                  80

Leu Pro Val Thr Leu Arg Gly Ser Asn Tyr Thr Ser Lys Tyr Leu Gly
                85                  90                  95

Met Thr Leu Ala Thr Asp Pro Thr Asp Gly Ser Ile Leu Ala Cys Asp
            100                 105                 110

Pro Gly Leu Ser Arg Thr Cys Asp Gln Asn Thr Tyr Leu Ser Gly Leu
        115                 120                 125

Cys Tyr Leu Phe Arg Gln Asn Leu Gln Gly Pro Met Leu Gln Gly Arg
    130                 135                 140

Pro Gly Phe Gln Glu Cys Ile Lys Gly Asn Val Asp Leu Val Phe Leu
145                 150                 155                 160

Phe Asp Gly Ser Met Ser Leu Gln Pro Asp Glu Phe Gln Lys Ile Leu
                165                 170                 175

Asp Phe Met Lys Asp Val Met Lys Lys Leu Ser Asn Thr Ser Tyr Gln
            180                 185                 190

Phe Ala Ala Val Gln Phe Ser Thr Ser Tyr Lys Thr Glu Phe Asp Phe
        195                 200                 205

Ser Asp Tyr Val Lys Arg Lys Asp Pro Asp Ala Leu Leu Lys His Val
    210                 215                 220
```

```
Lys His Met Leu Leu Leu Thr Asn Thr Phe Gly Ala Ile Asn Tyr Val
225                 230                 235                 240

Ala Thr Glu Val Phe Arg Glu Glu Leu Gly Ala Arg Pro Asp Ala Thr
            245                 250                 255

Lys Val Leu Ile Ile Thr Asp Gly Glu Ala Thr Asp Ser Gly Asn
        260                 265                 270

Ile Asp Ala Ala Lys Asp Ile Ile Arg Tyr Ile Ile Gly Ile Gly Lys
            275                 280                 285

His Phe Gln Thr Lys Glu Ser Gln Glu Thr Leu His Lys Phe Ala Ser
        290                 295                 300

Lys Pro Ala Ser Glu Phe Val Lys Ile Leu Asp Thr Phe Glu Lys Leu
305                 310                 315                 320

Lys Asp Leu Phe Thr Glu Leu Gln Lys Lys Ile Tyr Val Ile Glu Gly
                325                 330                 335

Thr Ser Lys Gln Asp Leu Thr Ser Phe Asn Met Glu Leu Ser Ser Ser
        340                 345                 350

Gly Ile Ser Ala Asp Leu Ser Arg Gly His Ala Val Val Gly Ala Val
            355                 360                 365

Gly Ala Lys Asp Trp Ala Gly Gly Phe Leu Asp Leu Lys Ala Asp Leu
        370                 375                 380

Gln Asp Asp Thr Phe Ile Gly Asn Glu Pro Leu Thr Pro Glu Val Arg
385                 390                 395                 400

Ala Gly Tyr Leu Gly Tyr Thr Val Thr Trp Leu Pro Ser Arg Gln Lys
                405                 410                 415

Thr Ser Leu Leu Ala Ser Gly Ala Pro Arg Tyr Gln His Met Gly Arg
            420                 425                 430

Val Leu Leu Phe Gln Glu Pro Gln Gly Gly His Trp Ser Gln Val
        435                 440                 445

Gln Thr Ile His Gly Thr Gln Ile Gly Ser Tyr Phe Gly Gly Glu Leu
    450                 455                 460

Cys Gly Val Asp Val Asp Gln Asp Gly Glu Thr Glu Leu Leu Leu Ile
465                 470                 475                 480

Gly Ala Pro Leu Phe Tyr Gly Glu Gln Arg Gly Gly Arg Val Phe Ile
                485                 490                 495

Tyr Gln Arg Arg Gln Leu Gly Phe Glu Glu Val Ser Glu Leu Gln Gly
            500                 505                 510

Asp Pro Gly Tyr Pro Leu Gly Arg Phe Gly Glu Ala Ile Thr Ala Leu
        515                 520                 525

Thr Asp Ile Asn Gly Asp Gly Leu Val Asp Val Ala Val Gly Ala Pro
    530                 535                 540

Leu Glu Glu Gln Gly Ala Val Tyr Ile Phe Asn Gly Arg His Gly Gly
545                 550                 555                 560

Leu Ser Pro Gln Pro Ser Gln Arg Ile Glu Gly Thr Gln Val Leu Ser
                565                 570                 575

Gly Ile Gln Trp Phe Gly Arg Ser Ile His Gly Val Lys Asp Leu Glu
            580                 585                 590

Gly Asp Gly Leu Ala Asp Val Ala Val Gly Ala Glu Ser Gln Met Ile
        595                 600                 605

Val Leu Ser Ser Arg Pro Val Val Asp Met Val Thr Leu Met Ser Phe
    610                 615                 620

Ser Pro Ala Glu Ile Pro Val His Glu Val Glu Cys Ser Tyr Ser Thr
625                 630                 635                 640

Ser Asn Lys Met Lys Glu Gly Val Asn Ile Thr Ile Cys Phe Gln Ile
```

-continued

```
                    645                 650                 655
Lys Ser Leu Ile Pro Gln Phe Gln Gly Arg Leu Val Ala Asn Leu Thr
            660                 665                 670

Tyr Thr Leu Gln Leu Asp Gly His Arg Thr Arg Arg Gly Leu Phe
            675                 680                 685

Pro Gly Gly Arg His Glu Leu Arg Arg Asn Ile Ala Val Thr Thr Ser
690                 695                 700

Met Ser Cys Thr Asp Phe Ser Phe His Phe Pro Val Cys Val Gln Asp
705                 710                 715                 720

Leu Ile Ser Pro Ile Asn Val Ser Leu Asn Phe Ser Leu Trp Glu Glu
            725                 730                 735

Glu Gly Thr Pro Arg Asp Gln Arg Ala Gln Gly Lys Asp Ile Pro Pro
            740                 745                 750

Ile Leu Arg Pro Ser Leu His Ser Glu Thr Trp Glu Ile Pro Phe Glu
            755                 760                 765

Lys Asn Cys Gly Glu Asp Lys Lys Cys Glu Ala Asn Leu Arg Val Ser
            770                 775                 780

Phe Ser Pro Ala Arg Ser Thr Ala Leu Arg Leu Thr Ala Phe Ala Ser
785                 790                 795                 800

Leu Ser Val Glu Leu Ser Leu Ser Asn Leu Glu Glu Asp Ala Tyr Trp
            805                 810                 815

Val Gln Leu Asp Leu His Phe Pro Pro Gly Leu Ser Phe Arg Lys Val
            820                 825                 830

Glu Met Leu Lys Pro His Ser Gln Ile Pro Val Ser Cys Glu Glu Leu
            835                 840                 845

Pro Glu Glu Ser Arg Leu Leu Ser Arg Ala Leu Ser Cys Asn Val Ser
            850                 855                 860

Ser Pro Ile Phe Lys Ala Gly His Ser Val Ala Leu Gln Met Met Phe
865                 870                 875                 880

Asn Thr Leu Val Asn Ser Ser Trp Gly Asp Ser Val Glu Leu His Ala
            885                 890                 895

Asn Val Thr Cys Asn Asn Glu Asp Ser Asp Leu Leu Glu Asp Asn Ser
            900                 905                 910

Ala Thr Thr Ile Ile Pro Ile Leu Tyr Pro Ile Asn Ile Leu Ile Gln
            915                 920                 925

Asp Gln Glu Asp Ser Thr Leu Tyr Val Ser Phe Thr Pro Lys Gly Pro
            930                 935                 940

Lys Ile His Gln Val Lys His Met Tyr Gln Val Arg Ile Gln Pro Ser
945                 950                 955                 960

Ile His Asp His Asn Ile Pro Thr Leu Glu Ala Val Val Gly Val Pro
            965                 970                 975

Gln Pro Pro Ser Glu Gly Pro Ile Thr His Gln Trp Ser Val Gln Met
            980                 985                 990

Glu Pro Pro Val Pro Cys His Tyr Glu Asp Leu Glu Arg Leu Pro Asp
            995                 1000                1005

Ala Ala Glu Pro Cys Leu Pro Gly Ala Leu Phe Arg Cys Pro Val
            1010                1015                1020

Val Phe Arg Gln Glu Ile Leu Val Gln Val Ile Gly Thr Leu Glu
            1025                1030                1035

Leu Val Gly Glu Ile Glu Ala Ser Ser Met Phe Ser Leu Cys Ser
            1040                1045                1050

Ser Leu Ser Ile Ser Phe Asn Ser Ser Lys His Phe His Leu Tyr
            1055                1060                1065
```

```
Gly Ser  Asn Ala Ser Leu Ala  Gln Val Val Met Lys  Val Asp Val
    1070         1075              1080

Val Tyr  Glu Lys Gln Met Leu  Tyr Leu Tyr Val Leu  Ser Gly Ile
    1085         1090              1095

Gly Gly  Leu Leu Leu Leu Leu  Leu Ile Phe Ile Val  Leu Tyr Lys
    1100         1105              1110

Val Gly  Phe Phe Lys Arg Asn  Leu Lys Glu Lys Met  Glu Ala Gly
    1115         1120              1125

Arg Gly  Val Pro Asn Gly Ile  Pro Ala Glu Asp Ser  Glu Gln Leu
    1130         1135              1140

Ala Ser  Gly Gln Glu Ala Gly  Asp Pro Gly Cys Leu  Lys Pro Leu
    1145         1150              1155

His Glu  Lys Asp Ser Glu Ser  Gly Gly Gly Lys Asp
    1160         1165              1170

<210> SEQ ID NO 11
<211> LENGTH: 3795
<212> TYPE: DNA
<213> ORGANISM: Homo sapiens
<220> FEATURE:
<221> NAME/KEY: CDS
<222> LOCATION: (94)..(3549)
<223> OTHER INFORMATION:

<400> SEQUENCE: 11
taatacgact cactataggg agacccaagc tggctagtta agctatcaac aagtttgtac    60
aaaaaagcag ctccgcggc cgcccccttc acc atg gct ctc aga gtc ctt ctg    114
                                   Met Ala Leu Arg Val Leu Leu
                                   1               5 tta aca gcc ttg acc tta tgt cat ggg ttc aac ttg gac act gaa aac    162
Leu Thr Ala Leu Thr Leu Cys His Gly Phe Asn Leu Asp Thr Glu Asn
        10              15                  20 gca atg acc ttc caa gag aac gca agg ggc ttc ggg cag agc gtg gtc    210
Ala Met Thr Phe Gln Glu Asn Ala Arg Gly Phe Gly Gln Ser Val Val
    25                  30                  35 cag ctt cag gga tcc agg gtg gtg gtt gga gcc ccc cag gag ata gtg    258
Gln Leu Gln Gly Ser Arg Val Val Val Gly Ala Pro Gln Glu Ile Val
40                  45                  50                  55 gct gcc aac caa agg ggc agc ctc tac cag tgc gac tac agc aca ggc    306
Ala Ala Asn Gln Arg Gly Ser Leu Tyr Gln Cys Asp Tyr Ser Thr Gly
                60                  65                  70 tca tgc gag ccc atc cgc ctg cag gtc ccc gtg gag gcc gtg aac atg    354
Ser Cys Glu Pro Ile Arg Leu Gln Val Pro Val Glu Ala Val Asn Met
            75                  80                  85 tcc ctg ggc ctg tcc ctg gca gcc acc acc agc ccc cct cag ctg ctg    402
Ser Leu Gly Leu Ser Leu Ala Ala Thr Thr Ser Pro Pro Gln Leu Leu
        90                  95                  100 gcc tgt ggt ccc acc gtg cac cag act tgc agt gag aac acg tat gtg    450
Ala Cys Gly Pro Thr Val His Gln Thr Cys Ser Glu Asn Thr Tyr Val
    105                 110                 115 aaa ggg ctc tgc ttc ctg ttt gga tcc aac cta cgg cag cag ccc cag    498
Lys Gly Leu Cys Phe Leu Phe Gly Ser Asn Leu Arg Gln Gln Pro Gln
120                 125                 130                 135 aag ttc cca gag gcc ctc cga ggg tgt cct caa gag gat agt gac att    546
Lys Phe Pro Glu Ala Leu Arg Gly Cys Pro Gln Glu Asp Ser Asp Ile
                140                 145                 150 gcc ttc ttg att gat ggc tct ggt agc atc atc cca cat gac ttt cgg    594
Ala Phe Leu Ile Asp Gly Ser Gly Ser Ile Ile Pro His Asp Phe Arg
            155                 160                 165 cgg atg aag gag ttt gtc tca act gtg atg gag caa tta aaa aag tcc    642
```

```
                Arg Met Lys Glu Phe Val Ser Thr Val Met Glu Gln Leu Lys Lys Ser
                                170                 175                 180 aaa acc ttg ttc tct ttg atg cag tac tct gaa gaa ttc cgg att cac              690
Lys Thr Leu Phe Ser Leu Met Gln Tyr Ser Glu Glu Phe Arg Ile His
    185                 190                 195 ttt acc ttc aaa gag ttc cag aac aac cct aac cca aga tca ctg gtg              738
Phe Thr Phe Lys Glu Phe Gln Asn Asn Pro Asn Pro Arg Ser Leu Val
200                 205                 210                 215 aag cca ata acg cag ctg ctt ggg cgg aca cac acg gcc acg ggc atc              786
Lys Pro Ile Thr Gln Leu Leu Gly Arg Thr His Thr Ala Thr Gly Ile
                220                 225                 230 cgc aaa gtg gta cga gag ctg ttt aac atc acc aac gga gcc cga aag              834
Arg Lys Val Val Arg Glu Leu Phe Asn Ile Thr Asn Gly Ala Arg Lys
            235                 240                 245 aat gcc ttt aag atc cta gtt gtc atc acg gat gga gaa aag ttt ggc              882
Asn Ala Phe Lys Ile Leu Val Val Ile Thr Asp Gly Glu Lys Phe Gly
        250                 255                 260 gat ccc ttg gga tat gag gat gtc atc cct gag gca gac aga gag gga              930
Asp Pro Leu Gly Tyr Glu Asp Val Ile Pro Glu Ala Asp Arg Glu Gly
    265                 270                 275 gtc att cgc tac gtc att ggg gtg gga gat gcc ttc cgc agt gag aaa              978
Val Ile Arg Tyr Val Ile Gly Val Gly Asp Ala Phe Arg Ser Glu Lys
280                 285                 290                 295 tcc cgc caa gag ctt aat acc atc gca tcc aag ccg cct cgt gat cac             1026
Ser Arg Gln Glu Leu Asn Thr Ile Ala Ser Lys Pro Pro Arg Asp His
                300                 305                 310 gtg ttc cag gtg aat aac ttt gag gct ctg aag acc att cag aac cag             1074
Val Phe Gln Val Asn Asn Phe Glu Ala Leu Lys Thr Ile Gln Asn Gln
            315                 320                 325 ctt cgg gag aag atc ttt gcg atc gag ggt act cag aca gga agt agc             1122
Leu Arg Glu Lys Ile Phe Ala Ile Glu Gly Thr Gln Thr Gly Ser Ser
        330                 335                 340 agc tcc ttt gag cat gag atg tct cag gaa ggc ttc agc gct gcc atc             1170
Ser Ser Phe Glu His Glu Met Ser Gln Glu Gly Phe Ser Ala Ala Ile
    345                 350                 355 acc tct aat ggc ccc ttg ctg agc act gtg ggg agc tat gac tgg gct             1218
Thr Ser Asn Gly Pro Leu Leu Ser Thr Val Gly Ser Tyr Asp Trp Ala
360                 365                 370                 375 ggt gga gtc ttt cta tat aca tca aag gag aaa agc acc ttc atc aac             1266
Gly Gly Val Phe Leu Tyr Thr Ser Lys Glu Lys Ser Thr Phe Ile Asn
                380                 385                 390 atg acc aga gtg gat tca gac atg aat gat gct tac ttg ggt tat gct             1314
Met Thr Arg Val Asp Ser Asp Met Asn Asp Ala Tyr Leu Gly Tyr Ala
            395                 400                 405 gcc gcc atc atc tta cgg aac cgg gtg caa agc ctg gtt ctg ggg gca             1362
Ala Ala Ile Ile Leu Arg Asn Arg Val Gln Ser Leu Val Leu Gly Ala
        410                 415                 420 cct cga tat cag cac atc ggc ctg gta gcg atg ttc agg cag aac act             1410
Pro Arg Tyr Gln His Ile Gly Leu Val Ala Met Phe Arg Gln Asn Thr
    425                 430                 435 ggc atg tgg gag tcc aac gct aat gtc aag ggc acc cag atc ggc gcc             1458
Gly Met Trp Glu Ser Asn Ala Asn Val Lys Gly Thr Gln Ile Gly Ala
440                 445                 450                 455 tac ttc ggg gcc tcc ctc tgc tcc gtg gac gtg gac agc aac ggc agc             1506
Tyr Phe Gly Ala Ser Leu Cys Ser Val Asp Val Asp Ser Asn Gly Ser
                460                 465                 470 acc gac ctg gtc ctc atc ggg gcc ccc cat tac tac gag cag acc cga             1554
Thr Asp Leu Val Leu Ile Gly Ala Pro His Tyr Tyr Glu Gln Thr Arg
            475                 480                 485 ggg ggc cag gtg tcc gtg tgc ccc ttg ccc agg ggg agg gct cgg tgg             1602
```

```
Gly Gly Gln Val Ser Val Cys Pro Leu Pro Arg Gly Arg Ala Arg Trp
            490                 495                 500 cag tgt gat gct gtt ctc tac ggg gag cag ggc caa ccc tgg ggc cgc      1650
Gln Cys Asp Ala Val Leu Tyr Gly Glu Gln Gly Gln Pro Trp Gly Arg
        505                 510                 515 ttt ggg gca gcc cta aca gtg ctg ggg gac gta aat ggg gac aag ctg      1698
Phe Gly Ala Ala Leu Thr Val Leu Gly Asp Val Asn Gly Asp Lys Leu
520                 525                 530                 535 acg gac gtg gcc att ggg gcc cca gga gag gag gac aac cgg ggt gct      1746
Thr Asp Val Ala Ile Gly Ala Pro Gly Glu Glu Asp Asn Arg Gly Ala
                540                 545                 550 gtt tac ctg ttt cac gga acc tca gga tct ggc atc agc ccc tcc cat      1794
Val Tyr Leu Phe His Gly Thr Ser Gly Ser Gly Ile Ser Pro Ser His
            555                 560                 565 agc cag cgg ata gca ggc tcc aag ctc tct ccc agg ctc cag tat ttt      1842
Ser Gln Arg Ile Ala Gly Ser Lys Leu Ser Pro Arg Leu Gln Tyr Phe
        570                 575                 580 ggt cag tca ctg agt ggg ggc cag gac ctc aca atg gat gga ctg gta      1890
Gly Gln Ser Leu Ser Gly Gly Gln Asp Leu Thr Met Asp Gly Leu Val
585                 590                 595 gac ctg act gta gga gcc cag ggg cac gtg ctg ctc ctc agg tcc cag      1938
Asp Leu Thr Val Gly Ala Gln Gly His Val Leu Leu Leu Arg Ser Gln
600                 605                 610                 615 cca gta ctg aga gtc aag gca atc atg gag ttc aat ccc agg gaa gtg      1986
Pro Val Leu Arg Val Lys Ala Ile Met Glu Phe Asn Pro Arg Glu Val
            620                 625                 630 gca agg aat gta ttt gag tgt aat gat cag gtg gtg aaa ggc aag gaa      2034
Ala Arg Asn Val Phe Glu Cys Asn Asp Gln Val Val Lys Gly Lys Glu
        635                 640                 645 gcc gga gag gtc aga gtc tgc ctc cat gtc cag aag agc aca cgg gat      2082
Ala Gly Glu Val Arg Val Cys Leu His Val Gln Lys Ser Thr Arg Asp
650                 655                 660 cgg cta aga gaa gga cag atc cag agt gtt gtg act tat gac ctg gct      2130
Arg Leu Arg Glu Gly Gln Ile Gln Ser Val Val Thr Tyr Asp Leu Ala
665                 670                 675 ctg gac tcc ggc cgc cca cat tcc cgc gcc gtc ttc aat gag aca aag      2178
Leu Asp Ser Gly Arg Pro His Ser Arg Ala Val Phe Asn Glu Thr Lys
680                 685                 690                 695 aac agc aca cgc aga cag aca cag gtc ttg ggg ctg acc cag act tgt      2226
Asn Ser Thr Arg Arg Gln Thr Gln Val Leu Gly Leu Thr Gln Thr Cys
            700                 705                 710 gag acc ctg aaa cta cag ttg ccg aat tgc atc gag gac cca gtg agc      2274
Glu Thr Leu Lys Leu Gln Leu Pro Asn Cys Ile Glu Asp Pro Val Ser
        715                 720                 725 ccc att gtg ctg cgc ctg aac ttc tct ctg gtg gga acg cca ttg tct      2322
Pro Ile Val Leu Arg Leu Asn Phe Ser Leu Val Gly Thr Pro Leu Ser
730                 735                 740 gct ttc ggg aac ctc cgg cca gtg ctg gcg gag gat gct cag aga ctc      2370
Ala Phe Gly Asn Leu Arg Pro Val Leu Ala Glu Asp Ala Gln Arg Leu
745                 750                 755 ttc aca gcc ttg ttt ccc ttt gag aag aat tgt ggc aat gac aac atc      2418
Phe Thr Ala Leu Phe Pro Phe Glu Lys Asn Cys Gly Asn Asp Asn Ile
760                 765                 770                 775 tgc cag gat gac ctc agc atc acc ttc agt ttc atg agc ctg gac tgc      2466
Cys Gln Asp Asp Leu Ser Ile Thr Phe Ser Phe Met Ser Leu Asp Cys
            780                 785                 790 ctc gtg gtg ggt ggg ccc cgg gag ttc aac gtg aca gtg act gtg aga      2514
Leu Val Val Gly Gly Pro Arg Glu Phe Asn Val Thr Val Thr Val Arg
        795                 800                 805 aat gat ggt gag gac tcc tac agg aca cag gtc acc ttc ttc ttc ccg      2562
```

|  |  |  |  |  |  |  |  |  |  |  |  |  |  |  |  |
|---|---|---|---|---|---|---|---|---|---|---|---|---|---|---|---|
|  | Asn | Asp | Gly | Glu | Asp | Ser | Tyr | Arg | Thr | Gln | Val | Thr | Phe | Phe | Pro |
|  |  | 810 |  |  |  | 815 |  |  |  | 820 |  |  |  |  |  |

```
ctt gac ctg tcc tac cgg aag gtg tcc aca ctc cag aac cag cgc tca    2610
Leu Asp Leu Ser Tyr Arg Lys Val Ser Thr Leu Gln Asn Gln Arg Ser
825             830             835 cag cga tcc tgg cgc ctg gcc tgt gag tct gcc tcc tcc acc gaa gtg    2658
Gln Arg Ser Trp Arg Leu Ala Cys Glu Ser Ala Ser Ser Thr Glu Val
840             845             850             855 tct ggg gcc ttg aag agc acc agc tgc agc ata aac cac ccc atc ttc    2706
Ser Gly Ala Leu Lys Ser Thr Ser Cys Ser Ile Asn His Pro Ile Phe
            860             865             870 ccg gaa aac tca gag gtc acc ttt aat atc acg ttt gat gta gac tct    2754
Pro Glu Asn Ser Glu Val Thr Phe Asn Ile Thr Phe Asp Val Asp Ser
        875             880             885 aag gct tcc ctt gga aac aaa ctg ctc ctc aag gcc aat gtg acc agt    2802
Lys Ala Ser Leu Gly Asn Lys Leu Leu Leu Lys Ala Asn Val Thr Ser
    890             895             900 gag aac aac atg ccc aga acc aac aaa acc gaa ttc caa ctg gag ctg    2850
Glu Asn Asn Met Pro Arg Thr Asn Lys Thr Glu Phe Gln Leu Glu Leu
905             910             915 ccg gtg aaa tat gct gtc tac atg gtg gtc acc agc cat ggg gtc tcc    2898
Pro Val Lys Tyr Ala Val Tyr Met Val Val Thr Ser His Gly Val Ser
920             925             930             935 act aaa tat ctc aac ttc acg gcc tca gag aat acc agt cgg gtc atg    2946
Thr Lys Tyr Leu Asn Phe Thr Ala Ser Glu Asn Thr Ser Arg Val Met
            940             945             950 cag cat caa tat cag gtc agc aac ctg ggg cag agg agc ctc ccc atc    2994
Gln His Gln Tyr Gln Val Ser Asn Leu Gly Gln Arg Ser Leu Pro Ile
        955             960             965 agc ctg gtg ttc ttg gtg ccc gtc cgg ctg aac cag act gtc ata tgg    3042
Ser Leu Val Phe Leu Val Pro Val Arg Leu Asn Gln Thr Val Ile Trp
    970             975             980 gac cgc ccc cag gtc acc ttc tcc gag aac ctc tcg agt acg tgc cac    3090
Asp Arg Pro Gln Val Thr Phe Ser Glu Asn Leu Ser Ser Thr Cys His
985             990             995 acc aag gag cgc ttg ccc tct cac tcc gac ttt ctg gct gag ctt        3135
Thr Lys Glu Arg Leu Pro Ser His Ser Asp Phe Leu Ala Glu Leu
1000            1005            1010 cgg aag gcc ccc gtg gtg aac tgc tcc atc gct gtc tgc cag aga        3180
Arg Lys Ala Pro Val Val Asn Cys Ser Ile Ala Val Cys Gln Arg
1015            1020            1025 atc cag tgt gac atc ccg ttc ttt ggc atc cag gaa gaa ttc aat        3225
Ile Gln Cys Asp Ile Pro Phe Phe Gly Ile Gln Glu Glu Phe Asn
1030            1035            1040 gct acc ctc aaa ggc aac ctc tcg ttt gac tgg tac atc aag acc        3270
Ala Thr Leu Lys Gly Asn Leu Ser Phe Asp Trp Tyr Ile Lys Thr
1045            1050            1055 tcg cat aac cac ctc ctg atc gtg agc aca gct gag atc ttg ttt        3315
Ser His Asn His Leu Leu Ile Val Ser Thr Ala Glu Ile Leu Phe
1060            1065            1070 aac gat tcc gtg ttc acc ctg ctg ccg gga cag ggg gcg ttt gtg        3360
Asn Asp Ser Val Phe Thr Leu Leu Pro Gly Gln Gly Ala Phe Val
1075            1080            1085 agg tcc cag acg gag acc aaa gtg gag ccg ttc gag gtc ccc aac        3405
Arg Ser Gln Thr Glu Thr Lys Val Glu Pro Phe Glu Val Pro Asn
1090            1095            1100 ccc ctg ccg ctc atc gtg ggc agc tct gtc ggg gga ctg ctg ctc        3450
Pro Leu Pro Leu Ile Val Gly Ser Ser Val Gly Gly Leu Leu Leu
1105            1110            1115 ctg gcc ctc atc acc gcc gcg ctg tac aag ctc ggc ttc ttc aag        3495
```

```
Leu Ala Leu Ile Thr Ala Ala Leu Tyr Lys Leu Gly Phe Phe Lys
1120                1125                1130 cgg caa tac aag gac atg atg agt gaa ggg ggt ccc ccg ggg gcc       3540
Arg Gln Tyr Lys Asp Met Met Ser Glu Gly Gly Pro Pro Gly Ala
1135                1140                1145 gaa ccc cag tagcggctcc ttcccgacag agctgcctct cggtggccag           3589
Glu Pro Gln
1150 caggactctg cccagaccac acgagccccc aggctgcttt aattaaaagg gtgggcgcgc  3649 cgacccagct ttcttgtaca aagtggttga tctagagggc ccgcggttcg aaggtaagcc  3709 tatccctaac cctctcctcg gtctcgattc tacgcgtacc ggttagtaat gagtttaaac  3769 gggggaggct aactgaaaca cggaag                                      3795

<210> SEQ ID NO 12
<211> LENGTH: 1152
<212> TYPE: PRT
<213> ORGANISM: Homo sapiens

<400> SEQUENCE: 12

Met Ala Leu Arg Val Leu Leu Leu Thr Ala Leu Thr Leu Cys His Gly
1               5                   10                  15

Phe Asn Leu Asp Thr Glu Asn Ala Met Thr Phe Gln Glu Asn Ala Arg
            20                  25                  30

Gly Phe Gly Gln Ser Val Val Gln Leu Gln Gly Ser Arg Val Val Val
        35                  40                  45

Gly Ala Pro Gln Glu Ile Val Ala Ala Asn Gln Arg Gly Ser Leu Tyr
    50                  55                  60

Gln Cys Asp Tyr Ser Thr Gly Ser Cys Glu Pro Ile Arg Leu Gln Val
65                  70                  75                  80

Pro Val Glu Ala Val Asn Met Ser Leu Gly Leu Ser Leu Ala Ala Thr
                85                  90                  95

Thr Ser Pro Pro Gln Leu Leu Ala Cys Gly Pro Thr Val His Gln Thr
            100                 105                 110

Cys Ser Glu Asn Thr Tyr Val Lys Gly Leu Cys Phe Leu Phe Gly Ser
        115                 120                 125

Asn Leu Arg Gln Gln Pro Gln Lys Phe Pro Glu Ala Leu Arg Gly Cys
    130                 135                 140

Pro Gln Glu Asp Ser Asp Ile Ala Phe Leu Ile Asp Gly Ser Gly Ser
145                 150                 155                 160

Ile Ile Pro His Asp Phe Arg Arg Met Lys Glu Phe Val Ser Thr Val
                165                 170                 175

Met Glu Gln Leu Lys Lys Ser Lys Thr Leu Phe Ser Leu Met Gln Tyr
            180                 185                 190

Ser Glu Glu Phe Arg Ile His Phe Thr Phe Lys Glu Phe Gln Asn Asn
        195                 200                 205

Pro Asn Pro Arg Ser Leu Val Lys Pro Ile Thr Gln Leu Leu Gly Arg
    210                 215                 220

Thr His Thr Ala Thr Gly Ile Arg Lys Val Val Arg Glu Leu Phe Asn
225                 230                 235                 240

Ile Thr Asn Gly Ala Arg Lys Asn Ala Phe Lys Ile Leu Val Val Ile
                245                 250                 255

Thr Asp Gly Glu Lys Phe Gly Asp Pro Leu Gly Tyr Glu Asp Val Ile
            260                 265                 270

Pro Glu Ala Asp Arg Glu Gly Val Ile Arg Tyr Val Ile Gly Val Gly
        275                 280                 285
```

```
Asp Ala Phe Arg Ser Glu Lys Ser Arg Gln Glu Leu Asn Thr Ile Ala
    290                 295                 300

Ser Lys Pro Pro Arg Asp His Val Phe Gln Val Asn Asn Phe Glu Ala
305                 310                 315                 320

Leu Lys Thr Ile Gln Asn Gln Leu Arg Glu Lys Ile Phe Ala Ile Glu
            325                 330                 335

Gly Thr Gln Thr Gly Ser Ser Ser Phe Glu His Glu Met Ser Gln
            340                 345                 350

Glu Gly Phe Ser Ala Ala Ile Thr Ser Asn Gly Pro Leu Leu Ser Thr
        355                 360                 365

Val Gly Ser Tyr Asp Trp Ala Gly Gly Val Phe Leu Tyr Thr Ser Lys
    370                 375                 380

Glu Lys Ser Thr Phe Ile Asn Met Thr Arg Val Asp Ser Asp Met Asn
385                 390                 395                 400

Asp Ala Tyr Leu Gly Tyr Ala Ala Ala Ile Ile Leu Arg Asn Arg Val
            405                 410                 415

Gln Ser Leu Val Leu Gly Ala Pro Arg Tyr Gln His Ile Gly Leu Val
        420                 425                 430

Ala Met Phe Arg Gln Asn Thr Gly Met Trp Glu Ser Asn Ala Asn Val
    435                 440                 445

Lys Gly Thr Gln Ile Gly Ala Tyr Phe Gly Ala Ser Leu Cys Ser Val
450                 455                 460

Asp Val Asp Ser Asn Gly Ser Thr Asp Leu Val Leu Ile Gly Ala Pro
465                 470                 475                 480

His Tyr Tyr Glu Gln Thr Arg Gly Gly Gln Val Ser Val Cys Pro Leu
            485                 490                 495

Pro Arg Gly Arg Ala Arg Trp Gln Cys Asp Ala Val Leu Tyr Gly Glu
        500                 505                 510

Gln Gly Gln Pro Trp Gly Arg Phe Gly Ala Ala Leu Thr Val Leu Gly
    515                 520                 525

Asp Val Asn Gly Asp Lys Leu Thr Asp Val Ala Ile Gly Ala Pro Gly
530                 535                 540

Glu Glu Asp Asn Arg Gly Ala Val Tyr Leu Phe His Gly Thr Ser Gly
545                 550                 555                 560

Ser Gly Ile Ser Pro Ser His Ser Gln Arg Ile Ala Gly Ser Lys Leu
            565                 570                 575

Ser Pro Arg Leu Gln Tyr Phe Gly Gln Ser Leu Ser Gly Gly Gln Asp
        580                 585                 590

Leu Thr Met Asp Gly Leu Val Asp Leu Thr Val Gly Ala Gln Gly His
    595                 600                 605

Val Leu Leu Leu Arg Ser Gln Pro Val Leu Arg Val Lys Ala Ile Met
    610                 615                 620

Glu Phe Asn Pro Arg Glu Val Ala Arg Asn Val Phe Glu Cys Asn Asp
625                 630                 635                 640

Gln Val Val Lys Gly Lys Glu Ala Gly Glu Val Arg Val Cys Leu His
            645                 650                 655

Val Gln Lys Ser Thr Arg Asp Arg Leu Arg Glu Gly Gln Ile Gln Ser
        660                 665                 670

Val Val Thr Tyr Asp Leu Ala Leu Asp Ser Gly Arg Pro His Ser Arg
    675                 680                 685

Ala Val Phe Asn Glu Thr Lys Asn Ser Thr Arg Arg Gln Thr Gln Val
    690                 695                 700

Leu Gly Leu Thr Gln Thr Cys Glu Thr Leu Lys Leu Gln Leu Pro Asn
```

-continued

```
            705                 710                 715                 720
Cys Ile Glu Asp Pro Val Ser Pro Ile Val Arg Leu Asn Phe Ser
                    725                 730                 735
Leu Val Gly Thr Pro Leu Ser Ala Phe Gly Asn Leu Arg Pro Val Leu
                    740                 745                 750
Ala Glu Asp Ala Gln Arg Leu Phe Thr Ala Leu Phe Pro Phe Glu Lys
                    755                 760                 765
Asn Cys Gly Asn Asp Asn Ile Cys Gln Asp Asp Leu Ser Ile Thr Phe
                    770                 775                 780
Ser Phe Met Ser Leu Asp Cys Leu Val Val Gly Gly Pro Arg Glu Phe
785                 790                 795                 800
Asn Val Thr Val Thr Val Arg Asn Asp Gly Glu Asp Ser Tyr Arg Thr
                    805                 810                 815
Gln Val Thr Phe Phe Pro Leu Asp Leu Ser Tyr Arg Lys Val Ser
                    820                 825                 830
Thr Leu Gln Asn Gln Arg Ser Gln Arg Ser Trp Arg Leu Ala Cys Glu
                    835                 840                 845
Ser Ala Ser Ser Thr Glu Val Ser Gly Ala Leu Lys Ser Thr Ser Cys
                    850                 855                 860
Ser Ile Asn His Pro Ile Phe Pro Glu Asn Ser Glu Val Thr Phe Asn
865                 870                 875                 880
Ile Thr Phe Asp Val Asp Ser Lys Ala Ser Leu Gly Asn Lys Leu Leu
                    885                 890                 895
Leu Lys Ala Asn Val Thr Ser Glu Asn Asn Met Pro Arg Thr Asn Lys
                    900                 905                 910
Thr Glu Phe Gln Leu Glu Leu Pro Val Lys Tyr Ala Val Tyr Met Val
                    915                 920                 925
Val Thr Ser His Gly Val Ser Thr Lys Tyr Leu Asn Phe Thr Ala Ser
                    930                 935                 940
Glu Asn Thr Ser Arg Val Met Gln His Gln Tyr Gln Val Ser Asn Leu
945                 950                 955                 960
Gly Gln Arg Ser Leu Pro Ile Ser Leu Val Phe Leu Val Pro Val Arg
                    965                 970                 975
Leu Asn Gln Thr Val Ile Trp Asp Arg Pro Gln Val Thr Phe Ser Glu
                    980                 985                 990
Asn Leu Ser Ser Thr Cys His Thr Lys Glu Arg Leu Pro Ser His Ser
                    995                1000                1005
Asp Phe Leu Ala Glu Leu Arg Lys Ala Pro Val Val Asn Cys Ser
                   1010                1015                1020
Ile Ala Val Cys Gln Arg Ile Gln Cys Asp Ile Pro Phe Phe Gly
                   1025                1030                1035
Ile Gln Glu Glu Phe Asn Ala Thr Leu Lys Gly Asn Leu Ser Phe
                   1040                1045                1050
Asp Trp Tyr Ile Lys Thr Ser His Asn His Leu Leu Ile Val Ser
                   1055                1060                1065
Thr Ala Glu Ile Leu Phe Asn Asp Ser Val Phe Thr Leu Leu Pro
                   1070                1075                1080
Gly Gln Gly Ala Phe Val Arg Ser Gln Thr Glu Thr Lys Val Glu
                   1085                1090                1095
Pro Phe Glu Val Pro Asn Pro Leu Pro Leu Ile Val Gly Ser Ser
                   1100                1105                1110
Val Gly Gly Leu Leu Leu Leu Ala Leu Ile Thr Ala Ala Leu Tyr
                   1115                1120                1125
```

```
                Lys Leu Gly Phe Phe Lys Arg Gln Tyr Lys Asp Met Met Ser Glu
                    1130                1135                1140

Gly Gly Pro Pro Gly Ala Glu Pro Gln
                    1145                1150

<210> SEQ ID NO 13
<211> LENGTH: 3836
<212> TYPE: DNA
<213> ORGANISM: Homo sapiens
<220> FEATURE:
<221> NAME/KEY: CDS
<222> LOCATION: (186)..(3641)
<223> OTHER INFORMATION:

<400> SEQUENCE: 13
caaatgggcg gtaggcgtgt acggtgggag gtctatataa gcagagctct ctggctaact      60
agagaaccca ctgcttactg gcttatcgaa attaatacga ctcactatag ggagacccaa     120
gctggctagt taagctatca acaagtttgt acaaaaaagc aggctccgcg gccgcccccct   180 tcacc atg gct ctc aga gtc ctt ctg tta aca gcc ttg acc tta tgt cat     230
      Met Ala Leu Arg Val Leu Leu Leu Thr Ala Leu Thr Leu Cys His
        1               5                  10                  15 ggg ttc aac ttg gac act gaa aac gca atg acc ttc caa gag aac gca       278
Gly Phe Asn Leu Asp Thr Glu Asn Ala Met Thr Phe Gln Glu Asn Ala
                 20                  25                  30 agg ggc ttc ggg cag agc gtg gtc cag ctt cag gga tcc agg gtg gtg       326
Arg Gly Phe Gly Gln Ser Val Val Gln Leu Gln Gly Ser Arg Val Val
             35                  40                  45 gtt gga gcc ccc cag gag ata gtg gct gcc aac caa agg ggc agc ctc       374
Val Gly Ala Pro Gln Glu Ile Val Ala Ala Asn Gln Arg Gly Ser Leu
         50                  55                  60 tac cag tgc gac tac agc aca ggc tca tgc gag ccc atc cac ctg cag       422
Tyr Gln Cys Asp Tyr Ser Thr Gly Ser Cys Glu Pro Ile His Leu Gln
     65                  70                  75 gtc ccc gtg gag gcc gtg aac atg tcc ctg ggc ctg tcc ctg gca gcc       470
Val Pro Val Glu Ala Val Asn Met Ser Leu Gly Leu Ser Leu Ala Ala
 80                  85                  90                  95 acc acc agc ccc cct cag ctg ctg gcc tgt ggt ccc acc gtg cac cag       518
Thr Thr Ser Pro Pro Gln Leu Leu Ala Cys Gly Pro Thr Val His Gln
                100                 105                 110 act tgc agt gag aac acg tat gtg aaa ggg ctc tgc ttc ctg ttt gga       566
Thr Cys Ser Glu Asn Thr Tyr Val Lys Gly Leu Cys Phe Leu Phe Gly
             115                 120                 125 tcc aac cta cgg cag cag ccc cag aag ttc cca gag gcc ctc cga ggg       614
Ser Asn Leu Arg Gln Gln Pro Gln Lys Phe Pro Glu Ala Leu Arg Gly
         130                 135                 140 tgt cct caa gag gat agt gac att gcc ttc ttg att gat ggc tct ggt       662
Cys Pro Gln Glu Asp Ser Asp Ile Ala Phe Leu Ile Asp Gly Ser Gly
     145                 150                 155 agc atc atc cca cat gac ttt cgg cgg atg aag gag ttt gtc tca act       710
Ser Ile Ile Pro His Asp Phe Arg Arg Met Lys Glu Phe Val Ser Thr
 160                 165                 170                 175 gtg atg gag caa tta aaa aag tcc aaa acc ttg ttc tct ttg atg cag       758
Val Met Glu Gln Leu Lys Lys Ser Lys Thr Leu Phe Ser Leu Met Gln
                180                 185                 190 tac tct gaa gaa ttc cgg att cac ttt acc ttc aaa gag ttc cag aac       806
Tyr Ser Glu Glu Phe Arg Ile His Phe Thr Phe Lys Glu Phe Gln Asn
             195                 200                 205 aac cct aac cca aga tca ctg gtg aag cca ata acg cag ctg ctt ggg       854
Asn Pro Asn Pro Arg Ser Leu Val Lys Pro Ile Thr Gln Leu Leu Gly
         210                 215                 220
```

```
cgg aca cac acg gcc acg ggc atc cgc aaa gtg gta cga gag ctg ttt    902
Arg Thr His Thr Ala Thr Gly Ile Arg Lys Val Val Arg Glu Leu Phe
    225                 230                 235 aac atc acc aac gga gcc cga aag aat gcc ttt aag atc cta gtt gtc    950
Asn Ile Thr Asn Gly Ala Arg Lys Asn Ala Phe Lys Ile Leu Val Val
240                 245                 250                 255 atc acg gat gga gaa aag ttt ggc gat ccc ttg gga tat gag gat gtc    998
Ile Thr Asp Gly Glu Lys Phe Gly Asp Pro Leu Gly Tyr Glu Asp Val
                260                 265                 270 atc cct gag gca gac aga gag gga gtc att cgc tac gtc att ggg gtg   1046
Ile Pro Glu Ala Asp Arg Glu Gly Val Ile Arg Tyr Val Ile Gly Val
            275                 280                 285 gga gat gcc ttc cgc agt gag aaa tcc cgc caa gag ctt aat acc atc   1094
Gly Asp Ala Phe Arg Ser Glu Lys Ser Arg Gln Glu Leu Asn Thr Ile
        290                 295                 300 gca tcc aag ccg cct cgt gat cac gtg ttc cag gtg aat aac ttt gag   1142
Ala Ser Lys Pro Pro Arg Asp His Val Phe Gln Val Asn Asn Phe Glu
    305                 310                 315 gct ctg aag acc att cag aac cag ctt cgg gag aag atc ttt gcg atc   1190
Ala Leu Lys Thr Ile Gln Asn Gln Leu Arg Glu Lys Ile Phe Ala Ile
320                 325                 330                 335 gag ggt act cag aca gga agt agc agc tcc ttt gag cat gag atg tct   1238
Glu Gly Thr Gln Thr Gly Ser Ser Ser Ser Phe Glu His Glu Met Ser
                340                 345                 350 cag gaa ggc ttc agc gct gcc atc acc tct aat ggc ccc ttg ctg agc   1286
Gln Glu Gly Phe Ser Ala Ala Ile Thr Ser Asn Gly Pro Leu Leu Ser
            355                 360                 365 act gtg ggg agc tat gac tgg gct ggt gga gtc ttt cta tat aca tca   1334
Thr Val Gly Ser Tyr Asp Trp Ala Gly Gly Val Phe Leu Tyr Thr Ser
        370                 375                 380 aag gag aaa agc acc ttc atc aac atg acc aga gtg gat tca gac atg   1382
Lys Glu Lys Ser Thr Phe Ile Asn Met Thr Arg Val Asp Ser Asp Met
    385                 390                 395 aat gat gct tac ttg ggt tat gct gcc gcc atc atc tta cgg aac cgg   1430
Asn Asp Ala Tyr Leu Gly Tyr Ala Ala Ala Ile Ile Leu Arg Asn Arg
400                 405                 410                 415 gtg caa agc ctg gtt ctg ggg gca cct cga tat cag cac atc ggc ctg   1478
Val Gln Ser Leu Val Leu Gly Ala Pro Arg Tyr Gln His Ile Gly Leu
                420                 425                 430 gta gcg atg ttc agg cag aac act ggc atg tgg gag tcc aac gct aat   1526
Val Ala Met Phe Arg Gln Asn Thr Gly Met Trp Glu Ser Asn Ala Asn
            435                 440                 445 gtc aag ggc acc cag atc ggc gcc tac ttc ggg gcc tcc ctc tgc tcc   1574
Val Lys Gly Thr Gln Ile Gly Ala Tyr Phe Gly Ala Ser Leu Cys Ser
        450                 455                 460 gtg gac gtg gac agc aac ggc agc acc gac ctg gtc ctc atc ggg gcc   1622
Val Asp Val Asp Ser Asn Gly Ser Thr Asp Leu Val Leu Ile Gly Ala
    465                 470                 475 ccc cat tac tac gag cag acc cga ggg ggc cag gtg tcc gtg tgc ccc   1670
Pro His Tyr Tyr Glu Gln Thr Arg Gly Gly Gln Val Ser Val Cys Pro
480                 485                 490                 495 ttg ccc agg ggg agg gct cgg tgg cag tgt gat gct gtt ctc tac ggg   1718
Leu Pro Arg Gly Arg Ala Arg Trp Gln Cys Asp Ala Val Leu Tyr Gly
                500                 505                 510 gag cag ggc caa ccc tgg ggc cgc ttt ggg gca gcc cta aca gtg ctg   1766
Glu Gln Gly Gln Pro Trp Gly Arg Phe Gly Ala Ala Leu Thr Val Leu
            515                 520                 525 ggg gac gta aat ggg gac aag ctg acg gac gtg gcc att ggg gcc cca   1814
Gly Asp Val Asn Gly Asp Lys Leu Thr Asp Val Ala Ile Gly Ala Pro
        530                 535                 540
```

```
                                                        -continued
gga gag gag gac aac cgg ggt gct gtt tac ctg ttt cac gga acc tca        1862
Gly Glu Glu Asp Asn Arg Gly Ala Val Tyr Leu Phe His Gly Thr Ser
        545                 550                 555 gga tct ggc atc agc ccc tcc cat agc cag cgg ata gca ggc tcc aag        1910
Gly Ser Gly Ile Ser Pro Ser His Ser Gln Arg Ile Ala Gly Ser Lys
560                 565                 570                 575 ctc tct ccc agg ctc cag tat ttt ggt cag tca ctg agt ggg ggc cag        1958
Leu Ser Pro Arg Leu Gln Tyr Phe Gly Gln Ser Leu Ser Gly Gly Gln
                    580                 585                 590 gac ctc aca atg gat gga ctg gta gac ctg act gta gga gcc cag ggg        2006
Asp Leu Thr Met Asp Gly Leu Val Asp Leu Thr Val Gly Ala Gln Gly
                595                 600                 605 cac gtg ctg ctg ctc agg tcc cag cca gta ctg aga gtc aag gca atc        2054
His Val Leu Leu Leu Arg Ser Gln Pro Val Leu Arg Val Lys Ala Ile
        610                 615                 620 atg gag ttc aat ccc agg gaa gtg gca agg aat gta ttt gag tgt aat        2102
Met Glu Phe Asn Pro Arg Glu Val Ala Arg Asn Val Phe Glu Cys Asn
625                 630                 635 gat cag gtg gtg aaa ggc aag gaa gcc gga gag gtc aga gtc tgc ctc        2150
Asp Gln Val Val Lys Gly Lys Glu Ala Gly Glu Val Arg Val Cys Leu
640                 645                 650                 655 cat gtc cag aag agc aca cgg gat cgg cta aga gaa gga cag atc cag        2198
His Val Gln Lys Ser Thr Arg Asp Arg Leu Arg Glu Gly Gln Ile Gln
                    660                 665                 670 agt gtt gtg act tat gac ctg gct ctg gac tcc ggc cgc cca cat tcc        2246
Ser Val Val Thr Tyr Asp Leu Ala Leu Asp Ser Gly Arg Pro His Ser
                675                 680                 685 cgc gcc gtc ttc aat gag aca aag aac agc aca cgc aga cag aca cag        2294
Arg Ala Val Phe Asn Glu Thr Lys Asn Ser Thr Arg Arg Gln Thr Gln
        690                 695                 700 gtc ttg ggg ctg acc cag act tgt gag acc ctg aaa cta cag ttg ccg        2342
Val Leu Gly Leu Thr Gln Thr Cys Glu Thr Leu Lys Leu Gln Leu Pro
705                 710                 715 aat tgc atc gag gac cca gtg agc ccc att gtg ctg cgc ctg aac ttc        2390
Asn Cys Ile Glu Asp Pro Val Ser Pro Ile Val Leu Arg Leu Asn Phe
720                 725                 730                 735 tct ctg gtg gga acg cca ttg tct gct ttc ggg aac ctc cgg cca gtg        2438
Ser Leu Val Gly Thr Pro Leu Ser Ala Phe Gly Asn Leu Arg Pro Val
                    740                 745                 750 ctg gcg gag gat gct cag aga ctc ttc aca gcc ttg ttt ccc ttt gag        2486
Leu Ala Glu Asp Ala Gln Arg Leu Phe Thr Ala Leu Phe Pro Phe Glu
                755                 760                 765 aag aat tgt ggc aat gac aac atc tgc cag gat gac ctc agc atc acc        2534
Lys Asn Cys Gly Asn Asp Asn Ile Cys Gln Asp Asp Leu Ser Ile Thr
        770                 775                 780 ttc agt ttc atg agc ctg gac tgc ctc gtg gtg ggt ggg ccc cgg gag        2582
Phe Ser Phe Met Ser Leu Asp Cys Leu Val Val Gly Gly Pro Arg Glu
785                 790                 795 ttc aac gtg aca gtg act gtg aga aat gat ggt gag gac tcc tac agg        2630
Phe Asn Val Thr Val Thr Val Arg Asn Asp Gly Glu Asp Ser Tyr Arg
800                 805                 810                 815 aca cag gtc acc ttc ttc ttc ccg ctt gac ctg tcc tac cgg aag gtg        2678
Thr Gln Val Thr Phe Phe Phe Pro Leu Asp Leu Ser Tyr Arg Lys Val
                    820                 825                 830 tcc aca ctc cag aac cag cgc tca cag cga tcc tgg cgc ctg gcc tgt        2726
Ser Thr Leu Gln Asn Gln Arg Ser Gln Arg Ser Trp Arg Leu Ala Cys
                835                 840                 845 gag tct gcc tcc tcc acc gaa gtg tct ggg gcc ttg aag agc acc agc        2774
Glu Ser Ala Ser Ser Thr Glu Val Ser Gly Ala Leu Lys Ser Thr Ser
        850                 855                 860
```

```
tgc agc ata aac cac ccc atc ttc ccg gaa aac tca gag gtc acc ttt      2822
Cys Ser Ile Asn His Pro Ile Phe Pro Glu Asn Ser Glu Val Thr Phe
    865                 870                 875 aat atc acg ttt gat gta gac tct aag gct tcc ctt gga aac aaa ctg      2870
Asn Ile Thr Phe Asp Val Asp Ser Lys Ala Ser Leu Gly Asn Lys Leu
880                 885                 890                 895 ctc ctc aag gcc aat gtg acc agt gag aac aac atg ccc aga acc aac      2918
Leu Leu Lys Ala Asn Val Thr Ser Glu Asn Asn Met Pro Arg Thr Asn
                900                 905                 910 aaa acc gaa ttc caa ctg gag ctg ccg gtg aaa tat gct gtc tac atg      2966
Lys Thr Glu Phe Gln Leu Glu Leu Pro Val Lys Tyr Ala Val Tyr Met
            915                 920                 925 gtg gtc acc agc cat ggg gtc tcc act aaa tat ctc aac ttc acg gcc      3014
Val Val Thr Ser His Gly Val Ser Thr Lys Tyr Leu Asn Phe Thr Ala
        930                 935                 940 tca gag aat acc agt cgg gtc atg cag cat caa tat cag gtc agc aac      3062
Ser Glu Asn Thr Ser Arg Val Met Gln His Gln Tyr Gln Val Ser Asn
    945                 950                 955 ctg ggg cag agg agc ctc ccc atc agc ctg gtg ttc ttg gtg ccc gtc      3110
Leu Gly Gln Arg Ser Leu Pro Ile Ser Leu Val Phe Leu Val Pro Val
960                 965                 970                 975 cgg ctg aac cag act gtc ata tgg gac cgc ccc cag gtc acc ttc tcc      3158
Arg Leu Asn Gln Thr Val Ile Trp Asp Arg Pro Gln Val Thr Phe Ser
                980                 985                 990 gag aac ctc tcg agt acg tgc cac acc aag gag cgc ttg ccc tct cac      3206
Glu Asn Leu Ser Ser Thr Cys His Thr Lys Glu Arg Leu Pro Ser His
            995                1000                1005 tcc gac ttt ctg gct gag ctt cgg aag gcc ccc gtg gtg aac tgc           3251
Ser Asp Phe Leu Ala Glu Leu Arg Lys Ala Pro Val Val Asn Cys
        1010                1015                1020 tcc atc gct gtc tgc cag aga atc cag tgt gac atc ccg ttc ttt          3296
Ser Ile Ala Val Cys Gln Arg Ile Gln Cys Asp Ile Pro Phe Phe
    1025                1030                1035 ggc atc cag gaa gaa ttc aat gct acc ctc aaa ggc aac ctc tcg          3341
Gly Ile Gln Glu Glu Phe Asn Ala Thr Leu Lys Gly Asn Leu Ser
1040                1045                1050 ttt gac tgg tac atc aag acc tcg cat aac cac ctc ctg atc gtg          3386
Phe Asp Trp Tyr Ile Lys Thr Ser His Asn His Leu Leu Ile Val
        1055                1060                1065 agc aca gct gag atc ttg ttt aac gat tcc gtg ttc acc ctg ctg          3431
Ser Thr Ala Glu Ile Leu Phe Asn Asp Ser Val Phe Thr Leu Leu
    1070                1075                1080 ccg gga cag ggg gcg ttt gtg agg tcc cag acg gag acc aaa gtg          3476
Pro Gly Gln Gly Ala Phe Val Arg Ser Gln Thr Glu Thr Lys Val
1085                1090                1095 gag ccg ttc gag gtc ccc aac ccc ctg ccg ctc atc gtg ggc agc          3521
Glu Pro Phe Glu Val Pro Asn Pro Leu Pro Leu Ile Val Gly Ser
        1100                1105                1110 tct gtc ggg gga ctg ctg ctc ctg gcc ctc atc acc gcc gcg ctg          3566
Ser Val Gly Gly Leu Leu Leu Leu Ala Leu Ile Thr Ala Ala Leu
    1115                1120                1125 tac aag ctc ggc ttc ttc aag cgg caa tac aag gac atg atg agt          3611
Tyr Lys Leu Gly Phe Phe Lys Arg Gln Tyr Lys Asp Met Met Ser
1130                1135                1140 gaa ggg ggt ccc ccg ggg gcc gaa ccc cag tagcggctcc ttcccgacag        3661
Glu Gly Gly Pro Pro Gly Ala Glu Pro Gln
1145                1150 agctgcctct cggtggccag caggactctg cccagaccac acgagccccc aggctgcttt    3721
aattaaaagg gtgggcgcgc cgacccagct ttcttgtaca aagtggttga tctagagggc    3781
```
ccgcggttcg aaggtaagcc tatccctaac cctctcctcg gtctcgattc tacgc    3836

<210> SEQ ID NO 14
<211> LENGTH: 1152
<212> TYPE: PRT
<213> ORGANISM: Homo sapiens

<400> SEQUENCE: 14

```
Met Ala Leu Arg Val Leu Leu Thr Ala Leu Thr Leu Cys His Gly
1               5                   10                  15

Phe Asn Leu Asp Thr Glu Asn Ala Met Thr Phe Gln Glu Asn Ala Arg
            20                  25                  30

Gly Phe Gly Gln Ser Val Val Gln Leu Gln Gly Ser Arg Val Val Val
        35                  40                  45

Gly Ala Pro Gln Glu Ile Val Ala Ala Asn Gln Arg Gly Ser Leu Tyr
    50                  55                  60

Gln Cys Asp Tyr Ser Thr Gly Ser Cys Glu Pro Ile His Leu Gln Val
65                  70                  75                  80

Pro Val Glu Ala Val Asn Met Ser Leu Gly Leu Ser Leu Ala Ala Thr
                85                  90                  95

Thr Ser Pro Pro Gln Leu Leu Ala Cys Gly Pro Thr Val His Gln Thr
            100                 105                 110

Cys Ser Glu Asn Thr Tyr Val Lys Gly Leu Cys Phe Leu Phe Gly Ser
        115                 120                 125

Asn Leu Arg Gln Gln Pro Gln Lys Phe Pro Glu Ala Leu Arg Gly Cys
    130                 135                 140

Pro Gln Glu Asp Ser Asp Ile Ala Phe Leu Ile Asp Gly Ser Gly Ser
145                 150                 155                 160

Ile Ile Pro His Asp Phe Arg Arg Met Lys Glu Phe Val Ser Thr Val
                165                 170                 175

Met Glu Gln Leu Lys Lys Ser Lys Thr Leu Phe Ser Leu Met Gln Tyr
            180                 185                 190

Ser Glu Glu Phe Arg Ile His Phe Thr Phe Lys Glu Phe Gln Asn Asn
        195                 200                 205

Pro Asn Pro Arg Ser Leu Val Lys Pro Ile Thr Gln Leu Leu Gly Arg
    210                 215                 220

Thr His Thr Ala Thr Gly Ile Arg Lys Val Val Arg Glu Leu Phe Asn
225                 230                 235                 240

Ile Thr Asn Gly Ala Arg Lys Asn Ala Phe Lys Ile Leu Val Val Ile
                245                 250                 255

Thr Asp Gly Glu Lys Phe Gly Asp Pro Leu Gly Tyr Glu Asp Val Ile
            260                 265                 270

Pro Glu Ala Asp Arg Glu Gly Val Ile Arg Tyr Val Ile Gly Val Gly
        275                 280                 285

Asp Ala Phe Arg Ser Glu Lys Ser Arg Gln Glu Leu Asn Thr Ile Ala
    290                 295                 300

Ser Lys Pro Pro Arg Asp His Val Phe Gln Val Asn Asn Phe Glu Ala
305                 310                 315                 320

Leu Lys Thr Ile Gln Asn Gln Leu Arg Glu Lys Ile Phe Ala Ile Glu
                325                 330                 335

Gly Thr Gln Thr Gly Ser Ser Ser Phe Glu His Glu Met Ser Gln
            340                 345                 350

Glu Gly Phe Ser Ala Ala Ile Thr Ser Asn Gly Pro Leu Leu Ser Thr
        355                 360                 365

Val Gly Ser Tyr Asp Trp Ala Gly Gly Val Phe Leu Tyr Thr Ser Lys
```

```
                    370             375             380
Glu Lys Ser Thr Phe Ile Asn Met Thr Arg Val Asp Ser Asp Met Asn
385                 390             395                 400

Asp Ala Tyr Leu Gly Tyr Ala Ala Ile Ile Leu Arg Asn Arg Val
                405             410             415

Gln Ser Leu Val Leu Gly Ala Pro Arg Tyr Gln His Ile Gly Leu Val
                420             425             430

Ala Met Phe Arg Gln Asn Thr Gly Met Trp Glu Ser Asn Ala Asn Val
            435             440             445

Lys Gly Thr Gln Ile Gly Ala Tyr Phe Gly Ala Ser Leu Cys Ser Val
450             455             460

Asp Val Asp Ser Asn Gly Ser Thr Asp Leu Val Leu Ile Gly Ala Pro
465             470             475             480

His Tyr Tyr Glu Gln Thr Arg Gly Gly Gln Val Ser Val Cys Pro Leu
                485             490             495

Pro Arg Gly Arg Ala Arg Trp Gln Cys Asp Ala Val Leu Tyr Gly Glu
                500             505             510

Gln Gly Gln Pro Trp Gly Arg Phe Gly Ala Ala Leu Thr Val Leu Gly
                515             520             525

Asp Val Asn Gly Asp Lys Leu Thr Asp Val Ala Ile Gly Ala Pro Gly
530             535             540

Glu Glu Asp Asn Arg Gly Ala Val Tyr Leu Phe His Gly Thr Ser Gly
545             550             555             560

Ser Gly Ile Ser Pro Ser His Ser Gln Arg Ile Ala Gly Ser Lys Leu
                565             570             575

Ser Pro Arg Leu Gln Tyr Phe Gly Gln Ser Leu Ser Gly Gly Gln Asp
                580             585             590

Leu Thr Met Asp Gly Leu Val Asp Leu Thr Val Gly Ala Gln Gly His
            595             600             605

Val Leu Leu Leu Arg Ser Gln Pro Val Leu Arg Val Lys Ala Ile Met
            610             615             620

Glu Phe Asn Pro Arg Glu Val Ala Arg Asn Val Phe Glu Cys Asn Asp
625             630             635             640

Gln Val Val Lys Gly Lys Glu Ala Gly Glu Val Arg Val Cys Leu His
                645             650             655

Val Gln Lys Ser Thr Arg Asp Arg Leu Arg Glu Gly Gln Ile Gln Ser
                660             665             670

Val Val Thr Tyr Asp Leu Ala Leu Asp Ser Gly Arg Pro His Ser Arg
            675             680             685

Ala Val Phe Asn Glu Thr Lys Asn Ser Thr Arg Arg Gln Thr Gln Val
            690             695             700

Leu Gly Leu Thr Gln Thr Cys Glu Thr Leu Lys Leu Gln Leu Pro Asn
705             710             715             720

Cys Ile Glu Asp Pro Val Ser Pro Ile Val Leu Arg Leu Asn Phe Ser
                725             730             735

Leu Val Gly Thr Pro Leu Ser Ala Phe Gly Asn Leu Arg Pro Val Leu
                740             745             750

Ala Glu Asp Ala Gln Arg Leu Phe Thr Ala Leu Phe Pro Phe Glu Lys
            755             760             765

Asn Cys Gly Asn Asp Asn Ile Cys Gln Asp Asp Leu Ser Ile Thr Phe
            770             775             780

Ser Phe Met Ser Leu Asp Cys Leu Val Val Gly Gly Pro Arg Glu Phe
785             790             795             800
```

| | | | | | | | | | | | | |
|---|---|---|---|---|---|---|---|---|---|---|---|---|
|Asn|Val|Thr|Val|Thr|Val|Arg|Asn|Asp|Gly|Glu|Asp|Ser|Tyr|Arg|Thr|
| | | |805| | | |810| | | |815| |

Gln Val Thr Phe Phe Pro Leu Asp Leu Ser Tyr Arg Lys Val Ser
              820                 825                 830

Thr Leu Gln Asn Gln Arg Ser Gln Arg Ser Trp Arg Leu Ala Cys Glu
        835                 840                 845

Ser Ala Ser Ser Thr Glu Val Ser Gly Ala Leu Lys Ser Thr Ser Cys
    850                 855                 860

Ser Ile Asn His Pro Ile Phe Pro Glu Asn Ser Glu Val Thr Phe Asn
865                 870                 875                 880

Ile Thr Phe Asp Val Asp Ser Lys Ala Ser Leu Gly Asn Lys Leu Leu
            885                 890                 895

Leu Lys Ala Asn Val Thr Ser Glu Asn Asn Met Pro Arg Thr Asn Lys
        900                 905                 910

Thr Glu Phe Gln Leu Glu Leu Pro Val Lys Tyr Ala Val Tyr Met Val
    915                 920                 925

Val Thr Ser His Gly Val Ser Thr Lys Tyr Leu Asn Phe Thr Ala Ser
    930                 935                 940

Glu Asn Thr Ser Arg Val Met Gln His Gln Tyr Gln Val Ser Asn Leu
945                 950                 955                 960

Gly Gln Arg Ser Leu Pro Ile Ser Leu Val Phe Leu Val Pro Val Arg
            965                 970                 975

Leu Asn Gln Thr Val Ile Trp Asp Arg Pro Gln Val Thr Phe Ser Glu
        980                 985                 990

Asn Leu Ser Ser Thr Cys His Thr Lys Glu Arg Leu Pro Ser His Ser
    995                 1000                1005

Asp Phe Leu Ala Glu Leu Arg Lys Ala Pro Val Val Asn Cys Ser
    1010                1015                1020

Ile Ala Val Cys Gln Arg Ile Gln Cys Asp Ile Pro Phe Phe Gly
    1025                1030                1035

Ile Gln Glu Glu Phe Asn Ala Thr Leu Lys Gly Asn Leu Ser Phe
    1040                1045                1050

Asp Trp Tyr Ile Lys Thr Ser His Asn His Leu Leu Ile Val Ser
    1055                1060                1065

Thr Ala Glu Ile Leu Phe Asn Asp Ser Val Phe Thr Leu Leu Pro
    1070                1075                1080

Gly Gln Gly Ala Phe Val Arg Ser Gln Thr Glu Thr Lys Val Glu
    1085                1090                1095

Pro Phe Glu Val Pro Asn Pro Leu Pro Leu Ile Val Gly Ser Ser
    1100                1105                1110

Val Gly Gly Leu Leu Leu Leu Ala Leu Ile Thr Ala Ala Leu Tyr
    1115                1120                1125

Lys Leu Gly Phe Phe Lys Arg Gln Tyr Lys Asp Met Met Ser Glu
    1130                1135                1140

Gly Gly Pro Pro Gly Ala Glu Pro Gln
    1145                1150

<210> SEQ ID NO 15
<211> LENGTH: 2610
<212> TYPE: DNA
<213> ORGANISM: Homo sapiens
<220> FEATURE:
<221> NAME/KEY: CDS
<222> LOCATION: (94)..(2400)
<223> OTHER INFORMATION:

<400> SEQUENCE: 15

```
taatacgact cactataggg agacccaagc tggctagtta agctatcaac aagtttgtac      60
aaaaaagcag gctccgcggc cgccccttc acc atg ctg ggc ctg cgc ccc cca      114
                                  Met Leu Gly Leu Arg Pro Pro
                                  1               5 ctg ctc gcc ctg gtg ggg ctg ctc tcc ctc ggg tgc gtc ctc tct cag      162
Leu Leu Ala Leu Val Gly Leu Leu Ser Leu Gly Cys Val Leu Ser Gln
        10              15              20 gag tgc acg aag ttc aag gtc agc agc tgc cgg gaa tgc atc gag tcg      210
Glu Cys Thr Lys Phe Lys Val Ser Ser Cys Arg Glu Cys Ile Glu Ser
    25              30              35 ggg ccc ggc tgc acc tgg tgc cag aag ctg aac ttc aca ggg ccg ggg      258
Gly Pro Gly Cys Thr Trp Cys Gln Lys Leu Asn Phe Thr Gly Pro Gly
40              45              50              55 gat cct gac tcc att cgc tgc gac acc cgg cca cag ctg ctc atg agg      306
Asp Pro Asp Ser Ile Arg Cys Asp Thr Arg Pro Gln Leu Leu Met Arg
            60              65              70 ggc tgt gcg gct gac gac atc atg gac ccc aca agc ctc gct gaa acc      354
Gly Cys Ala Ala Asp Asp Ile Met Asp Pro Thr Ser Leu Ala Glu Thr
        75              80              85 cag gaa gac cac aat ggg ggc cag aag cag ctg tcc cca caa aaa gtg      402
Gln Glu Asp His Asn Gly Gly Gln Lys Gln Leu Ser Pro Gln Lys Val
    90              95              100 acg ctt tac ctg cga cca ggc cag gca gca gcg ttc aac gtg acc ttc      450
Thr Leu Tyr Leu Arg Pro Gly Gln Ala Ala Ala Phe Asn Val Thr Phe
105             110             115 cgg cgg gcc aag ggc tac ccc atc gac ctg tac tat ctg atg gac ctc      498
Arg Arg Ala Lys Gly Tyr Pro Ile Asp Leu Tyr Tyr Leu Met Asp Leu
120             125             130             135 tcc tac tcc atg ctt gat gac ctc agg aat gtc aag aag cta ggt ggc      546
Ser Tyr Ser Met Leu Asp Asp Leu Arg Asn Val Lys Lys Leu Gly Gly
            140             145             150 gac ctg ctc cgg gcc ctc aac gag atc acc gag tcc ggc cgc att ggc      594
Asp Leu Leu Arg Ala Leu Asn Glu Ile Thr Glu Ser Gly Arg Ile Gly
        155             160             165 ttc ggg tcc ttc gtg gac aag acc gtg ctg ccg ttc gtg aac acg cac      642
Phe Gly Ser Phe Val Asp Lys Thr Val Leu Pro Phe Val Asn Thr His
    170             175             180 cct gat aag ctg cga aac cca tgc ccc aac aag gag aaa gag tgc cag      690
Pro Asp Lys Leu Arg Asn Pro Cys Pro Asn Lys Glu Lys Glu Cys Gln
185             190             195 ccc ccg ttt gcc ttc agg cac gtg ctg aag ctg acc aac aac tcc aac      738
Pro Pro Phe Ala Phe Arg His Val Leu Lys Leu Thr Asn Asn Ser Asn
200             205             210             215 cag ttt cag acc gag gtc ggg aag cag ctg att tcc gga aac ctg gat      786
Gln Phe Gln Thr Glu Val Gly Lys Gln Leu Ile Ser Gly Asn Leu Asp
            220             225             230 gca ccc gag ggt ggg ctg gac gcc atg atg cag gtc gcc gcc tgc ccg      834
Ala Pro Glu Gly Gly Leu Asp Ala Met Met Gln Val Ala Ala Cys Pro
        235             240             245 gag gaa atc ggc tgg cgc aac gtc acg cgg ctg ctg gtg ttt gcc act      882
Glu Glu Ile Gly Trp Arg Asn Val Thr Arg Leu Leu Val Phe Ala Thr
    250             255             260 gat gac ggc ttc cat ttc gcg ggc gac ggg aag ctg ggc gcc atc ctg      930
Asp Asp Gly Phe His Phe Ala Gly Asp Gly Lys Leu Gly Ala Ile Leu
265             270             275 acc ccc aac gac ggc cgc tgt cac ctg gag gac aac ttg tac aag agg      978
Thr Pro Asn Asp Gly Arg Cys His Leu Glu Asp Asn Leu Tyr Lys Arg
            280             285             290             295 agc aac gaa ttc gac tac cca tcg gtg ggc cag ctg gcg cac aag ctg      1026
Ser Asn Glu Phe Asp Tyr Pro Ser Val Gly Gln Leu Ala His Lys Leu
```

-continued

```
Ser Asn Glu Phe Asp Tyr Pro Ser Val Gly Gln Leu Ala His Lys Leu
            300                 305                 310 gct gaa aac aac atc cag ccc atc ttc gcg gtg acc agt agg atg gtg    1074
Ala Glu Asn Asn Ile Gln Pro Ile Phe Ala Val Thr Ser Arg Met Val
        315                 320                 325 aag acc tac gag aaa ctc acc gag atc atc ccc aag tca gcc gtg ggg    1122
Lys Thr Tyr Glu Lys Leu Thr Glu Ile Ile Pro Lys Ser Ala Val Gly
            330                 335                 340 gag ctg tct gag gac tcc agc aat gtg gtc cat ctc att aag aat gct    1170
Glu Leu Ser Glu Asp Ser Ser Asn Val Val His Leu Ile Lys Asn Ala
        345                 350                 355 tac aat aaa ctc tcc tcc agg gtc ttc ctg gat cac aac gcc ctc ccc    1218
Tyr Asn Lys Leu Ser Ser Arg Val Phe Leu Asp His Asn Ala Leu Pro
360                 365                 370                 375 gac acc ctg aaa gtc acc tac gac tcc ttc tgc agc aat gga gtg acg    1266
Asp Thr Leu Lys Val Thr Tyr Asp Ser Phe Cys Ser Asn Gly Val Thr
            380                 385                 390 cac agg aac cag ccc aga ggt gac tgt gat ggc gtg cag atc aat gtc    1314
His Arg Asn Gln Pro Arg Gly Asp Cys Asp Gly Val Gln Ile Asn Val
        395                 400                 405 ccg atc acc ttc cag gtg aag gtc acg gcc aca gag tgc atc cag gag    1362
Pro Ile Thr Phe Gln Val Lys Val Thr Ala Thr Glu Cys Ile Gln Glu
410                 415                 420 cag tcg ttt gtc atc cgg gcg ctg ggc ttc acg gac ata gtg acc gtg    1410
Gln Ser Phe Val Ile Arg Ala Leu Gly Phe Thr Asp Ile Val Thr Val
        425                 430                 435 cag gtt ctt ccc cag tgt gag tgc cgg tgc cgg gac cag agc aga gac    1458
Gln Val Leu Pro Gln Cys Glu Cys Arg Cys Arg Asp Gln Ser Arg Asp
440                 445                 450                 455 cgc agc ctc tgc cat ggc aag ggc ttc ttg gag tgc ggc atc tgc agg    1506
Arg Ser Leu Cys His Gly Lys Gly Phe Leu Glu Cys Gly Ile Cys Arg
            460                 465                 470 tgt gac act ggc tac att ggg aaa aac tgt gag tgc cag aca cag ggc    1554
Cys Asp Thr Gly Tyr Ile Gly Lys Asn Cys Glu Cys Gln Thr Gln Gly
        475                 480                 485 cgg agc agc cag gag ctg gaa gga agc tgc cgg aag gac aac aac tcc    1602
Arg Ser Ser Gln Glu Leu Glu Gly Ser Cys Arg Lys Asp Asn Asn Ser
            490                 495                 500 atc atc tgc tca ggg ctg ggg gac tgt gtc tgc ggg cag tgc ctg tgc    1650
Ile Ile Cys Ser Gly Leu Gly Asp Cys Val Cys Gly Gln Cys Leu Cys
505                 510                 515 cac acc agc gac gtc ccc ggc aag ctg ata tac ggg cag tac tgc gag    1698
His Thr Ser Asp Val Pro Gly Lys Leu Ile Tyr Gly Gln Tyr Cys Glu
520                 525                 530                 535 tgt gac acc atc aac tgt gag cgc tac aac ggc cag gtc tgc ggc ggc    1746
Cys Asp Thr Ile Asn Cys Glu Arg Tyr Asn Gly Gln Val Cys Gly Gly
            540                 545                 550 ccg ggg agg ggg ctc tgc ttc tgc ggg aag tgc cgc tgc cac ccg ggc    1794
Pro Gly Arg Gly Leu Cys Phe Cys Gly Lys Cys Arg Cys His Pro Gly
        555                 560                 565 ttt gag ggc tca gcg tgc cag tgc gag agg acc act gag ggc tgc ctg    1842
Phe Glu Gly Ser Ala Cys Gln Cys Glu Arg Thr Thr Glu Gly Cys Leu
            570                 575                 580 aac ccg cgg cgt gtt gag tgt agt ggt cgt ggc cgg tgc cgc tgc aac    1890
Asn Pro Arg Arg Val Glu Cys Ser Gly Arg Gly Arg Cys Arg Cys Asn
585                 590                 595 gta tgc gag tgc cat tca ggc tac cag ctg cct ctg tgc cag gag tgc    1938
Val Cys Glu Cys His Ser Gly Tyr Gln Leu Pro Leu Cys Gln Glu Cys
600                 605                 610                 615 ccc ggc tgc ccc tca ccc tgt ggc aag tac atc tcc tgc gcc gag tgc    1986
```

```
                Pro Gly Cys Pro Ser Pro Cys Gly Lys Tyr Ile Ser Cys Ala Glu Cys
                                620                 625                 630 ctg aag ttc gaa aag ggc ccc ttt ggg aag aac tgc agc gcg gcg tgt        2034
Leu Lys Phe Glu Lys Gly Pro Phe Gly Lys Asn Cys Ser Ala Ala Cys
            635                 640                 645 ccg ggc ctg cag ctg tcg aac aac ccc gtg aag ggc agg acc tgc aag        2082
Pro Gly Leu Gln Leu Ser Asn Asn Pro Val Lys Gly Arg Thr Cys Lys
        650                 655                 660 gag agg gac tca gag ggc tgc tgg gtg gcc tac acg ctg gag cag cag        2130
Glu Arg Asp Ser Glu Gly Cys Trp Val Ala Tyr Thr Leu Glu Gln Gln
    665                 670                 675 gac ggg atg gac cgc tac ctc atc tat gtg gat gag agc cga gag tgt        2178
Asp Gly Met Asp Arg Tyr Leu Ile Tyr Val Asp Glu Ser Arg Glu Cys
680                 685                 690                 695 gtg gca ggc ccc aac atc gcc gcc atc gtc ggg ggc acc gtg gca ggc        2226
Val Ala Gly Pro Asn Ile Ala Ala Ile Val Gly Gly Thr Val Ala Gly
                700                 705                 710 atc gtg ctg atc ggc att ctc ctg gtc atc tgg aag gct ctg atc            2274
Ile Val Leu Ile Gly Ile Leu Leu Val Ile Trp Lys Ala Leu Ile
            715                 720                 725 cac ctg agc gac ctc cgg gag tac agg cgc ttt gag aag gag aag ctc        2322
His Leu Ser Asp Leu Arg Glu Tyr Arg Arg Phe Glu Lys Glu Lys Leu
        730                 735                 740 aag tcc cag tgg aac aat gat aat ccc ctt ttc aag agc gcc acc acg        2370
Lys Ser Gln Trp Asn Asn Asp Asn Pro Leu Phe Lys Ser Ala Thr Thr
    745                 750                 755 acg gtc atg aac ccc aag ttt gct gag agt taggagcact tggtgaagac         2420
Thr Val Met Asn Pro Lys Phe Ala Glu Ser
760                 765 aaggccgtca ggacccacca tgttaattaa aagggtgggc gcgccgaccc agctttcttg     2480
tacaaagtgg ttgatctaga gggcccgcgg ttcgaaggta agcctatccc taaccctctc     2540
ctcggtctcg attctacgcg taccggttag taatgagttt aaacggggga ggctaactga     2600
aacacggaag                                                            2610

<210> SEQ ID NO 16
<211> LENGTH: 769
<212> TYPE: PRT
<213> ORGANISM: Homo sapiens

<400> SEQUENCE: 16

Met Leu Gly Leu Arg Pro Pro Leu Leu Ala Leu Val Gly Leu Leu Ser
1               5                   10                  15

Leu Gly Cys Val Leu Ser Gln Glu Cys Thr Lys Phe Lys Val Ser Ser
            20                  25                  30

Cys Arg Glu Cys Ile Glu Ser Gly Pro Gly Cys Thr Trp Cys Gln Lys
        35                  40                  45

Leu Asn Phe Thr Gly Pro Gly Asp Pro Asp Ser Ile Arg Cys Asp Thr
    50                  55                  60

Arg Pro Gln Leu Leu Met Arg Gly Cys Ala Ala Asp Asp Ile Met Asp
65                  70                  75                  80

Pro Thr Ser Leu Ala Glu Thr Gln Glu Asp His Asn Gly Gly Gln Lys
                85                  90                  95

Gln Leu Ser Pro Gln Lys Val Thr Leu Tyr Leu Arg Pro Gly Gln Ala
            100                 105                 110

Ala Ala Phe Asn Val Thr Phe Arg Arg Ala Lys Gly Tyr Pro Ile Asp
        115                 120                 125

Leu Tyr Tyr Leu Met Asp Leu Ser Tyr Ser Met Leu Asp Asp Leu Arg
```

-continued

```
            130                 135                 140
Asn Val Lys Lys Leu Gly Gly Asp Leu Leu Arg Ala Leu Asn Glu Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Asp Lys Leu Arg Asn Pro Cys Pro
                180                 185                 190

Asn Lys Glu Lys Glu Cys Gln Pro Pro Phe Ala Phe Arg His Val Leu
                195                 200                 205

Lys Leu Thr Asn Asn Ser Asn Gln Phe Gln Thr Glu Val Gly Lys Gln
210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
                260                 265                 270

Gly Lys Leu Gly Ala Ile Leu Thr Pro Asn Asp Gly Arg Cys His Leu
                275                 280                 285

Glu Asp Asn Leu Tyr Lys Arg Ser Asn Glu Phe Asp Tyr Pro Ser Val
                290                 295                 300

Gly Gln Leu Ala His Lys Leu Ala Glu Asn Asn Ile Gln Pro Ile Phe
305                 310                 315                 320

Ala Val Thr Ser Arg Met Val Lys Thr Tyr Glu Lys Leu Thr Glu Ile
                325                 330                 335

Ile Pro Lys Ser Ala Val Gly Glu Leu Ser Glu Asp Ser Ser Asn Val
                340                 345                 350

Val His Leu Ile Lys Asn Ala Tyr Asn Lys Leu Ser Ser Arg Val Phe
                355                 360                 365

Leu Asp His Asn Ala Leu Pro Asp Thr Leu Lys Val Thr Tyr Asp Ser
370                 375                 380

Phe Cys Ser Asn Gly Val Thr His Arg Asn Gln Pro Arg Gly Asp Cys
385                 390                 395                 400

Asp Gly Val Gln Ile Asn Val Pro Ile Thr Phe Gln Val Lys Val Thr
                405                 410                 415

Ala Thr Glu Cys Ile Gln Glu Gln Ser Phe Val Ile Arg Ala Leu Gly
                420                 425                 430

Phe Thr Asp Ile Val Thr Val Gln Val Leu Pro Gln Cys Glu Cys Arg
                435                 440                 445

Cys Arg Asp Gln Ser Arg Asp Arg Ser Leu Cys His Gly Lys Gly Phe
450                 455                 460

Leu Glu Cys Gly Ile Cys Arg Cys Asp Thr Gly Tyr Ile Gly Lys Asn
465                 470                 475                 480

Cys Glu Cys Gln Thr Gln Gly Arg Ser Ser Gln Glu Leu Glu Gly Ser
                485                 490                 495

Cys Arg Lys Asp Asn Asn Ser Ile Ile Cys Ser Gly Leu Gly Asp Cys
                500                 505                 510

Val Cys Gly Gln Cys Leu Cys His Thr Ser Asp Val Pro Gly Lys Leu
                515                 520                 525

Ile Tyr Gly Gln Tyr Cys Glu Cys Asp Thr Ile Asn Cys Glu Arg Tyr
                530                 535                 540

Asn Gly Gln Val Cys Gly Gly Pro Gly Arg Gly Leu Cys Phe Cys Gly
545                 550                 555                 560
```

-continued

```
Lys Cys Arg Cys His Pro Gly Phe Glu Gly Ser Ala Cys Gln Cys Glu
            565                 570                 575
Arg Thr Thr Glu Gly Cys Leu Asn Pro Arg Arg Val Glu Cys Ser Gly
                580                 585                 590
Arg Gly Arg Cys Arg Cys Asn Val Cys Glu Cys His Ser Gly Tyr Gln
            595                 600                 605
Leu Pro Leu Cys Gln Glu Cys Pro Gly Cys Pro Ser Pro Cys Gly Lys
            610                 615                 620
Tyr Ile Ser Cys Ala Glu Cys Leu Lys Phe Glu Lys Gly Pro Phe Gly
625                 630                 635                 640
Lys Asn Cys Ser Ala Ala Cys Pro Gly Leu Gln Leu Ser Asn Asn Pro
                645                 650                 655
Val Lys Gly Arg Thr Cys Lys Glu Arg Asp Ser Glu Gly Cys Trp Val
            660                 665                 670
Ala Tyr Thr Leu Glu Gln Gln Asp Gly Met Asp Arg Tyr Leu Ile Tyr
            675                 680                 685
Val Asp Glu Ser Arg Glu Cys Val Ala Gly Pro Asn Ile Ala Ala Ile
        690                 695                 700
Val Gly Gly Thr Val Ala Gly Ile Val Leu Ile Gly Ile Leu Leu Leu
705                 710                 715                 720
Val Ile Trp Lys Ala Leu Ile His Leu Ser Asp Leu Arg Glu Tyr Arg
                725                 730                 735
Arg Phe Glu Lys Glu Lys Leu Lys Ser Gln Trp Asn Asn Asp Asn Pro
            740                 745                 750
Leu Phe Lys Ser Ala Thr Thr Val Met Asn Pro Lys Phe Ala Glu
            755                 760                 765
Ser
```